(12) United States Patent
Agrawal et al.

(10) Patent No.: US 11,273,069 B2
(45) Date of Patent: Mar. 15, 2022

(54) WEARABLE APPARATUSES, METHODS, AND SYSTEMS FOR DIAGNOSIS, ANALYSIS, THERAPY AND OTHER USES

(71) Applicant: The Trustees of Columbia University in the City of New York, New York, NY (US)

(72) Inventors: Sunil K. Agrawal, Newark, DE (US); Haohan Zhang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 433 days.

(21) Appl. No.: 16/034,116

(22) Filed: Jul. 12, 2018

(65) Prior Publication Data

US 2019/0015237 A1    Jan. 17, 2019

Related U.S. Application Data

(63) Continuation-in-part of application No. PCT/US2017/013200, filed on Jan. 12, 2017.
(Continued)

(51) Int. Cl.
*A61F 5/055* (2006.01)
*A61F 5/05* (2006.01)
(Continued)

(52) U.S. Cl.
CPC .......... *A61F 5/05883* (2013.01); *A61H 1/02* (2013.01); *A61H 1/0296* (2013.01); *A61F 2005/0155* (2013.01)

(58) Field of Classification Search
CPC ......... A61F 5/05883; A61F 2005/0155; A61H 1/0296; A61H 1/02
See application file for complete search history.

(56) References Cited

U.S. PATENT DOCUMENTS

| 3,776,224 A | * | 12/1973 | McFarland | ............. | A61F 5/055 602/18 |
| 4,079,251 A | * | 3/1978 | Osann, Jr. | ................ | G01D 5/36 250/231.16 |

(Continued)

FOREIGN PATENT DOCUMENTS

| WO | 2004019834 A1 | 3/2004 |
| WO | 2014092521 A1 | 6/2014 |

OTHER PUBLICATIONS

International Search Report and Written Opinion for International Application No. PCT/US2017/013200 dated Apr. 7, 2017.
(Continued)

*Primary Examiner* — Camtu T Nguyen
(74) *Attorney, Agent, or Firm* — Potomac Law Group, PLLC

(57) ABSTRACT

A wearable neck brace uses, for example, only three actuators but provides natural motion of the head and neck. This is achieved despite the fact that the head has six degrees of freedom including 3 translation and 3 rotation. In embodiments, a wearable neck brace actively controls the head of the wearer responsively to commands from a user interface such as an eye tracking input device. In further embodiments, a force-field is generated by actuators to provide assistance and/or training for weak muscles. Spring compensation may be provided for a passive support with flexibility. Encoders may be provided to generate treatment logs to support analysis of a patient's condition or progress or to provide therapy-facilitating (or athletic training-facilitating) feedback to the user.

22 Claims, 34 Drawing Sheets

Related U.S. Application Data

(60) Provisional application No. 62/618,510, filed on Jan. 17, 2018, provisional application No. 62/277,952, filed on Jan. 12, 2016.

(51) Int. Cl.
*A61F 5/058* (2006.01)
*A61H 1/02* (2006.01)
*A61F 5/01* (2006.01)

(56) References Cited

U.S. PATENT DOCUMENTS

| | | | |
|---|---|---|---|
| 4,562,833 A | | 1/1986 | Pujals |
| 4,708,129 A | | 11/1987 | Pujals |
| 4,893,808 A | | 1/1990 | McIntyre et al. |
| 5,272,770 A | * | 12/1993 | Allen ............... A42B 3/0473 2/421 |
| 5,575,763 A | | 11/1996 | Nagata et al. |
| 5,624,387 A | | 4/1997 | McGuinness |
| 7,371,221 B1 | | 5/2008 | Baker |
| 7,430,767 B2 | * | 10/2008 | Nagely ............... A42B 3/0473 2/425 |
| 7,537,573 B2 | | 5/2009 | Horst |
| 8,341,770 B2 | | 1/2013 | Siegler et al. |
| 9,320,669 B2 | | 4/2016 | Bonutti et al. |
| 2007/0156071 A1 | | 7/2007 | Cojbasic |
| 2008/0004556 A1 | | 1/2008 | Gehlbach et al. |
| 2008/0209617 A1 | * | 9/2008 | Castillo ............... A41D 13/0512 2/461 |
| 2010/0087764 A1 | * | 4/2010 | Linares ............... A61F 5/055 602/18 |
| 2010/0204628 A1 | | 8/2010 | Ghajar |
| 2010/0312243 A1 | | 12/2010 | Ross et al. |
| 2011/0060260 A1 | | 3/2011 | Siegler et al. |
| 2012/0136292 A1 | | 5/2012 | Pepin |
| 2015/0088043 A1 | | 3/2015 | Goldfield et al. |
| 2015/0202072 A1 | | 7/2015 | Glazener et al. |
| 2015/0328038 A1 | | 11/2015 | Rosenfeld et al. |
| 2015/0366694 A1 | | 12/2015 | Bujold et al. |
| 2016/0074202 A1 | | 3/2016 | Reed et al. |

OTHER PUBLICATIONS

Zhang et al., "Kinematic Design of a Dynamic Brace for Measurement of Head/Neck Motion", IEEE Robotics and Automation Letters, published online Feb. 17, 2017, pp. 1428-1435.

International Preliminary Report on Patentability for International Application No. PCT/US2017/013200 dated Jul. 26, 2018.

Douglas et al., "Motorized Headrest for People with Neck Muscle Weakness", RESNA Conference, May 13, 2010.

Glazener, "Pilot study to determine the effectiveness of a new neck brace design for patients with amyotrophic ateral sclerosis", Journal of Nursing Education and Practice, Mar. 31, 2014, vol. 4(6).

Duerfelli et al., "Kinematic modeling of head-neck movements", IEEE Transactions on Systems, Man, and Cybernetics—Part A: Systems and Humans, Nov. 1999, vol. 29(6), p. 604-615.

* cited by examiner

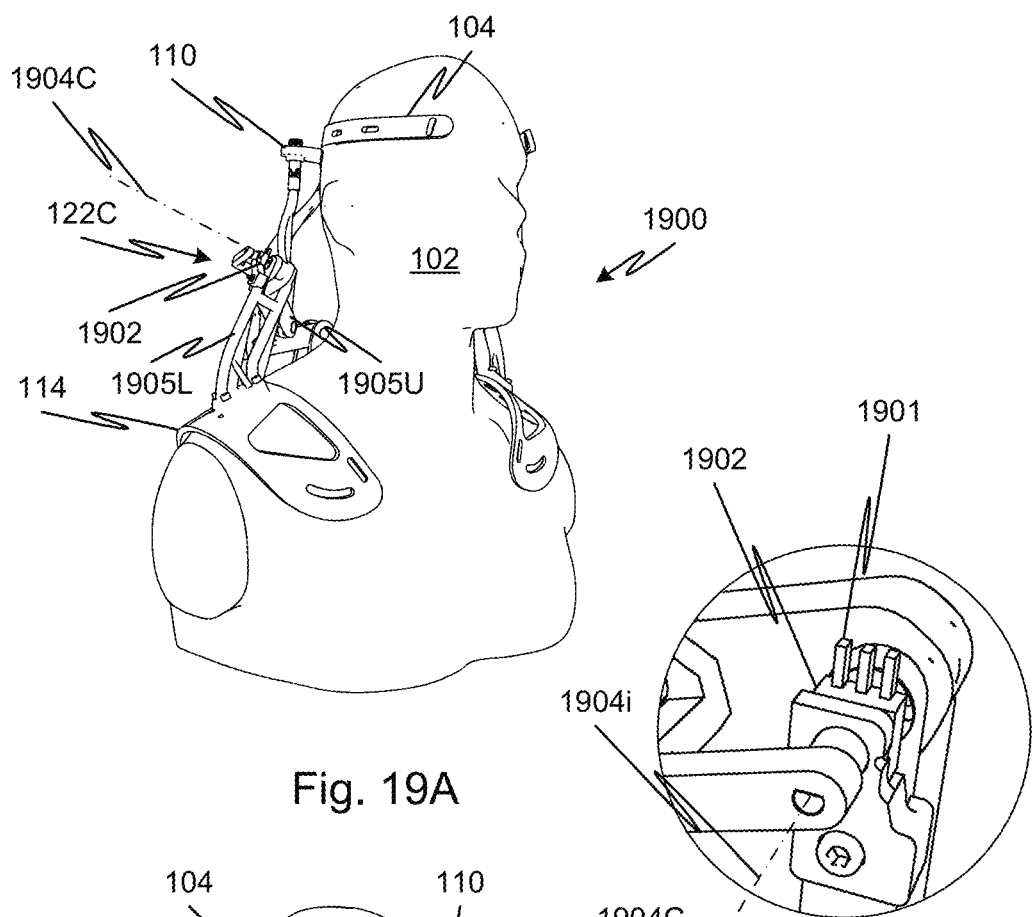
Fig. 19A
Fig. 19C
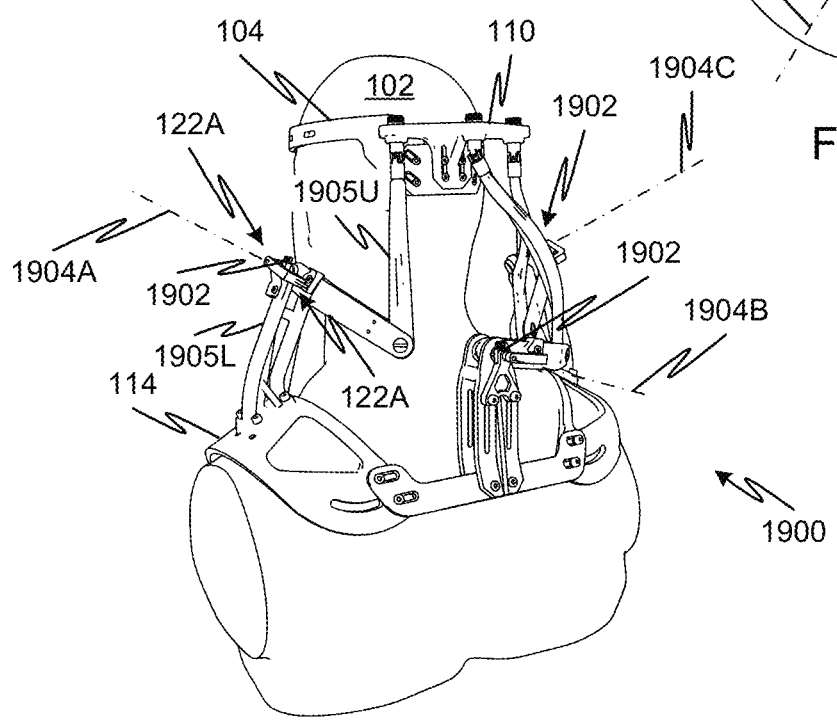
Fig. 19B

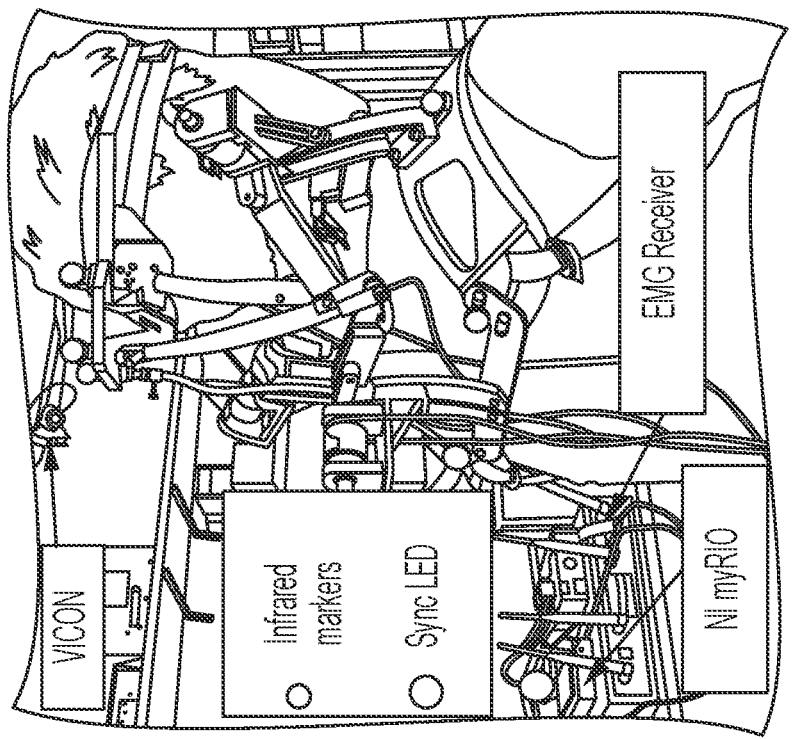
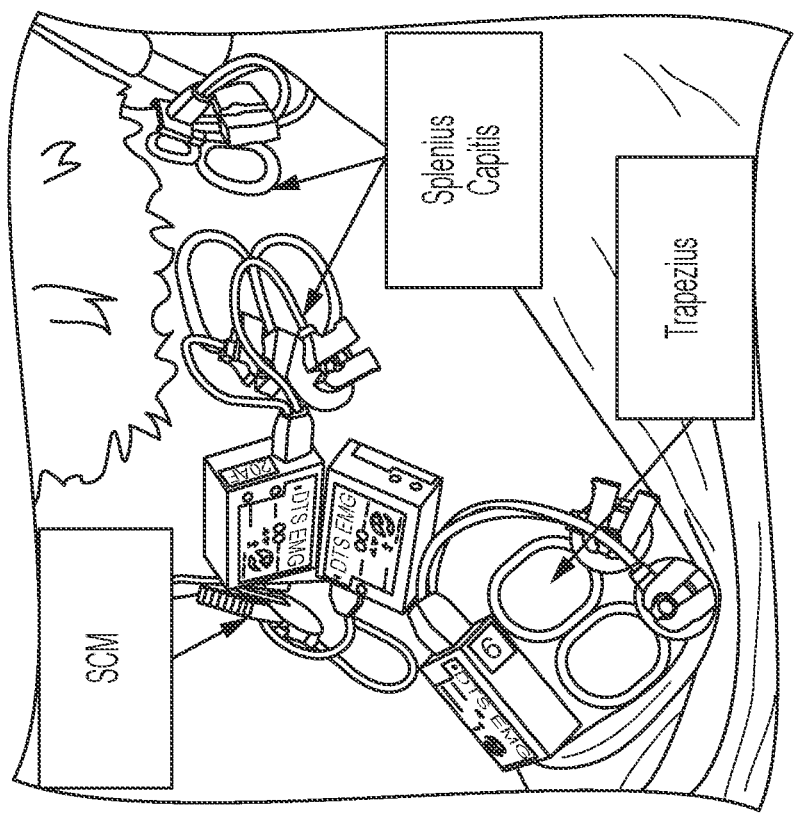
Fig. 31

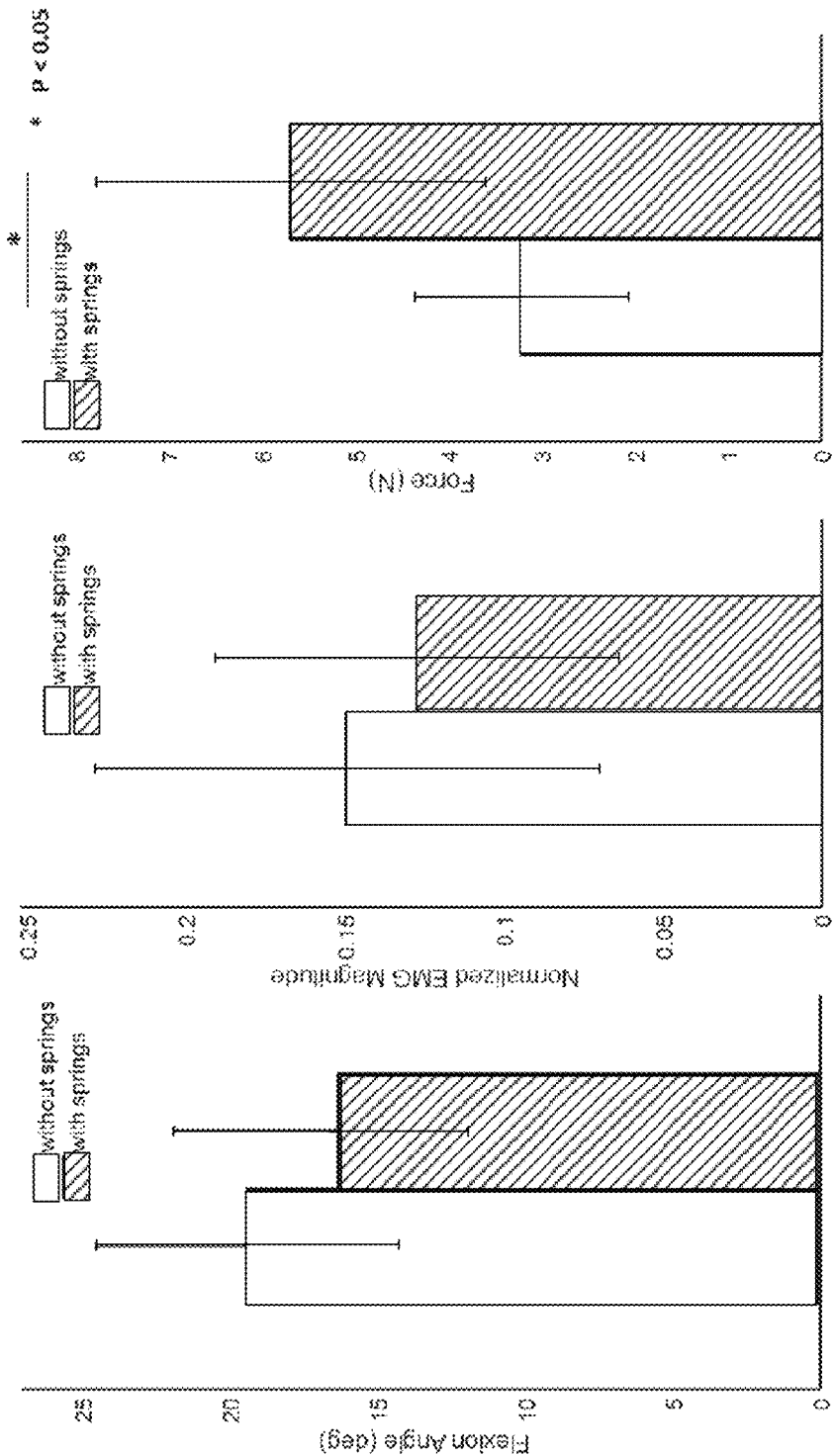

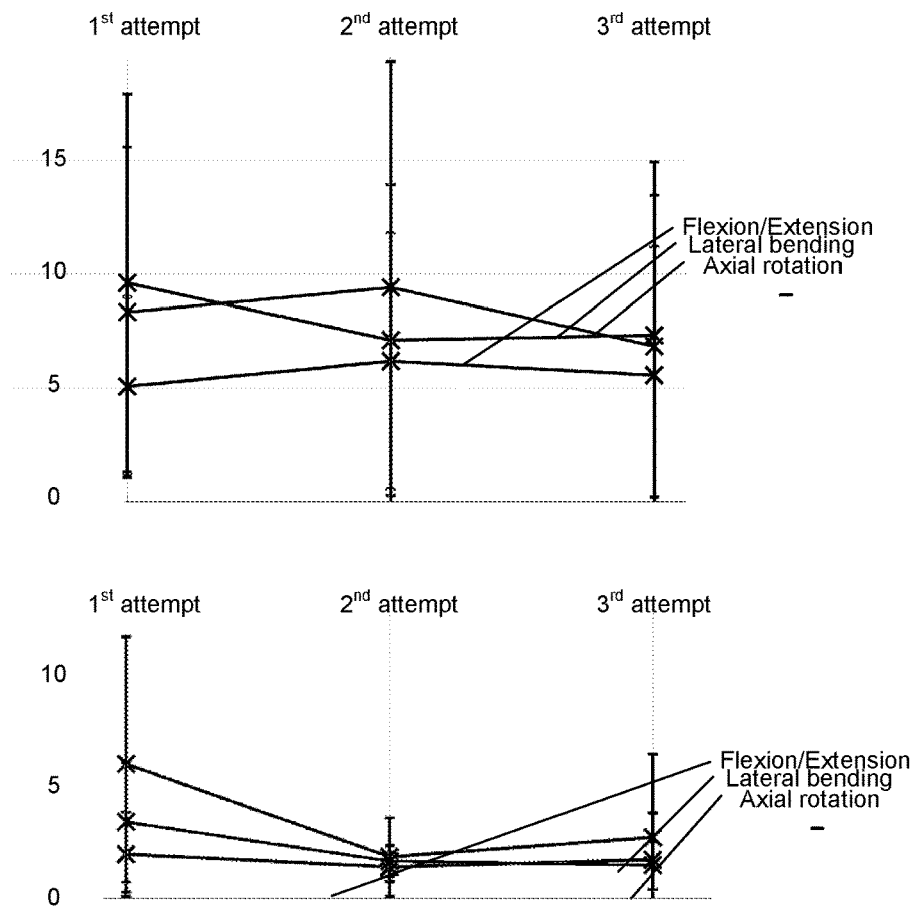
Comparison of group average in settling time in three attempts during targeting tasks with neck brace and with joystick.
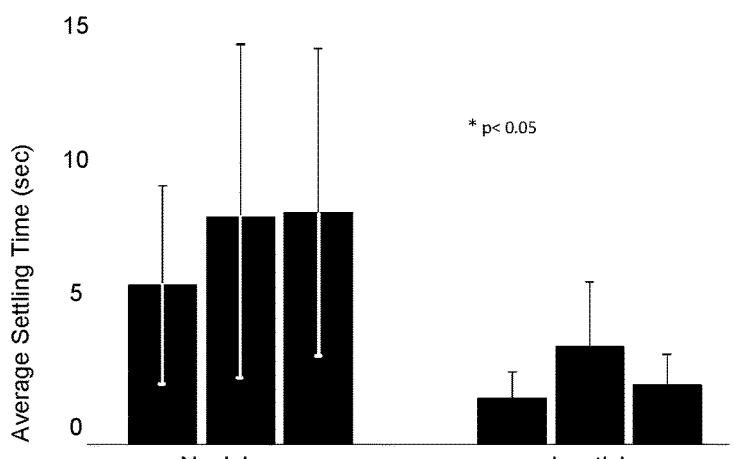
Group average and standard deviation of settling time in targeting tasks.
Fig. 41

WEARABLE APPARATUSES, METHODS, AND SYSTEMS FOR DIAGNOSIS, ANALYSIS, THERAPY AND OTHER USES

CROSS REFERENCE TO RELATED APPLICATIONS

This application claims the benefit of U.S. Provisional Application 62/618,510, filed 17 Jan. 2018, and is a continuation-in-part of International Patent Application PCT/US2017/013200 filed 12 Jan. 2017, which claims the benefit of U.S. Provisional Application 62/277,952 filed 12 Jan. 2016. The foregoing is each hereby incorporated by reference in its entirety herein.

FIELD

The present disclosure relates generally to rehabilitation or assistance devices, and more particularly, to systems, methods, and devices for providing support, training, and other corrective, rehabilitation, or assistance to the neck of a user.

BACKGROUND

Static neck braces are commonly used to provide support for persons with neck problems. For example weakness due to stroke, degenerative diseases, surgery, or neck injury may require support of the neck to facilitate recovery or improvement for pathology. In general, the goals of these braces are to correct or limit the position of the head or neck or both. The rigidity of conventional braces makes them difficult to wear for extended periods of time and interferes with typical activities of daily living.

Head drop is commonly seen in many neurodegenerative diseases, including Amyotrophic Lateral Sclerosis (ALS). The neck extensor muscles progressively weaken and the patients feel fatigue in holding or moving the head normally. With progression of the disease, the head drops completely, making it a challenge for the patient to make eye contact, talk, swallow, or breathe. In addition to the choking hazard, it creates issues of social embarrassment and psychological decline. There is no cure for head drop in patients with ALS. There are other neuromuscular disorders, such as cervical dystonia, myasthenia gravis, fascioscapulohumeral dystrophy where patients are unable to keep their head in a configuration due to muscle weakness and/or involuntary contractions of the neck muscles. Once the extensor muscles of the neck lose strength, they cannot be restored through therapy, pharmacological treatment or surgical interventions. Typically, the loss in muscle strength is alleviated through assistive devices. Reclining wheelchairs are sometimes used, where the chair can be tilted so that the patient can make eye contact.

SUMMARY

The disclosed subject matter relates to dynamic neck braces that can assist a user with muscle weakness to move their head and respond to sensory cues. The disclosed neck brace embodiments can to assist neck movements, support strengthening exercises for the neck motion, monitor applied forces and dynamic motion of the neck with inbuilt sensors, and promote learning through repetitive motion in neurological patients. The disclosed subject matter provides solutions to issues such as how a neck brace can conform to the motion of a user, how control interfaces may be integrated, to promote assistance and training in neurological patients, how passive or semi-active braces can consume minimal power for extended use, and how to provide the ability to measure the effectiveness of the articulated brace in patients with ALS and other neck motion disorders. The disclosed embodiments may support the efforts of physical therapists in their efforts to conduct exercises to improve patients with neck disabilities. In addition, however, the disclosed embodiments may also support training for normal persons, such as athletes, that may be at risk of injury or persons with less pathological issues such as poor posture. This brace may also be used in applications that require the head to carry substantive dynamic load, e.g., racecar drivers, military soldiers. It can also be used as a hand-free joystick input by the human head, which can be found useful in fields such as gaming and military usage. The disclosed embodiments in all areas of use may also help to advance a need for consistency in providing a platform that provides precisely controllable conditions that ensure exercises generate consistent challenges and by providing repeatability in the quantitative characterization of exercises. All of the above may be accomplished with minimal interference, except as required for exercise implementation, adverse impact on the range of motion of the head, permitting natural head translation as well as rotation, consistent registration on, and comfort of, the wearer, as well as consistent and accurate measurement of body movement.

In embodiments, a 3 degree of freedom (DOF) dynamic neck brace mimics the coupled translation and rotation of the head relative to the trunk in typical daily movements. The brace embodiments were developed, in part, based on motion capture data of the kinematics of the head/neck of a healthy subject. In embodiments, three potentiometers are used to measure the joint angles within the brace. The data is used to compute the position and the orientation of the head through forward kinematics using a numerical approach. In additional embodiments, the 3 DOF system is extended to 6 DOF configuration by the addition of linear actuators.

A wearable neck brace uses, for example, only three actuators but provides natural motion of the head and neck. This is achieved even though the head has six degrees of freedom including 3 translations and 3 rotations. In embodiments, a wearable neck brace actively controls the head of the wearer responsively to commands from a user interface such as an eye tracking input device. In further embodiments, a force-field is generated by actuators to provide assistance and/or training for weak muscles. Spring compensation may be provided for a passive support with flexibility. Encoders may be provided to generate treatment logs to support analysis of a patient's condition or progress or to provide therapy-facilitating (or athletic training-facilitating) feedback to the user. Another way in which the disclosed embodiments may be employed and configured is to provide for the measurement on non-static pathology, for example, where protractors and similar measurement techniques are not appropriate for diseases where the head has constant involuntary motions, such as cervical dystonia. Thus, embodiments provide the capability for dynamic assessment and characterization of patient pathology. The dynamic neck brace, synchronized with EMG measurements, provides the ability to characterize the neck motion quantitatively both in terms of motion/force and create a scientific database both for healthy subjects and those with diseases. The data from healthy subjects can be used as a way to compare the characteristics of subjects with specific diseases.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 19A, 19B, and 19C show a brace according to the disclosed embodiments with position encoders connected to the first revolute (R) joints.

FIG. 31 shows placement of sensors during experiments described herein.

FIG. 34A: average range of motion in each direction FIG. 34B: EMG data from a muscle group averaged from both sides of the body, and FIG. 34C: average forces expressed in the sensor frame.

FIGS. 35A-35C show a comparison of average flexion angle, average muscle activations, and average force received by the head of the subjects as a group during Task 2 where each bar represents FIG. 35A: average head angles in flexion; FIG. 35B: EMG averaged by all six muscles; and FIG. 35C: average magnitude of force in z-axis in sensor frame.

FIGS. 38-41 show results of the testing summarized in FIG. 37.

DETAILED DESCRIPTION

Figure 1:
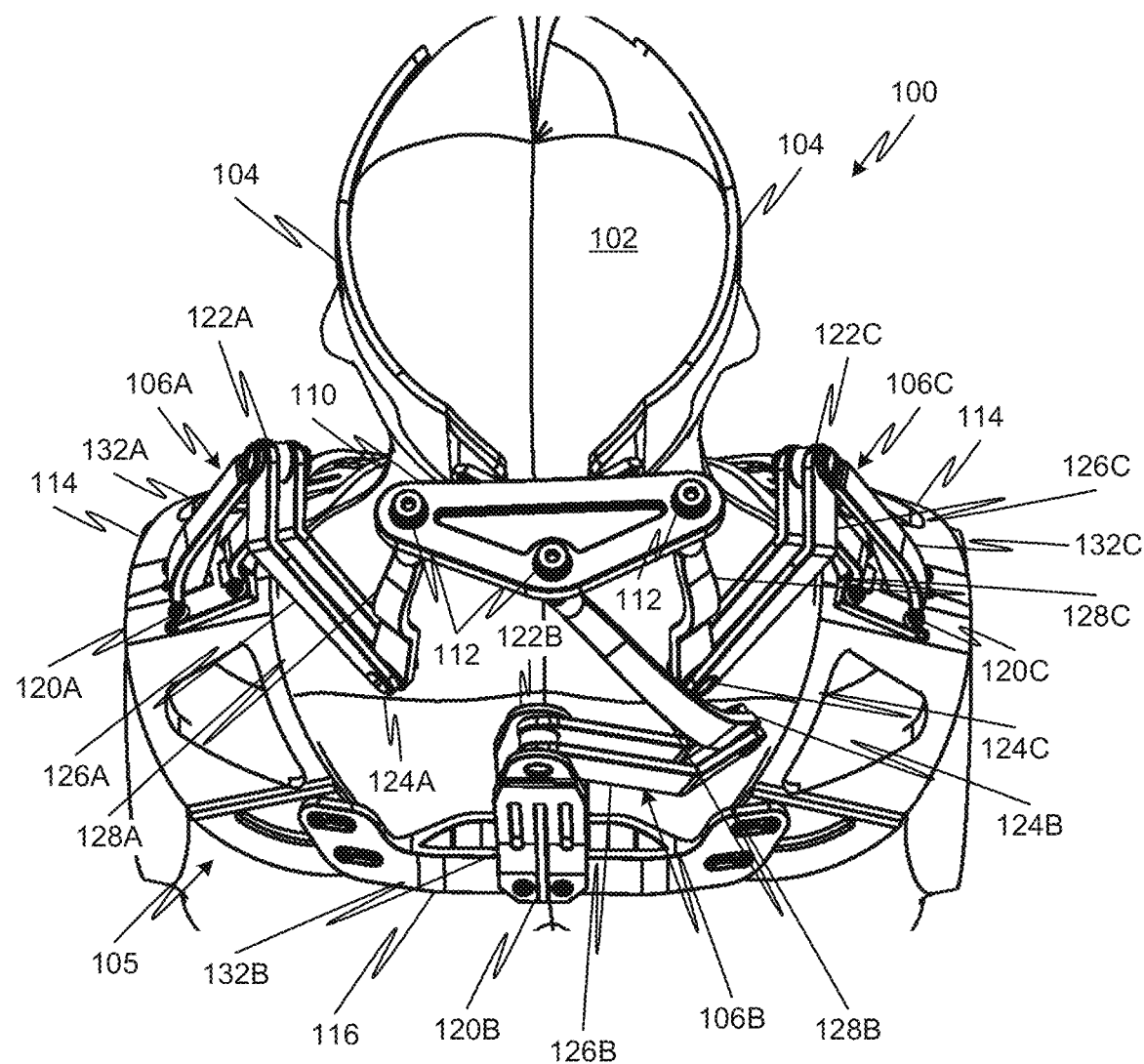
FIG. 1 shows a rear view of a neck brace viewed from a high vantage according to embodiments of the disclosed subject matter.
Figure 2:
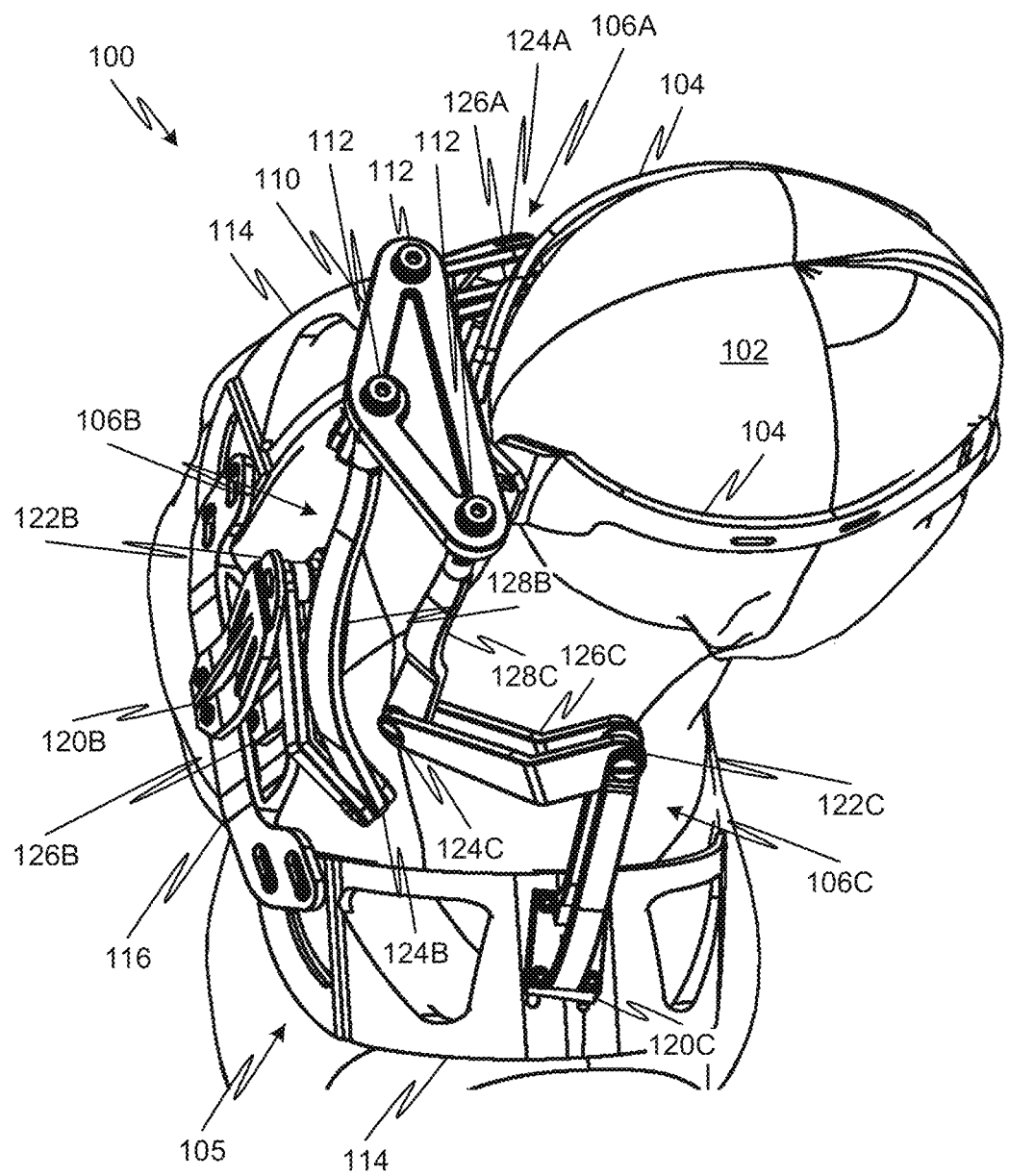
FIG. 2 shows a side view of the neck brace of FIG. 1 viewed from a high vantage.
Figure 3:
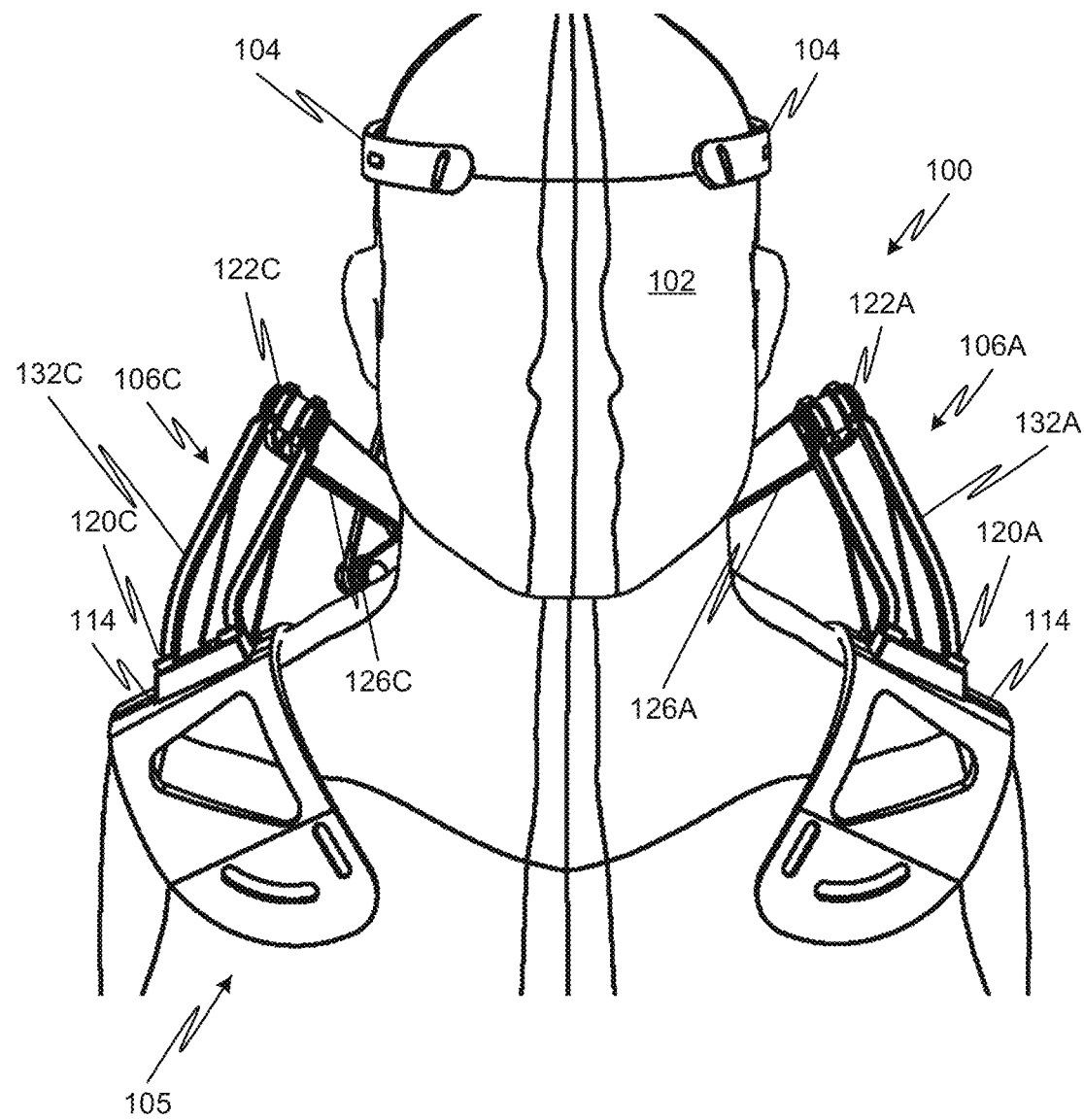
FIG. 3 shows a front view of the neck brace of FIG. 1.
Figure 4:
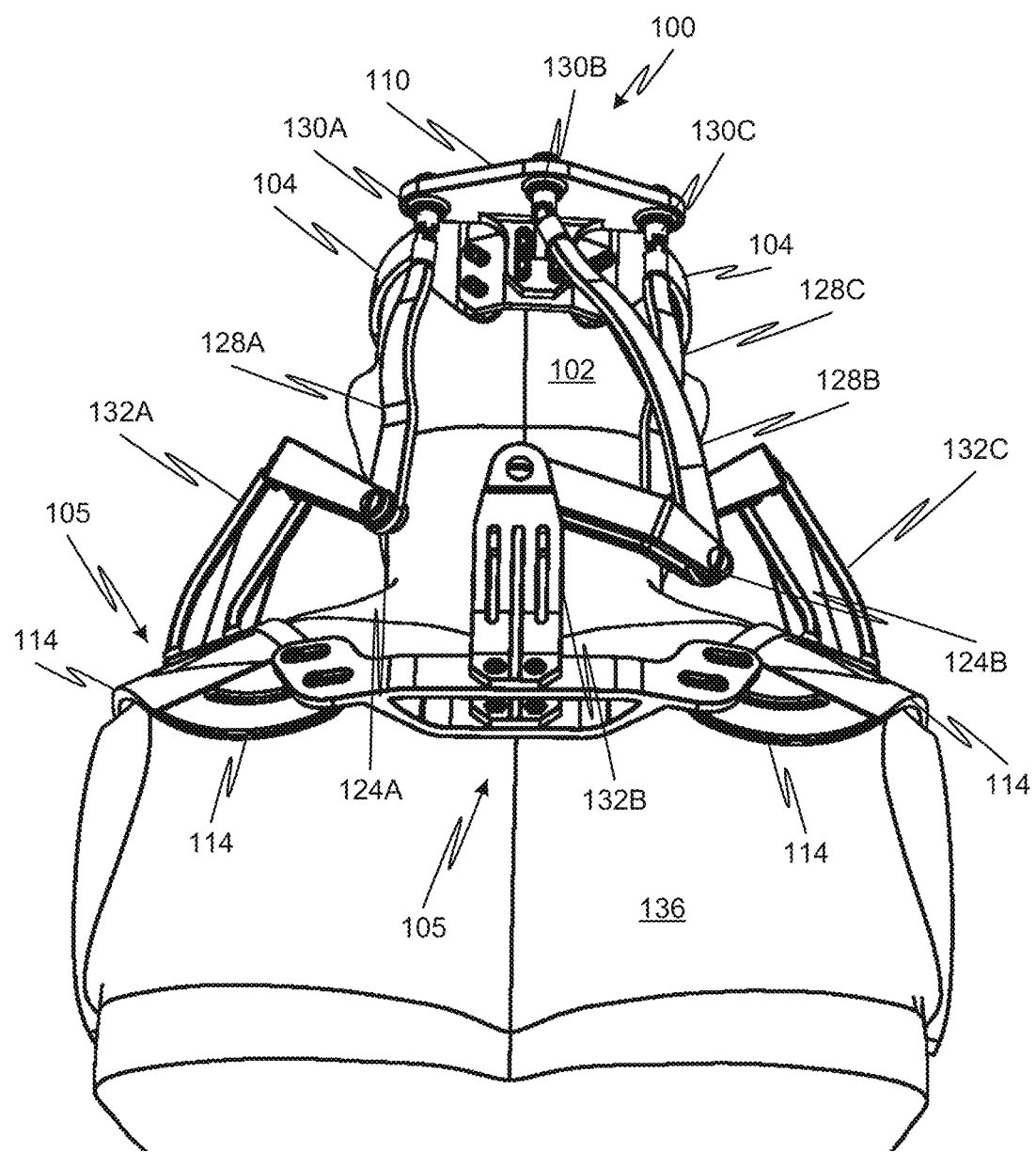
FIG. 4 shows a rear view of the neck brace of FIG. 1 viewed from a low vantage.

The motion of the head relative to the trunk may be approximated as purely spherical from observation in daily life. From a biomechanics perspective, however, the head is connected to the trunk through a series of cervical vertebrae and joints. As a consequence, the head performs a predominant spherical motion with a small translation. Thus, a brace which can only rotate would not fully accommodate the natural movement of the human head. A feature of the disclosed brace embodiments is that they treat the head and neck as a whole and propose an architecture that can sustain both rotation and translation of the head/neck relative to trunk.

Referring to FIGS. 1-4 and 6, a 3 DOF spherical mechanism may be configured so that it can perform the coupled translational and rotational motion during the motion of head and neck. If there exist three distinct and non-collinear points on a rigid body which move on three concentric spheres, the entire body must perform a spherical motion about the common center. However, if the motion is such that the three distinct and non-collinear points in the body move on non-concentric spheres, the rotation and the translation of the rigid body are coupled. The end-effecter now performs both translational and rotational motion with respect to its base. In the figure, each chain has two intersecting R-joints such that the end-effecter points Ai move on circles around Ci, respectively. (iii) With this architecture of the mechanism, its geometric parameters are optimized such that the translational and rotational motions of the end-effecter provided by the brace match well with observed human head motions collected from a motion capture system.

In the disclosed embodiments, two revolute joints within each RRS chain intersect at a point. The point may be fixed relative to a base, for example, the disclosed shoulder support. Advantages of this feature include: (i) a parallel mechanism allows the placement of smaller actuators on the base frame to reduce the moving inertia; (ii) RRS chains may be used which are easy to realize with light weight; (iii) for fabrication expedience, it is easier to ensure that two successive revolute joints in a chain have a common intersection point rather than alternatives such as providing an intersection point from three different chains. In the limit, when the intersecting points of the axes of each chain are the same, the system yields spherical motion of the end-effecter.

Referring to FIGS. 1-4, a linkage fastener 100 has a head support 104 affixed to a head platform 110 that connects to a shoulder platform 105 through a left linkage 106A, center linkage 106B, and a right linkage 106C. Each of the linkages, left linkage 106A, center linkage 106B, and right linkage 106C is of RRS type meaning it has three joints in series starting from a respective one of a left linkage pedestal 132A, center linkage pedestal 132B, and right linkage pedestal 132C fixedly mounted to the shoulder platform 105 by a respective one of a left pedestal fastener 120A, a center pedestal fastener 120B, and a right pedestal fastener 120C.

A first R (rotational) joint, left linkage lower R joint 122A, connects a left linkage lower R link 126A to the left linkage pedestal 132A. A second R joint, left linkage upper R joint 124A, connects left linkage lower R link 126A to a left linkage upper R link 128A. An S (spherical) joint, left spherical joint 130A connects the left linkage upper R link 128A to the head platform 110. A first R joint, center linkage lower R joint 122B, connects a center linkage lower R link 126B to the center linkage pedestal 132B. A second R joint, center linkage upper R joint 124B, connects center linkage lower R link 126B to a center linkage upper R link 128B. An S joint, center spherical joint 130B connects the center linkage upper R link 128B to the head platform 110 at a point offset from the point where left spherical joint 130A attaches. A first R joint, right linkage lower R joint 122C, connects a right linkage lower R link 126C to the right linkage pedestal 132C. A second R joint, right linkage upper R joint 124C, connects right linkage lower R link 126C to a right linkage upper R link 128C. An S joint, right spherical joint 130C connects the right linkage upper R link 128C to the head platform 110 at a point offset from the points where left spherical joint 130A and center spherical joint 130B attach. The three points where spherical joints 130A, 130B, and 130C attach to the head platform 110 may form any suitable shape for attachment to a head interface, for example an isosceles triangle.

The head support 104 may be adjustable to fit different users. The linkages may be customized for the users or made from fastened members whose lengths can be adjusted. The left, center, and right linkage pedestals 132A, 132B, and 132C may include a pair of plates as shown to provide lateral stiffness. The linkages may be of aluminum or other lightweight metal as well as plastic or composites for stiffness and light weight. Straps or (as shown at 136) a short harness 136 that extends under the arms of the wearer may be used to hold the shoulder support 114 firmly in place on the shoulders of the wearer.

It will be observed that the left linkage lower R link 126A and linkage lower R link 126C extend to the rear of the wearer 102. Also, the head platform 110 is affixed behind the head of the wearer 102. The center linkage lower R link 126B can project rearwardly or to the side as shown. Both keep the center linkage 106B out of the view of the wearer but the latter configuration keeps the center linkage 106B in a more compact arrangement.

It will also be observed that the left linkage lower R link 126A, center linkage lower R link 126B, and linkage lower R link 126C are all bent (in embodiments the could be curved) such that the axis of the left linkage lower R joint 122A intersects with the axis of the left linkage upper R joint 124A, the axes of the center linkage lower R joint 122B intersects with the axis of the center linkage upper R joint 124B, and the axes of the right linkage lower R joint 122C intersects with the axis of the right linkage upper R joint 124C. These points of intersection are labeled C1, C2, and C3 for the left linkage 106A, center linkage 106B, and right linkage 106C. Points A1, A2, and A3 represent the positions of the where spherical joints 130A, 130B, and 130C, respectively.

The configuration accommodates coupled translation and rotation of the head with a motion that depends on the positions of the points of intersection relative to the shoulder platform 105. Each of the where spherical joints 130A, 130B, and 130C remains a fixed distance from the position of a respective one of the three points of intersection C1, C2, and C3. In the optimization, the positions of the points of intersection C1, C2, and C3 are optimized.

Figure 8:
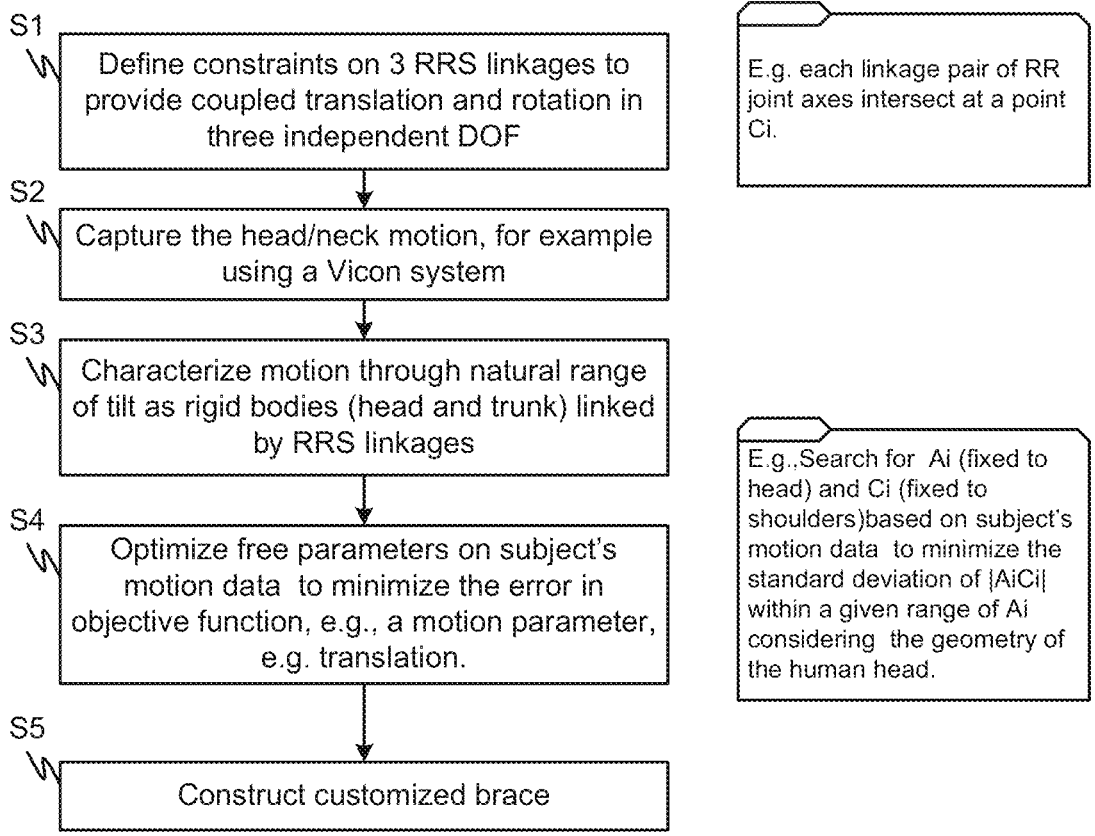
FIG. 8 shows a procedure for optimizing the kinematic mechanism to permit the optimal mapping of six degrees of freedom to the three degrees of the described kinematic mechanism.

After the constraints are specified as indicated at S1 in FIG. 8, to perform the optimization, a Vicon system was used to capture the motion of the head relative to the shoulders through various motions including lateral tilt, forward and backward tilt, and rotation S2, S3. It was found through experiment that under the constraints specified above, this motion could be substantially accommodated with three degrees of freedom of coupled translation and rotation. As disclosed below, the system may be modified to provide further freedom for, for example, head translation, by adding 3 DOF by means of sliding joints or actuators.

Figure 5A:
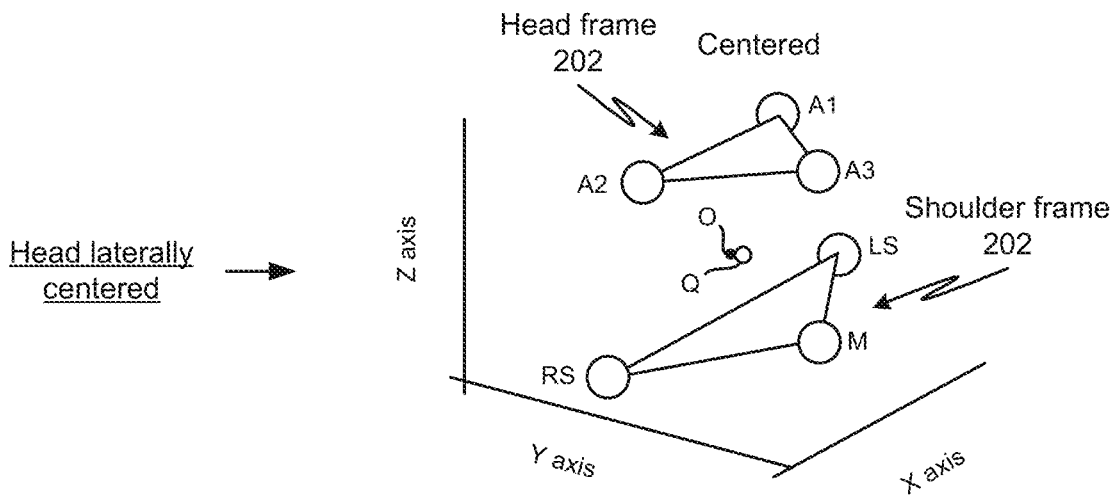
FIGS. 5A through 5C show schematically the markers following the lateral rotation of the head with tracking of the head estimated center of rotation and a point fixed relative to the head frame to acquire the displacement relative to the estimated center of rotation.
Figure 5B:
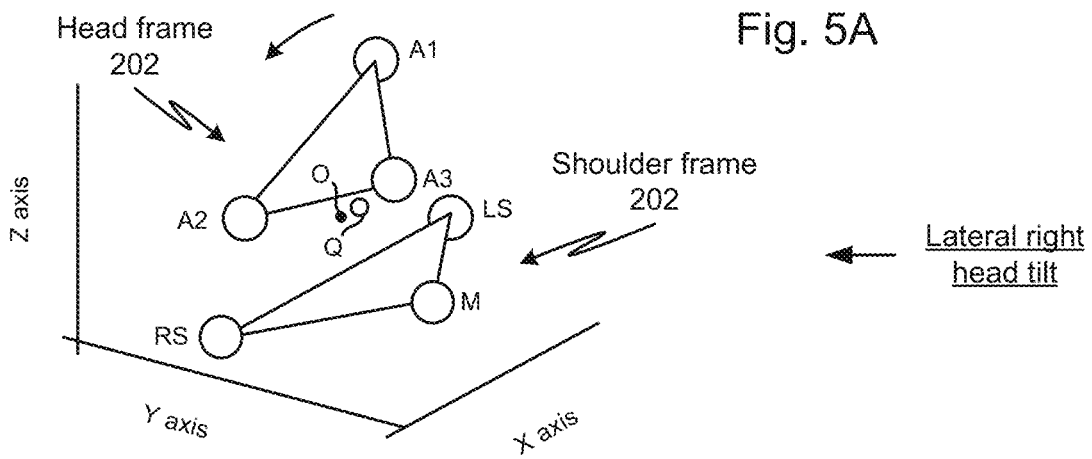
Figure 5C:
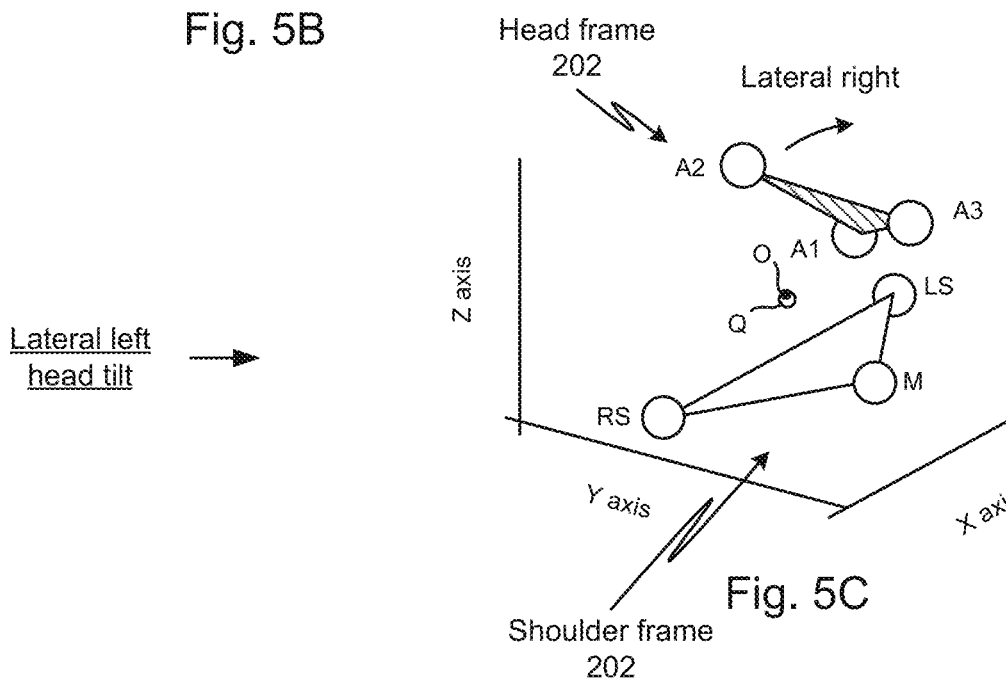
Figure 13:
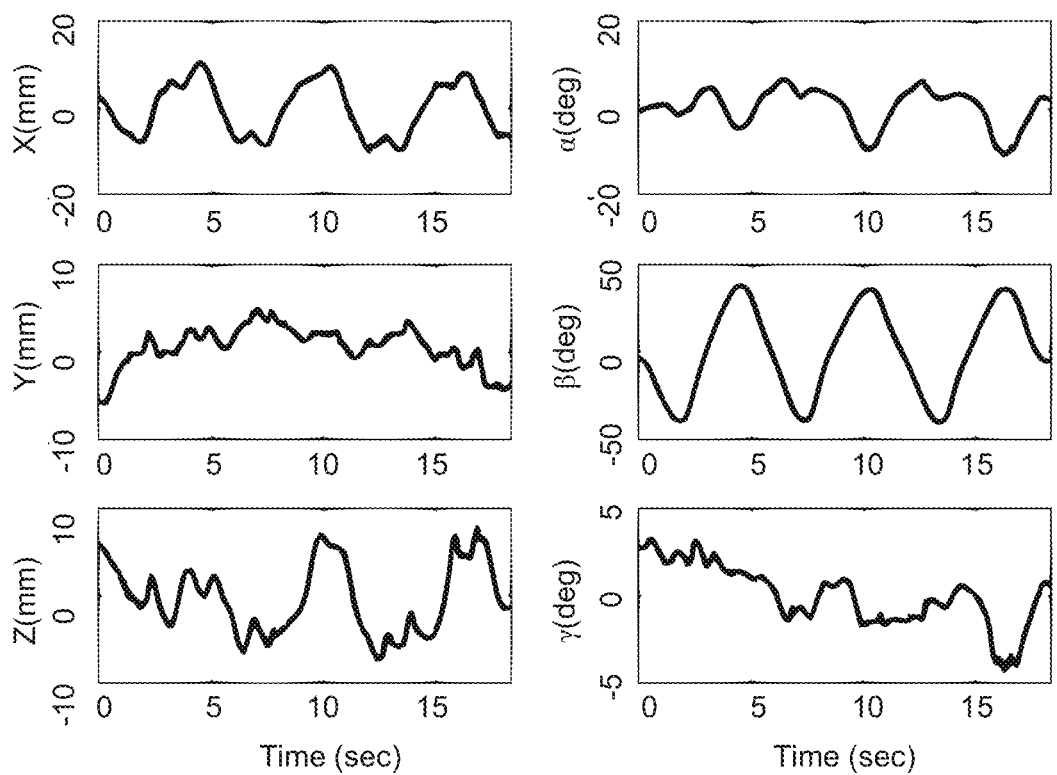
FIG. 13 shows an example data set indicating the position and orientation of the head and trunk of a subject during lateral bending.

Markers were placed on a subject's head and shoulders as shown in FIG. 13 and motion captured using the Vicon system. FIGS. 5A through 5C illustrate the movement of the head whose angle and position are defined by points A1 (right), A2 (middle or center), A3 (left), relative to the shoulders whose position is defined by points LS (left), RS (right), and M (center, or Middle). For illustration purposes, although the head was put through many other positions, FIG. 5A shows the head centered and FIGS. 5B and 5C show the head tilted laterally to the right and laterally to the left, respectively. Also indicated is a point O representing an estimated center of rotation of the head. This latter point is fixed relative to the shoulders. An actual effective point of rotation Q (a representative point fixed on the head frame, which is along the inward normal through the center of the head frame (A1, A2, A3) with a fixed length. The model represented by FIGS. 5A through 5C is sampled through a variety of head positions and the locations of the three points of intersection C1, C2, and C3 are optimized with the objective function being the minimization of the translation error between the points O and Q S4 which are shown vs. time in FIG. 13. To modify the positions of C1, C2, and C3 the sizes and shapes of the links and positions of the first R joint (base Bi) are varied in the model. The attachment points Ai on the head and intersection points Ci, together define the spherical motion of frame A1, A2, A3 relative to frame C1, C2, C3.

Procedurally, the optimization searches for Ai (fixed to head) and Ci (fixed to shoulders) based on subject's motion data that minimizes the standard deviation of |AiCi| within a given range of Ai with consideration of the geometry of the human head. Then the above-noted geometric parameters are optimized. Again, the objective function minimizes translation errors between the motion capture data and the end-effector data calculated by the mathematical model. The search range for each parameter is limited with consideration of human geometry. The optimization method selects a set of parameters and checks the desired range of rotation. If the configuration passes the range of rotation test, inverse kinematics is run by feeding recorded rotation data and the error mismatch in translation is calculated. The process is completed when the optimal parameters that minimize translation errors are found.

Starting with an architecture of a 3 DOF spherical mechanism, the configuration is modified so that it can perform the coupled translational and rotational motion observed during the motion of head and neck. It has been shown that if there exist three distinct and non-collinear points on a rigid body which move on three concentric spheres, the entire body must perform a spherical motion about the common center. However, if the motion is such that the three distinct and non-collinear points in the body move on non-concentric spheres, the rotation and the translation of the rigid body will be coupled.

The basic kinematic mechanism has some resemblance to a spherical mechanism composed of three RRS chains. Unlike this spherical mechanism, where all its six revolute axes intersect at a point, in the proposed mechanism the two revolute joints within each chain intersect at a point, as shown herein. Advantages of the design include (i) a parallel mechanism allows a designer to place smaller actuators on the base frame to reduce the moving inertia; (ii) RRS chains are easy to realize with light weight; (iii) from a fabrication perspective, it is easier to ensure that two successive revolute joints in a chain have a common intersection point rather than having an intersection point from three different chains. In the extreme case, when the intersecting points of the axes of each chain are the same, the system will yield spherical motion of the end-effector.

Figure 6:
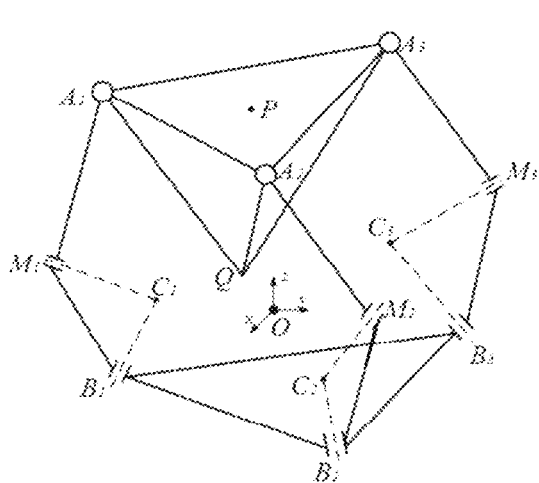
FIG. 6 illustrates the mathematical model of the kinematic mechanism showing constraints in the form of intersecting R joint axes for each RRS linkage.
Figure 7:
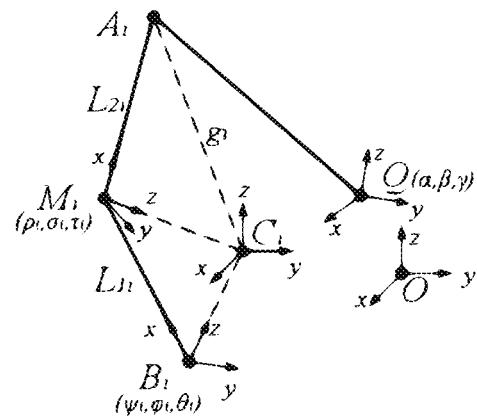
FIG. 7 shows the loop closure for a single RRS chain in respective variations.

Referring to FIGS. 6 and 7, a design problem associated with the disclosed kinematic solution may be stated as follow. Given the orientation of the end-effector, defined by a Body 3-2-3 sequence (i.e. Z-Y-Z sequence) of angles $[\alpha,\beta,\gamma]$, find the translation of the origin of the end-effector frame given by $[x_Q, y_Q, z_Q]$ relative to the base frame $\mathscr{F}_O$ and three joint angles $\theta_i$ at the base, where i=1,2,3.

Referring to FIGS. 6 and 7 show the 3-RRS parallel mechanism schematically. Point O is the center of the inertial frame. $B_1$, $B_2$ and $B_3$ form the base and $A_1$, $A_2$, $A_3$, Q form the end-effector. The connection of the end-effector to the base is through three RRS joints in each chain. The R joints pass respectively through $B_i$, $M_i$ and the S joint passes through $A_i$. The revolute joint axes of a chain intersect at a point $C_i$, where i=1,2,3. The point $C_i$ stays fixed during motion. FIG. 7 shows the coordinate convention of a chain of the 3-RRS mechanism. End-effector frame $\mathscr{F}_Q$ has its origin at point Q and its orientation is given by $[\alpha,\beta,\gamma]$ in a Body 3-2-3 sequence. The base frame has its origin at $C_i$ and is fixed and aligned parallel to the global frame $\mathscr{F}_O$. The frame of lower link $\mathscr{F}_{B_i}$ is centered at $B_i$ and the frame of upper link $\mathscr{F}_{M_i}$ is centered at $M_i$ whose z axes both intersect at point $C_i$. The orientation of both link frames are represented by $[\psi,\phi,\theta]$ and $[\rho,\sigma,\tau]$ defined in a Body 3-2-3 sequence, respectively, in which the third angles denote the rotation angle of the corresponding revolute joint. The lengths of the lower and upper links of each chain are denoted by $L_{1i}$ and $L_{2i}$, respectively. The constant distance between point $A_i$ and $C_i$ is denoted as $g_i$. The revolute joints in each chain can be located anywhere along its axis, thus the joint axes can be chosen such that $B_iC_i$ is perpendicular to $B_iM_i$ and $A_iM_i$ is perpendicular to $C_iM_i$ for modeling purposes.

Note that the terms "end-effecter" and "platform" are interchangeable in the context of the instant specification and claims.

The point $C_i$ is stationary in the global frame $\mathcal{F}_O$ denoted as $$^{\mathcal{F}_O}r_{OC_i} = [x_{Ci} \quad y_{Ci} \quad z_{Ci}]^T.$$

The position vector of point $A_i$ in frame can be determined using a vector equation $OA_i = OQ + QA_i$, i.e.

$$^{\mathcal{F}_O}r_{OA_i} = {^{\mathcal{F}_O}r_{OQ}} + {^OR_Q}\,^{\mathcal{F}_Q}r_{QA_i},\ i = 1, 2, 3 \quad (1)$$

where (s and c are short for sin and cos, respectively), $$^{\mathcal{F}_O}r_{OA_i} = [x_{Ai} \quad y_{Ai} \quad z_{Ai}]^T,$$

$$^{\mathcal{F}_O}r_{OQ} = [x_Q \quad y_Q \quad z_Q]^T,$$

$$^OR_Q = \begin{bmatrix} c\alpha c\beta c\gamma - s\alpha s\gamma & -c\alpha c\beta s\gamma - s\alpha s\gamma & c\alpha s\beta \\ s\alpha c\beta c\gamma + c\alpha s\gamma & -s\alpha c\beta s\gamma + c\alpha s\gamma & s\alpha s\beta \\ -s\beta c\gamma & s\beta s\gamma & c\beta \end{bmatrix},$$

$$^{\mathcal{F}_Q}r_{QA_i} = [{^Q}x_{Ai} \quad {^Q}y_{Ai} \quad {^Q}z_{Ai}]^T.$$

The distance $\|A_iC_i\| = g_i$ is fixed in each chain, then the system of equations can be formulated as follows, $$g_i^2 \|{^{\mathcal{F}_O}r_{OA_i}} - {^{\mathcal{F}_O}r_{OC_i}}\|_2^2,\ i = 1, 2, 3 \quad (2)$$

On substituting Equation (1) into (2), one gets three quadratic equations involving $x_Q$, $y_Q$, and $z_Q$, $$(a_{i1} + x_Q)^2 + (a_{i2} + y_Q)^2 + (a_{i3} + z_Q)^2 = g_i^2,\ i = 1, 2, 3 \quad (3)$$

where, $$\vec{a_i} = [a_{i1} \quad a_{i2} \quad a_{i3}]^T$$
$$= {^OR_Q}\,^{\mathcal{F}_O}r_{QA_i} - {^{\mathcal{F}_O}r_{OC_i}}$$

$a_i$ is a known quantity provided that the orientation of the end-effecter is given. Upon manipulating the three component equations of Equation (3), a single second-order polynomial can be obtained in one variable, namely $z_Q$. Thus, two roots of $z_Q$ can be found and the position of point $Q$ in frame $\mathcal{F}_O$, $[x_Q\ y_Q\ z_Q]^T$, can be solved accordingly using the remaining two component equations. The position of $A_i$ in frame $\mathcal{F}_O$ can then be obtained using Equation (1).

Once the position of $Q$ in frame $\mathcal{F}_O$ is found, the way of solving for joint angle $\theta_i$ is almost the same as the method introduced in. The length of the upper link $\|A_iM_i\|_2^2 = L_{2i}^2$ can be used to solve for each joint angle $\theta_i$. The position of each lower revolute joint $B_i$ is also fixed in the frame $\mathcal{F}_O$, and can be denoted as $$^{\mathcal{F}_O}r_{OB_i} = [x_{Bi} \quad y_{Bi} \quad z_{Bi}]^T.$$

Then, the position of each middle revolute joint $M_i$ in frame $\mathcal{F}_O$ can be expressed as, $$^{\mathcal{F}_O}r_{OM_i} = {^{\mathcal{F}_O}r_{OB_i}} + {^OR_{C_i}}\,{^{C_i}R_{B_i}}\,^{\mathcal{F}_{B_i}}r_{B_iM_i},\ i = 1, 2, 3 \quad (4)$$

where, $^OR_{C_i} = 3 \times 3$ identity matrix, $$^{C_i}R_{B_i} = \begin{bmatrix} c\psi_i c\phi_i c\theta_i - s\psi_i s\theta_i & -c\psi_i c\phi_i s\theta_i - s\psi_i c\theta_i & c\psi_i s\phi_i c \\ s\psi_i c\phi_i c\theta_i + c\psi_i s\theta_i & -s\psi_i c\phi_i s\theta_i + c\psi_i c\theta_i & s\psi_i s\phi_i \\ -s\phi_i c\theta_i & s\phi_i s\theta_i & c\phi_i \end{bmatrix},$$

$$^{\mathcal{F}_{B_i}}r_{B_iM_i} = [L_{1i} \quad 0 \quad 0]^T.$$

Thus, the system equations can be formulated as follows.

$$L_{2i}^2 = \|{^{\mathcal{F}_O}r_{OM_i}} - {^{\mathcal{F}_O}r_{OA_i}}\|_2^2,\ i = 1, 2, 3 \quad (5)$$

Substituting Equation (4) and the position of $A_i$ in frame $\mathcal{F}_O$ into Equation (5) leaves only the joint angle $\theta_i$'s as the unknowns. For each chain, Equation (5) yields a quadratic equation and admits two possible solutions for the position of $M_i$ in frame $\mathcal{F}_O$. It admits at most eight real solutions for a given position $Q$ in frame $\mathcal{F}_O$ and thus the inverse kinematics admits up to sixteen real solutions.

The forward kinematics for this system is defined as follows: Given a set of joint angles $\theta_i$ and the position is solve-for, denoted as $[x_Q, y_Q, z_Q]$, and orientation, $[\alpha, \beta, \gamma]$ defined by a Body 3-2-3 sequence (i.e. Z-Y-Z sequence) of the end-effecter. The disclosed subject matter presents a numerical approach to the solution.

In addition to Equation (1), the position vector of point $A_i$ in frame $\mathcal{F}_O$ can be expressed by, $$^{\mathcal{F}_O}r_{OA_i} = {^{\mathcal{F}_O}r_{OM_i}} + {^OR_{C_i}}\,{^{C_i}R_{M_i}}\,^{\mathcal{F}_{M_i}}r_{M_iA_i} \quad (6)$$

where, $$^{C_i}R_{M_i} = \begin{bmatrix} c\rho_i c\rho_i c\tau_i - s\rho_i s\tau_i & -c\rho_i c\sigma_i s\tau_i - s\rho_i c\tau_i & c\rho_i s\sigma_i \\ s\rho_i c\sigma_i c\tau_i + c\rho_i s\sigma_i & -s\rho_i c\sigma_i s\tau_i + c\rho_i c\tau_i & s\rho_i s\sigma_i \\ -s\sigma_i c\tau_i & s\sigma_i s\tau_i & c\sigma_i \end{bmatrix},$$

$$^{M_i}A_i = [L_{2i} \quad 0 \quad 0]^T.$$

Substituting Equations (1) and (4) in (6), a vector equation of loop closure for each chain can be obtained, $$^{\mathcal{F}_O}r_{OQ} + {^O}R_Q{}^{\mathcal{F}_Q}r_{QA_i} = \quad (7)$$
$$^{\mathcal{F}_O}r_{OB_i} + {^O}R_{C_i}{}^{C_i}R_{B_i}{}^{\mathcal{F}_{B_i}}r_{B_iM_i} + {^O}R_{C_i}{}^{C_i}R_{M_i}{}^{\mathcal{F}_{M_i}}r_{M_iA_i}$$

The variables in this equation are the position of the end-effecter, $x_Q$, $y_Q$, and $z_Q$, the orientation of the end-effecter, $\alpha$, $\beta$, and $\gamma$, the angle of the lower revolute joint, $\theta_i$, and the angle of the upper revolute joint $\tau_i$. Since there are three chains, one obtains nine scalar equations with twelve variables. In forward kinematics, the inputs are the joint angle $\theta_i$, i=1,2,3, and thus nine scalar equations (i.e. three vector equations) can be used to solve for nine unknown variables. One can simplify the equations by expressing the rotation matrices differently. Using Cayley's formula, $$^{O}R_Q = \frac{1}{1+p_1^2+p_2^2+p_3^2} \cdot \quad (8)$$
$$\begin{bmatrix} 1+p_1^2-p_2^2-p_3^2 & 2(p_1p_2-p_3) & 2(p_3p_1+p_2) \\ 2(p_1p_2+p_3) & 1+p_2^2-p_3^2-p_1^2 & 2(p_2p_3-p_1) \\ 2(p_3p_1-p_2) & 2(p_2p_3+p_1) & 1+p_3^2-p_1^2-p_2^2 \end{bmatrix},$$

Using tangent half-angle formula, $$^{C_i}R_{M_i} = \frac{1}{1+t_i^2} \cdot \begin{bmatrix} d_{i1}(1-t_i^2)+e_{i1}(2t_i) & d_{i4}(1-t_i^2)+e_{i4}(2t_i) & f_{i1} \\ d_{i2}(1-t_i^2)+e_{i2}(2t_i) & d_{i5}(1-t_i^2)+e_{i5}(2t_i) & f_{i2} \\ d_{i3}(1-t_i^2) & e_{i6}(2t_i) & f_{i3} \end{bmatrix}, \quad (9)$$

where $$t_i = \tan\left(\frac{\tau_i}{2}\right),$$

and $d_{ij}$, $e_{ij}$, $f_{ij}$ are known constants involving $\psi_i$ and $\phi_i$, i=1,2,3.

Additionally, by grouping other constants and substituting Equations (8) and (9), Equation (7) becomes $$t_i + d_i = \mathbb{P} \cdot e_i + x, i=1,2,3 \quad (10)$$

where, $$t_i = \frac{L_{2i}}{1+t_i^2} \cdot \begin{bmatrix} d_{i1}(1-t_i^2)+e_{i1}(2t_i) \\ d_{i2}(1-t_i^2)+e_{i2}(2t_i) \\ d_{i3}(1-t_i^2) \end{bmatrix},$$

$$d_i = {^{\mathcal{F}_O}}r_{OB_i} + {^O}R_{C_i}{}^{C_i}R_{B_i}{}^{\mathcal{F}_{B_i}}r_{B_iM_i},$$

$$\mathbb{P} = {^O}R_Q,$$

$$e_i = {^{\mathcal{F}_Q}}r_{QA_i},$$

$$x = [x_Q \ y_Q \ z_Q]^T,$$

where $d_i$ and $e_i$ are known constants and the variables are in the terms of $t_i$, x and P. The nine scalar equations in Equation (10) can be further simplified into three quadratic equations involving $t_1$, $t_2$ and $t_3$ by eliminating x and P. However, it is impossible to simplify them into a single polynomial equation in a single variable.

A numerical approach is used with fsolve as the numerical solver. For a real-time application, the initial guess is selected to be the configuration of the brace from the last time step so that it converges to the current brace configuration with a short computing time.

Figure 9:
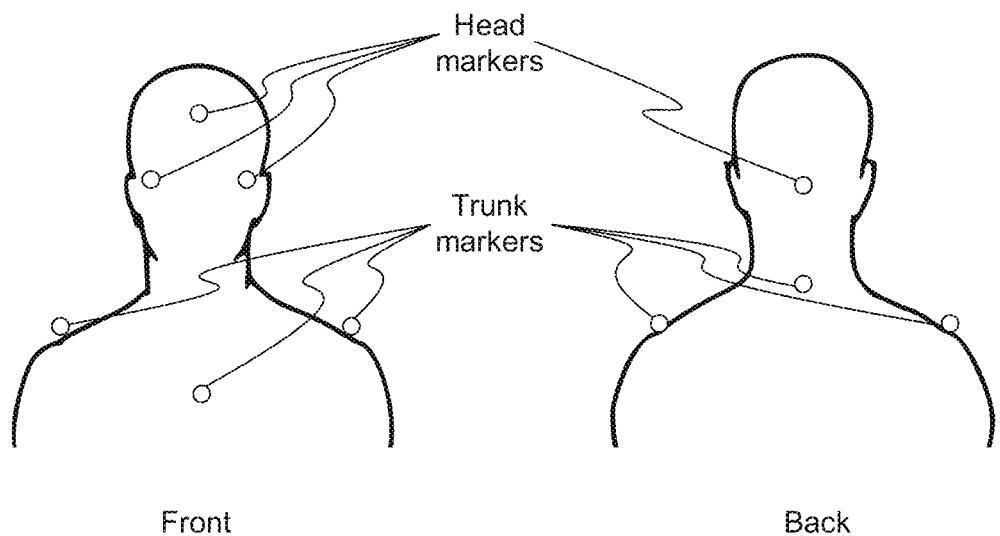
FIG. 9 shows marker placement for characterization of the head and shoulder relative movement using VICON system.

The brace was designed based on measured anthropometric parameters and head/neck kinematics data of one person. A laboratory based motion capture system from VICON was used with ten infrared cameras. It was used to record the person's natural head motion. Eight infrared markers were placed on the trunk and the head of the person, as shown in FIG. 9. A static trial was performed first when the person was sitting upright on a stationary stool, in order to obtain the relative positions of the markers. Four head/neck motions were recorded, including flexion/extension, lateral bending, axial rotation and a more general rolling motion. The first three motions are single plane rotations and are intended to record the person's ranges of rotation of the head. The last motion is a spatial rotation which combines both flexion and bending of the head.

Figure 10:
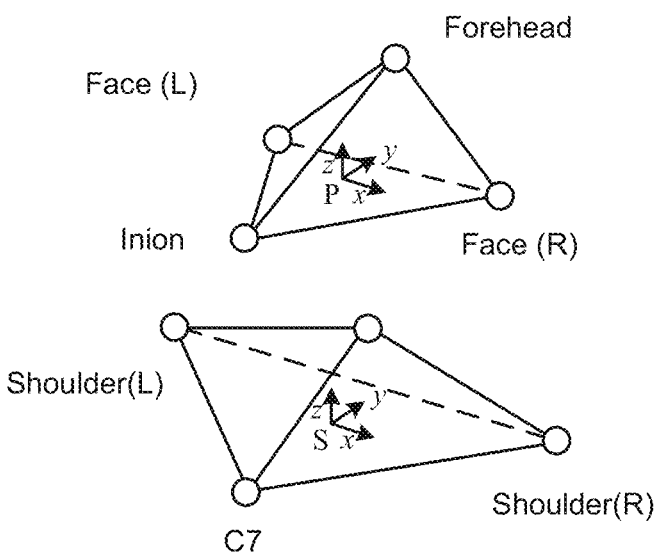
FIG. 10 shows the local coordinate system corresponding to the characterization of FIG. 10.

The camera system recorded the motion of the markers. They were used to construct two rigid bodies, the trunk and the head. The local coordinate systems are shown in FIG. 10. The origin of the trunk frame is the center of the left and right shoulder markers, with the x-axis directed from the left to the right. The origin of the head frame is set as the geometric center of the triangle formed by the left cheek, the right cheek and the inion markers, with the x-axis pointing from the left cheek marker to the right cheek marker. FIG. 13 shows an example dataset of the position of a fixed point on the head frame and the head orientation represented by the Body 3-2-3 (Z-Y-Z) sequence during lateral bending of this person. These kinematic data are interpreted as indicating that natural head motion can be characterized as couple spatial rotation and translation.

The recorded marker kinematics represent the head/neck motion relative to the trunk. The human head has six DOFs, hence only three independent motions can be precisely satisfied with the proposed 3 DOF mechanism while the remaining motions are determined by the articulated structure. Due to the large range of rotation as compared to the small translations of the head, the three independent variables selected are the three rotations. Thus, the goal of the optimization is to find a set of geometric parameters for constructing a brace to accommodate the head rotations while minimizing its translational errors relative to the trunk.

From the perspective of the design, the aesthetic is considered as the brace should not obstruct the line of sight of the user. Hence, the attachment points are on the back and the side of the human body. Additionally, the design is intended to be symmetric about the sagittal plane, resulting in fewer parameters to be optimized.

In order to impose these design conditions, three pairs of points were identified, i.e. $A_i$ and $C_i$ where i=1,2,3. Out of these, $A_i$ is a fixed point in the moving (head) frame and $C_i$ is a fixed point in the static (trunk) frame, and the distance between $A_i$ and $C_i$ remains constant during the recorded motion of the head. Because fewer DOFs are allowed by the mechanism, however, it is difficult to analytically find such point pairs in the two frames based on the recorded data. Instead, each point pair is found numerically such that the distance between the two varies minimally during the recorded motion. A two-loop numerical approach is used. In the outer loop, a possible location of $A_i$ is randomly selected in the moving frame $^\mathscr{F}Q$ within a search range. The location of $C_i$ fixed in the static frame $^\mathscr{F}O$ is searched in the inner loop such that the deviation of the distance between the two points, $A_i$ and $C_i$, is minimized. After a certain numbers of iterations of searching $A_i$ in $^\mathscr{F}Q$, the point pair $A_i$ and $C_i$ in a chain is finalized, which has the lowest distance deviation between the two points among all iterations. The fminsearch in Matlab was used to perform this optimization.

Once the positions $A_i$'s and $C_i$'s are determined, the geometric parameters are optimized, e.g., the locations of $B_i$'s, the lengths $L_{1i}$'s and $L_{2i}$'s. The goal is to minimize the overall translational error of a fixed point in the head frame (point Q in FIGS. 6, 7) between the recorded head motion and the computed one using the inverse kinematics, while also maintaining reasonable ranges of rotations of the end-effector.

Figure 15A:
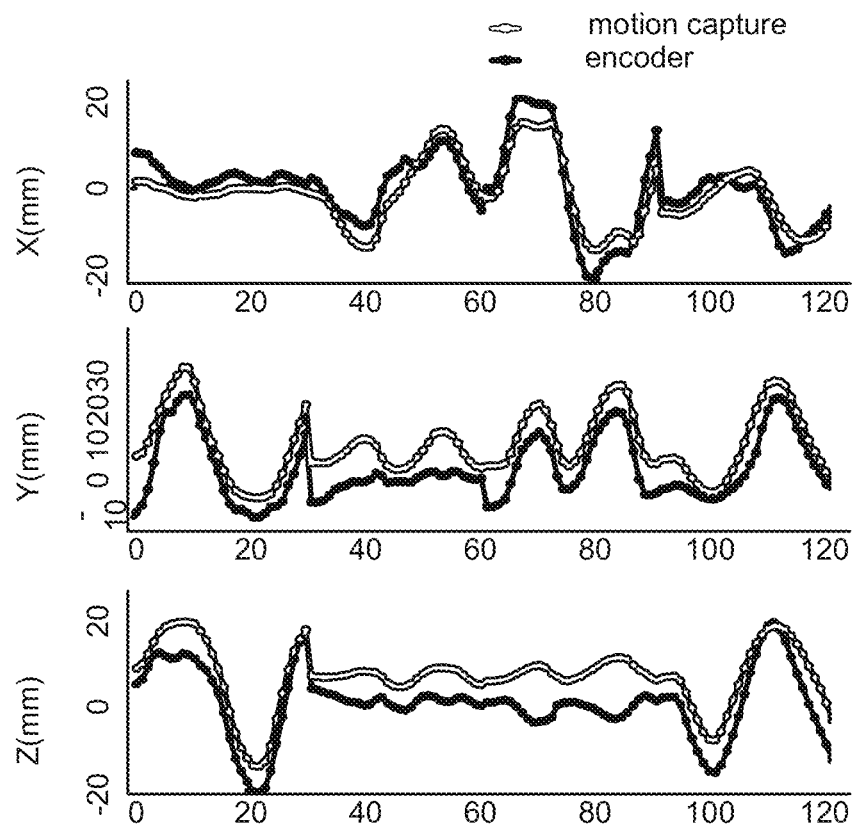
FIG. 15A shows the recorded translations of human head and the computed translations from encoder signals from the optimized brace.
Figure 15B:
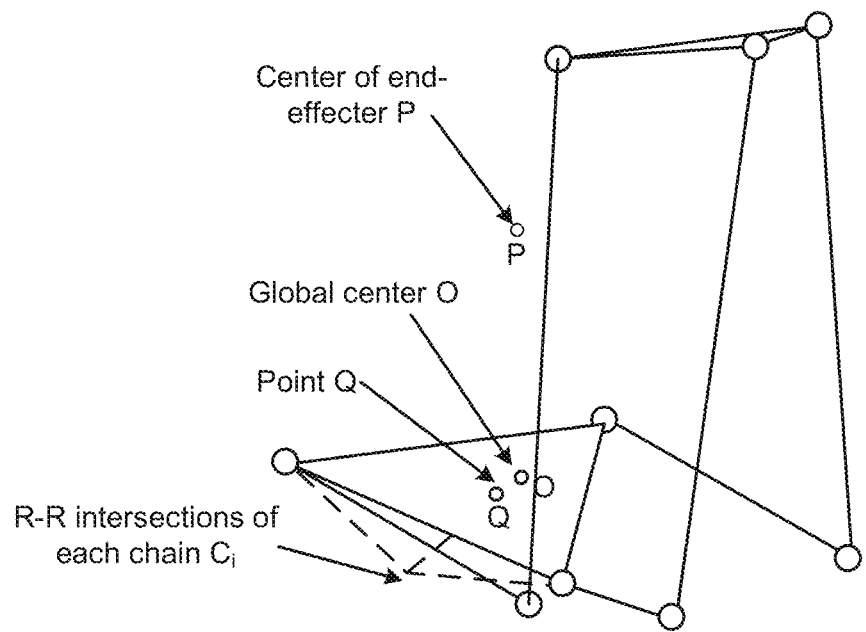
FIG. 15B shows a simulation model of a brace with optimized parameters.
Figure 16A:
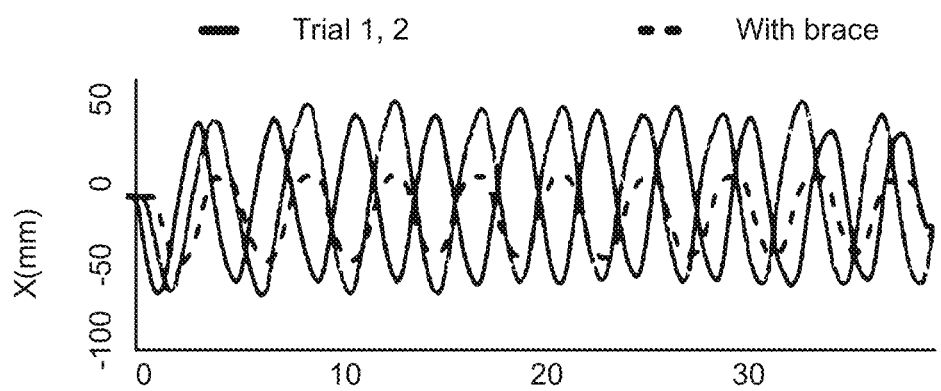
FIGS. 16A through 16E represent data for a representative head position of one participant performing head flexion/extension in three trials.
Figure 16B:
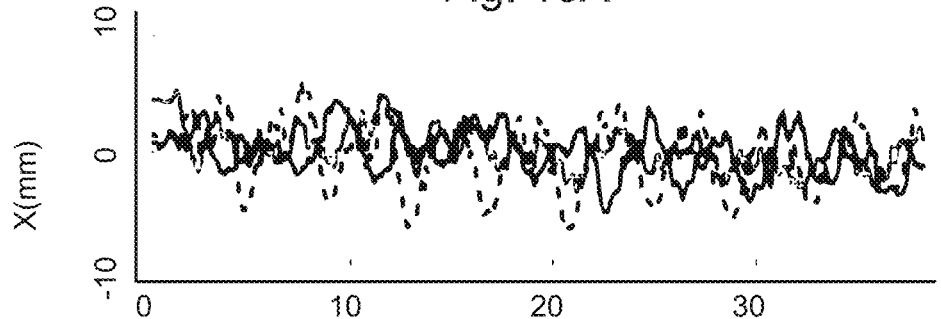
Figure 16C:
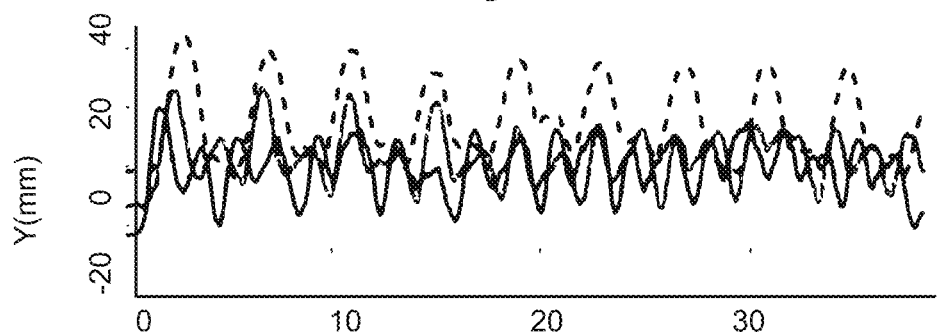
Figure 16D:
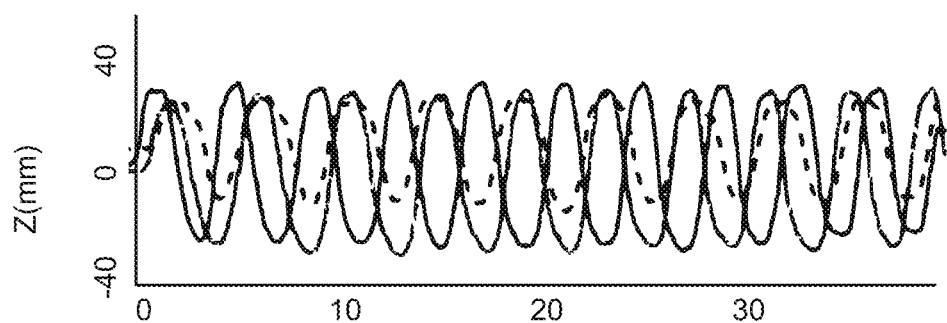
Figure 16E:
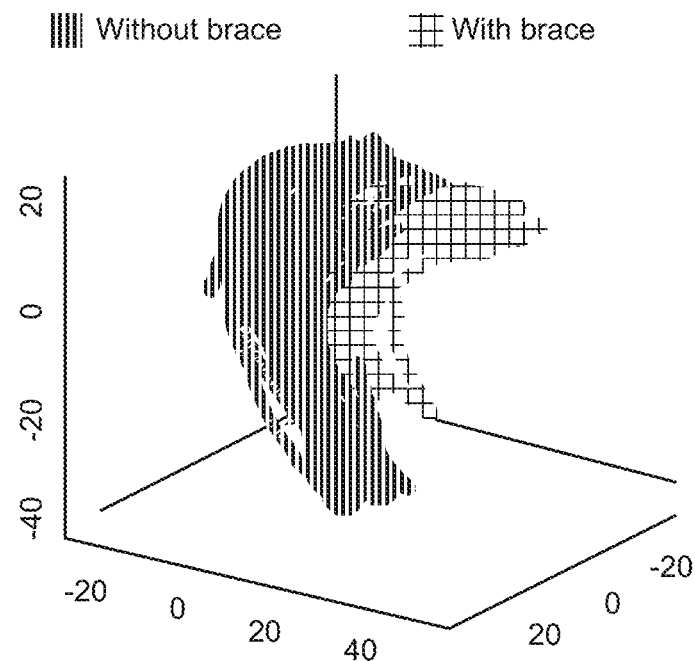

The first optimization runs for 10,000 cases and the second one runs for 1,000 cases. These simulations were computed on a lab-based desktop (Intel CPU @ 3.40 GHz and 16 GB RAM) and took about six hours to finish. For the simulation model with the selected parameters, as shown in FIGS. 15A and 15B, the intersecting points $C_i$ do not coincide and therefore the end-effector both rotates and translates. The overall translational errors for all four motions of the optimal design are: x=1.3±3.5 mm y=6.0±2.9 mm and z=−5.8±2.7 mm. The optimal design maintains the ranges of rotation of +45/−30 in mid-sagittal plane, ±35 in frontal plane and ±65 in horizontal plane.

The simulation results show that it is possible to design a brace using the proposed mechanism to obtain relatively large ranges of head rotations while have small translational motion. Because all the legs are placed at the back and side of the neck of the human body, the range of rotation is smaller in backward extension compared to forward flexion. The lateral bending and the axial rotation show symmetric ranges of rotation given that the simulation model does not take into account the interference between mechanical components.

FIG. 15B shows the simulation model with optimal parameters. FIG. 15A shows the recorded translations of human head (blue) and the computed translations of the optimized brace (red) along three axes. Epochs of 30 seconds represent one type of motion: (1-30) sagittal plane flexion/extension; (31-60) mediolateral bending; (61-90) axial rotation; (91-120) rolling motion.

The disclosed embodiments, as shown in the various figures, conform to the simulation model (excepting differences relating the 6DOF design discussed below which is the same when the linear actuators are fixed). In the tested embodiment, two straps are used to secure the shoulder pads to the user's trunk. A belt is used to tighten the headband on the user (this belt is not shown in the drawings but extends across the forehead) and minimize sliding between the head and the brace. Additional paddings made of polyethylene are filled in the areas contacting the human skin. Most of the parts are 3D printed and the entire prototype weighs 1.0 kg (about ⅕ of the weight of an adult's head). The fixed part of the brace (shoulder interface) may be strapped on the shoulders using Velcro while the end-effector (head interface) may strapped to the head from the back with a small adjustable strap wrapping over the front. The choice of mounting of the head strap may avoid obstructions in the field of view of the user and minimize the risk of choking of the patients, as happens often with conventional neck braces, with support under the chin. The configuration may be substantially symmetric about the sagittal plane to minimize the parameters of the brace to be optimized. Two intersecting joint axes in each leg of the mechanism can be easily ensured during fabrication and the overall mechanism can be assembled using the information of points C1, C2, C3. In contrast, a purely spherical mechanism may be such that the joint axes from the three legs would be required to intersect at a common center.

Figure 11:
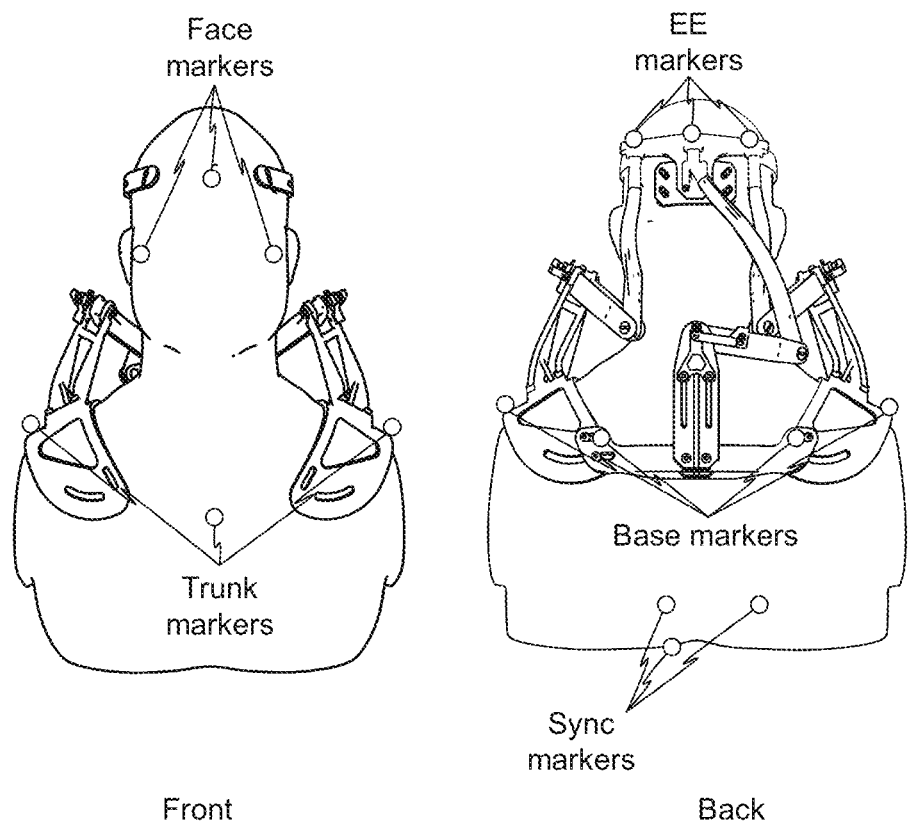
FIGS. 11 and 12 shows the placement of VICON markers and the local frames defined thereby.
Figure 12:
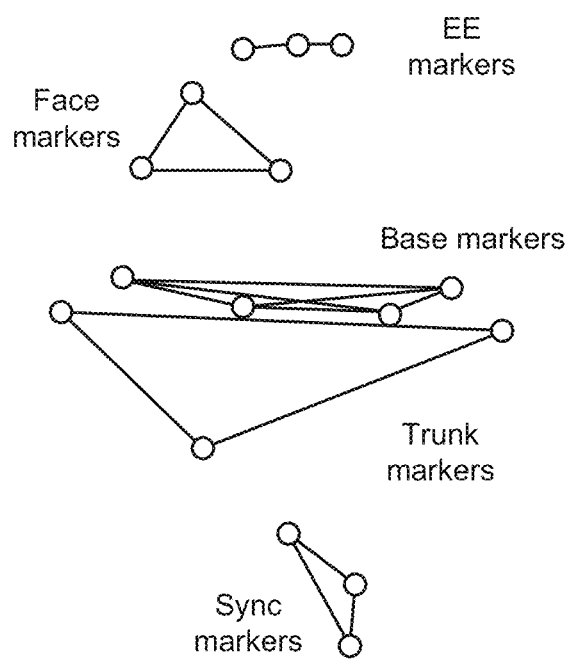
Figure 17:
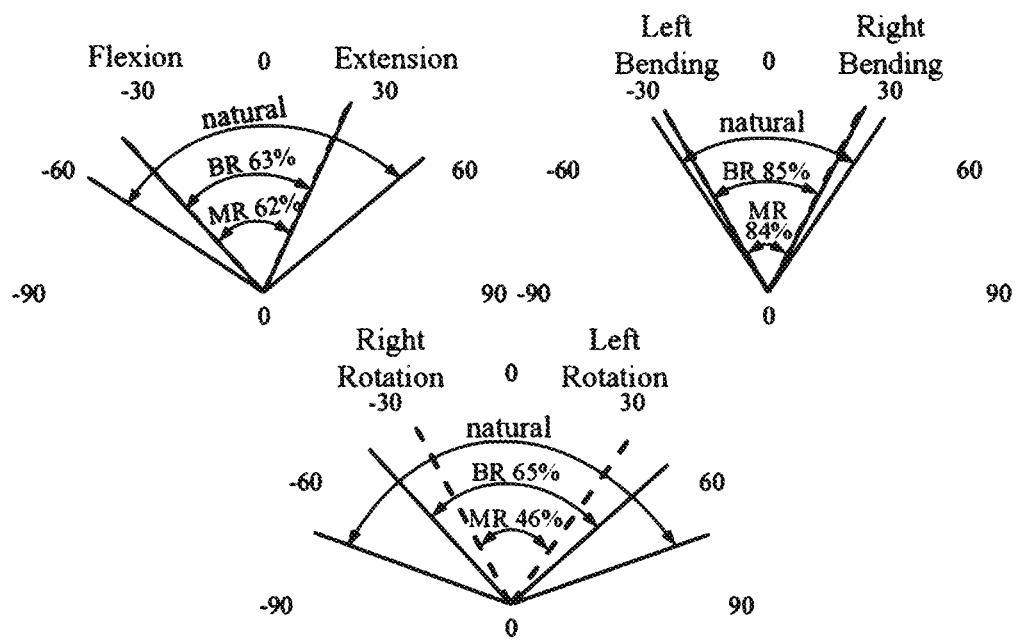
FIG. 17 shows average ranges of rotation in three planar motions, where the natural ranges are labeled between outer solid lines, the ranges allowed by the brace (BR) are shown between the inner solid lines solid red lines and the measurable ranges (MR) are labeled between two dashed black lines.

Referring to FIGS. 11, 12, and 17, an experiment was performed to evaluate the neck brace with 10 young healthy subjects to demonstrate range of rotation of the head, the way the head translates during typical head rotations, the accuracy of the computation of the position and orientation of the head using joint potentiometers on the brace, and whether slipping between the head and the brace is evident. The brace was not optimized to a specific user.

The Vicon motion capture system with infrared markers was used to record the motion of the end-effector of the brace relative to the upper trunk and motion of the head relative to the upper trunk. During the motion, time synchronization was made between the motion capture system and data acquisition module of the neck brace. The Vicon served as the reference standard for evaluating the accuracy of the measurement using the brace sensors. The experiment had three sessions, each comprised of a static trial followed by four dynamic movements: flexion/extension, lateral bending, axial rotation, general roll motion. The subjects performed each movement ten times at a self-selected speed. The subjects repeated these same motions with and without the brace. The camera system and the brace sampled the data at 100 Hz. The results from brace characterization were very positive and encouraging. The results for the first three questions are summarized in FIG. 17 and Tables 1 and 2.

It was observed that the brace allows between 60-80% of the natural range of motion in different planes. It was observed that the brace only slightly changes neck translation during head motion (Tables 1 and 2). The joint encoder data from the brace can be used to estimate the orientation/position of the head with a high accuracy when compared to the Vicon motion capture system (Tables 1 and 2). Sliding of the brace was observed only in extreme postures of the neck and the same brace can be used across subjects without introducing significant errors.

The motion of the head is measured using three potentiometers mounted on the lower revolute joints of the legs. The position and the orientation of the end-effector is computed by the forward kinematics, using these sensor data. The sensors are calibrated after assembling all mechanical components.

TABLE 1 deviation of translation of subject with brace vs. natural neck motion
AVERAGE PAIRWISE DEVIATION
OF NECK TRANSLATION OF SUBJECTS.

|  | Flexion/Extension | Bending | Rotation | Rolling |
| --- | --- | --- | --- | --- |
| Mean (cm) | 0.57 ± 0.30 | 1.07 ± 0.45 | 0.85 ± 0.31 | 1.16 ± 0.51 |

TABLE 2 calculation of end-effecter orientations based on the joint-encoder data indicating a few degrees' deviation from reference standard
AVERAGE OF THE MEAN AND THE RMS ERRORS OF THE BRACE MEASUREMENT OVER 10 SUBJECTS.

|  | Flexion/Extension | Bending | Rotation | Rolling |
| --- | --- | --- | --- | --- |
| Mean (deg) | 1.1 ± 2.5 | 2.5 ± 2.5 | 2.5 ± 2.9 | 3.6 ± 2.3 |
| RMS (deg) | 1.8 ± 2.9 | 3.1 ± 2.8 | 3.0 ± 3.0 | 4.9 ± 2.7 |

A human experiment was designed to evaluate the neck brace. Four questions were: (1) How does the range of rotation of the head change when wearing the brace? (2) How much translational error is there from the brace when maintaining the user's intended head rotation? (3) Is there relative movement between the head and the brace during the experiment? (4) How accurate is the computation of the position and orientation of the head using the inexpensive potentiometers? Questions (1)-(3) target at the wearability of the brace, while Question (4) addresses the accuracy of the brace measurement.

Ten subjects, as listed in Table 3, participated in this experiment.

TABLE 3

Information of Participants

|  | Mean | Standard Deviation | Range |
| --- | --- | --- | --- |
| Age (y) | 26.60 | 4.35 | 22-36 |
| Height (cm) | 177.20 | 6.29 | 166-186 |
| Weight (kg) | 73.67 | 15.64 | 60-112 |
| Shoulder Width (cm) | 35.38 | 1.68 | 31.8-37 |
| Shoulder Thickness (cm) | 12.45 | 1.71 | 10-16.5 |
| Neck Length (cm) | 13.15 | 1.18 | 11-15 |
| Neck Circumference (cm) | 35.91 | 3.77 | 31-42.5 |
| Forehead Circumference (cm) | 57.12 | 1.37 | 54.5-59.5 |

The same motion capture system was used to record the head kinematics which served as the gold standard for evaluating the accuracy of the measurement using the brace sensors. The experiment had three sessions, each composed of a static trial followed by four dynamic trials. In each dynamic trial, the subject was instructed to perform one type of head motion (introduced in section 3) continuously ten times at a self-selected speed. The procedures of these three sessions were nearly identical, except that the subject performed the head motions without wearing the brace in the first and the second session, but performed the motions with the brace in the last one.

During the experiment, each participant sat straight on a stationary stool within the range of the camera system. Infrared markers, as shown in FIG. 11, were placed on the trunk and the face to record the head motion relative to the shoulders. In addition to these body markers, seven markers were placed on the brace to record the brace movements during the experiment. The data recorded by both systems was synchronized via an infrared LED connected to the microcontroller of the brace, which sent an electronic trigger as soon as the brace was powered. When this LED was turned on, it could be recognized by the cameras and the brace was synchronized to record the joint angles and compute the orientation and the position of the head. The camera system and the brace were both sampled at 100 Hz.

Since the brace and the head motions were recorded separately through the body and brace markers, the relative movement (sliding) between the brace and the human head could be captured quantitatively. During the experiment with the brace, the position and the orientation of the end-effecter of the brace was computed by both the infrared markers using the camera system and the potentiometers installed on the three base joints of the brace. Thus, the accuracy of the brace measurement using on-board sensors was evaluated against the camera system.

Figure 18A:
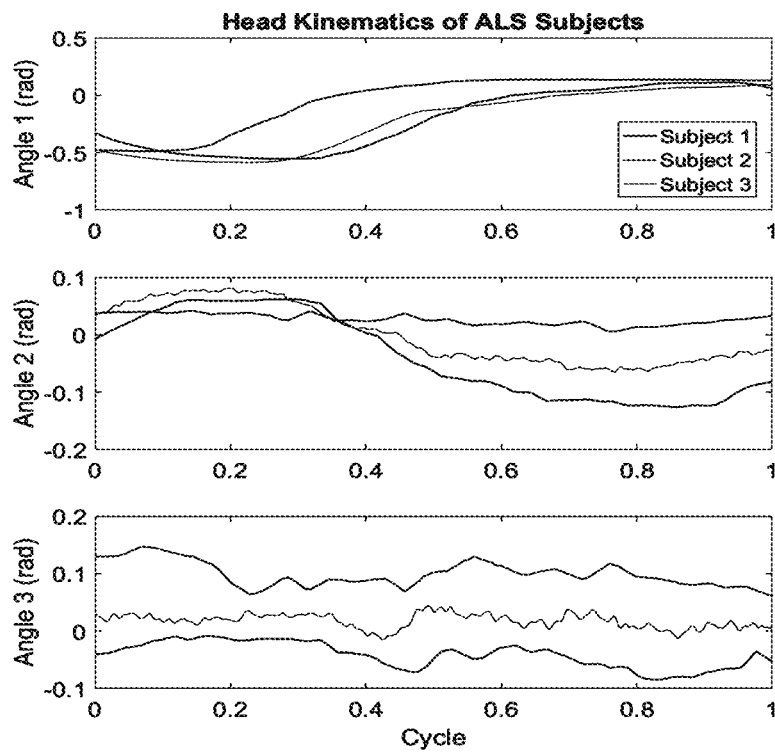
FIGS. 18A and 18B show data from experiments with an ALS patient wearing a brace according to disclosed embodiments.
Figure 18B:
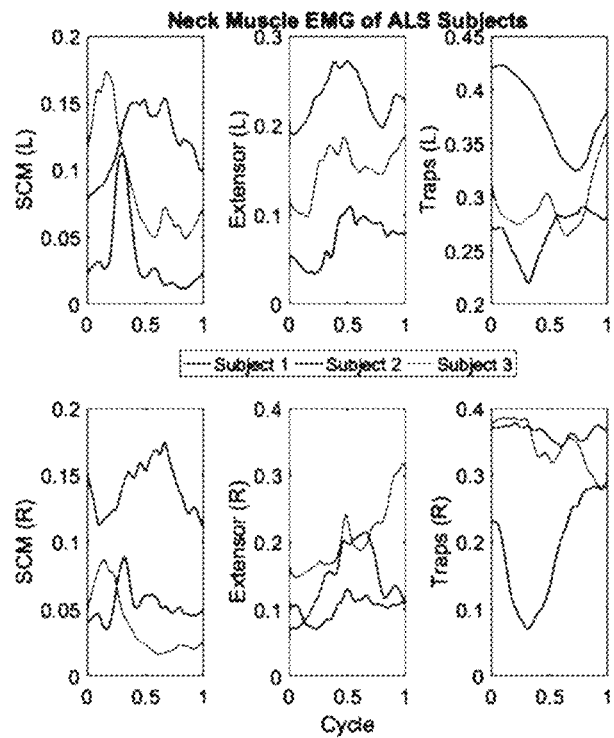
Figure 18C:
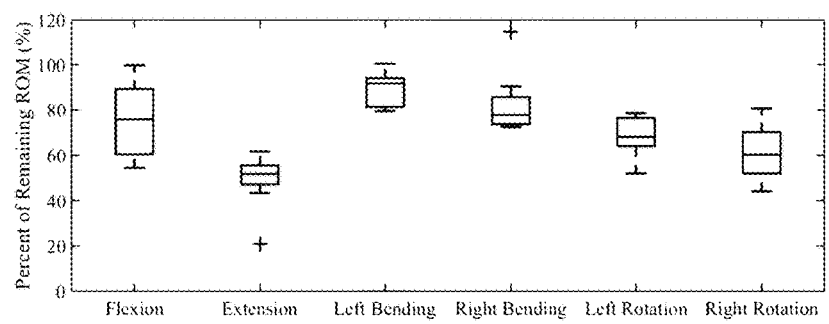
FIG. 18C shows a box plot indicating measured range of motion data for healthy individuals according to embodiments of the disclosed subject matter.

The range of the head rotations allowed by this brace among participants are: 77.9% in flexion, 53.1% in extension, 88.1% in left bending, 79.2% in right bending, 69.7% in left rotation and 60.8% in right rotation, as indicated in the box plot in FIG. 18C. Therefore, a person wearing this brace can roughly achieve overall 70% of his/her natural head rotations. The ranges of rotation of the brace for the lateral bending and the axial rotation show slight asymmetry due to the specific leg design of this brace.

The studied brace achieves the desired spatial head rotations while having small errors in translations. It was deemed useful to evaluate the extent of changes of the head position of each participant due to the structure of this brace when performing different head rotations. The reference point in the head frame is selected to be point $Q$ (FIGS. 6, 7), which has a constant offset from the origin of the end-effecter frame. FIGS. 16A through 16E represent data for a representative head position of one participant performing head flexion/extension in three trials. As shown in FIGS. 16A-16E, when the participants achieved certain head rotation allowed by the brace, the position of the head slightly differed from the one during the natural motions. The average pairwise deviation of the change of the head position under two conditions, with and without the brace, are 5.74±2.98 mm for flexion/extension, 10.70±4.05 mm for lateral bending, 8.50±3.12 mm for axial rotation, 11.55±5.14 mm for rolling motion.

Figure 14:
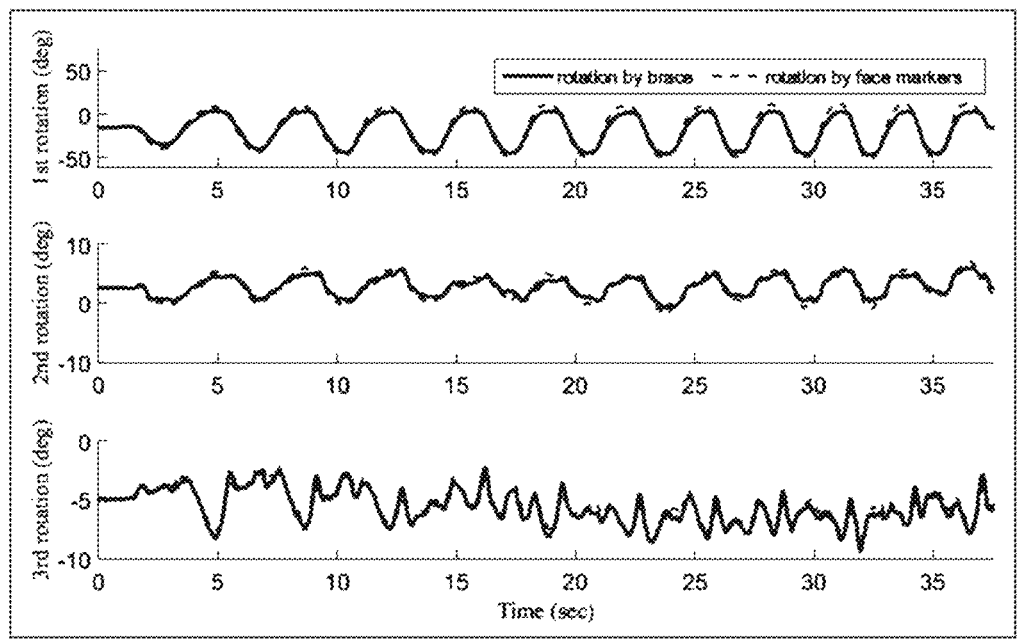
FIG. 14 shows the results of an investigation of relative movement of the subject head and brace during experiments.

The structure of the brace is optimized based on the anthropometry of one subject but was tested with nine other subjects of different sizes. The relative motion between the head and the brace during the experiment was investigated and the results are shown in FIG. 14. FIG. 14 shows a representative head rotation of one of the participants, measured by brace and face markers, respectively, and computed in space 1-2-3 convention. FIG. 14 demonstrates representative head motion captured by both face markers and the brace markers, respectively. It shows that the brace generally accommodates the head motion of the user, but it slides at extreme postures when the user turns the head. More specifically, the average errors between the brace and the face markers for all ten subjects are: −0.14±0.82 deg for flexion/extension, 0.89±0.89 deg for lateral bending, 0.15±0.54 deg for axial rotation, and 1.39±1.52 deg for rolling motion.

The experiment also evaluates the accuracy of the brace measurement with respect to the head rotations against the camera system. The forward kinematics is used to compute the position and the orientation of the head based on the angles recorded by the potentiometers. Then this computation is compared with the ones obtained by the brace markers. The arithmetic mean and root mean square errors were computed for each participant, and the average and the standard deviation over all 10 participants are shown in Table 4. The mean error is under 3.6±2.3 degrees and the RMS error is below 4.9±2.7 degrees for all types of motions for all participants.

TABLE 4

Average of the Mean and the RMS Errors of the
Brace Measurement over 10 Subjects.

|  | Flexion/Extension | Bending | Rotation | Rolling |
|---|---|---|---|---|
| Mean (deg) | 1.1 ± 2.5 | 2.5 ± 2.5 | 2.5 ± 2.9 | 3.6 ± 2.3 |
| RMS (deg) | 1.8 ± 2.9 | 3.1 ± 2.8 | 3.0 ± 3.0 | 4.9 ± 2.7 |

It is noteworthy that the measurement becomes less accurate when the subject reaches the extreme positions allowed by the brace, because of the collision between the mechanical components and the deformation of the plastic parts. However, the measurement is more accurate when the person moves within the work space of the brace. FIG. 17 shows average ranges of rotation in three planar motions, where the natural ranges are labeled between outer solid lines, the ranges allowed by the brace (BR) are shown between the inner solid lines solid red lines and the measurable ranges (MR) are labeled between two dashed black lines. FIG. 17 shows the measurable ranges of motion of the brace with the error margin to be ±3 deg. These data indicate that the measurable ranges for flexion/extension and lateral bending are nearly the same as the ranges of rotations allowed by the brace, while the measurable range for axial rotation is smaller than the brace range. They also indicate that interference between the mechanical components happened more often during axial rotation than the other motions. The measurement for axial rotation is more prone to the sensor errors.

Figure 25:
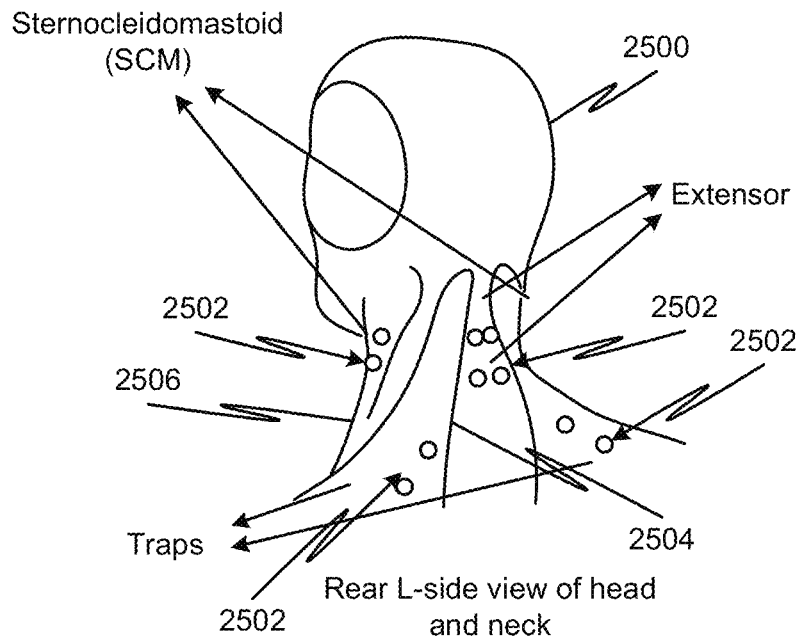
FIG. 25 shows the placement of EMG electrodes in a study described herein.

Referring to FIGS. 18A, 18B, data were collected from ALS patients who are in different stages of the disease. The ALS patients performed the same set of motions as young healthy subjects, described, five times at self-selected speeds. Data captured was used to characterize wearability of the brace by the patients, demonstrate simultaneous capture of the motion with the brace and muscle EMGs, and support analysis and interpretation of the motion and muscle EMG data. FIG. 18A shows the head motion of three ALS patients computed from the measurements using the brace and muscle EMGs recorded via a Noraxon EMG system. FIG. 18B shows representative motion of three ALS patients averaged across 5 cycles Muscle EMGs averaged across the cycles. The placement of the EMG electrodes are shown in FIG. 25. The signals from the brace and EMG system were cut in cycles and time normalized over the cycle for the analysis. The EMG signals were processed using the standard steps of removing DC offsets, high-pass filtering, rectification, normalization by the largest value and low-pass filtering during the experiment. These plots demonstrate the capability to record/analyze motion and EMG data with ALS patients.

The optimized computer model was realized into a physical prototype. Three rotary potentiometers were installed on the brace joints to measure the position and orientation of the user's head. These functioned as resistance angle encoders. A pilot study was conducted to quantitatively evaluate the wearability and measurement accuracy of the brace. Ten healthy individuals were recruited for the experiment. The brace demonstrated effective wearability over all subjects, averaging nearly 70% of the overall range of rotation of the head. In addition to the large available ranges of rotation, the average position error of the head wearing this brace is lower than 10 mm as compared to the natural head motions, indicating minimal constraints posed from the brace on the human head during motion. The brace fit well on all subjects that were tested, with negligible sliding occurring during all experiments. The brace was capable of measuring the head position and orientation within the allowed work space of the design. This was validated against a multi-camera motion capture system. The brace has reasonably good accuracy within its working space, though it is less accurate near its limits. With a 3-deg accuracy margin, the average measurable ranges that the brace achieved were 62%, 84% and 46% of natural head flexion/extension, lateral bending and axial rotation, respectively.

Additional embodiments are disclosed in FIGS. 19A through 22D. Referring now to FIGS. 19A, 19B, and 19C, a wearer 102 is strapped to a shoulder support 114 and a head support 104 which are interconnected by a brace 1900. The brace 1900 provides a 3 DOF kinematic mechanism with an encoder 1902 at each of three lower R joints 122A, 122B, and 122C (the latter three being hidden in FIG. 19A but visible in FIG. 19B). FIG. 19C shows a close-up of the encoder 1902. Terminals 1901 are shown unconnected but are connected, in physical embodiments, to a cable or soldered to an interface as will be understood by the skilled practitioner. The encoders 1902 are each connected to output position indications, for example resistance readings that are previously stored as corresponding values to angular relative positions between the lower base 1905L and first link 1905U. In other words, each encoder 1902 indicates the angular displacement position of a respective lower R joint about a respective axis 1904A, 1904B, and 1904C (generally 1904$i$). To provide additional inputs, inertial measurement units (IMU), integrated with accelerometers, gyros, and magnetometers, may be placed at the end-effecter (head platform 110) of the brace 1900 to provide further information about the position, velocity, and orientation of the head in real time. A torque sensor at the joint may be provided to indicate the joint torques. Pressure sensors placed within the headband of the user may provide information on the interaction forces between the brace and the user. The encoder signals (and other signals) may be provided to a processor (FIG. 26) and output to a master controller 2400. The encoders may provide negative feedback control of active components such as drives described with regard to FIGS. 21A-21C.

Note that instead of resistive encoders, other types of encoders may be used, such as relative position encoders such as hall effect or optical encoders, or other mechanisms for position indication may be used.

Figure 26:
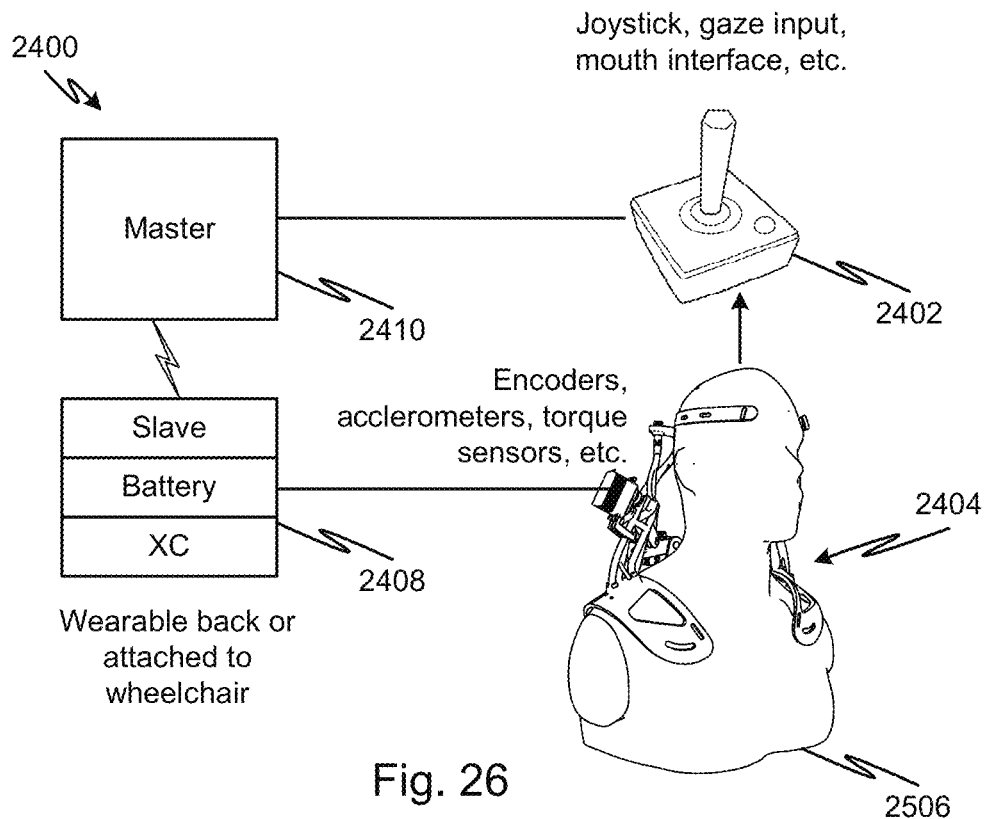
FIG. 26 is a diagram of a control and data-acquisition/user interface system whose features may be combined in various arrangements with the disclosed brace devices and systems.

In further embodiments, the lower R joints 122A-122C may be provided with a spring to maintain a desired urging force on the end effecter, head platform 110. This actuation could be either passive, using the springs to balance the external wrench, or active, using electronic motors as describe below with regard to FIGS. 21A-21C. To allow the user to have full control of the device, an interface will be developed with input devices, such as eye-trackers or joysticks as shown in FIG. 26.

By detecting the angles of the three lower R joints, the position and orientation of the end effecter can be computed. This information may be provided as feedback to a user, for example as a graphic to illustrate the user's range of motion in order to motivate or challenge the user to extend the range of motion or by a physician or therapist to document a patient's pathology or progress after intervention such as surgery, therapy, or sports training. Encoders may be combined with any of the disclosed embodiments, so for example, they may be integrated in the servo motor embodiments described below or combined with the spring-compensated R joints in the embodiments described below. An example of a graphic feedback would be that shown in FIG.

16E which shows the space cumulatively traversed by a cursor indicating a current position. This map could be generated using the encoder data rather than the image capture data as used to generate the presented data in FIG. 16E. A further example is that shown in FIG. 17, where a moving wiper could indicate a current position and moving maximum and average limits may be shown as well.

Figure 20A:
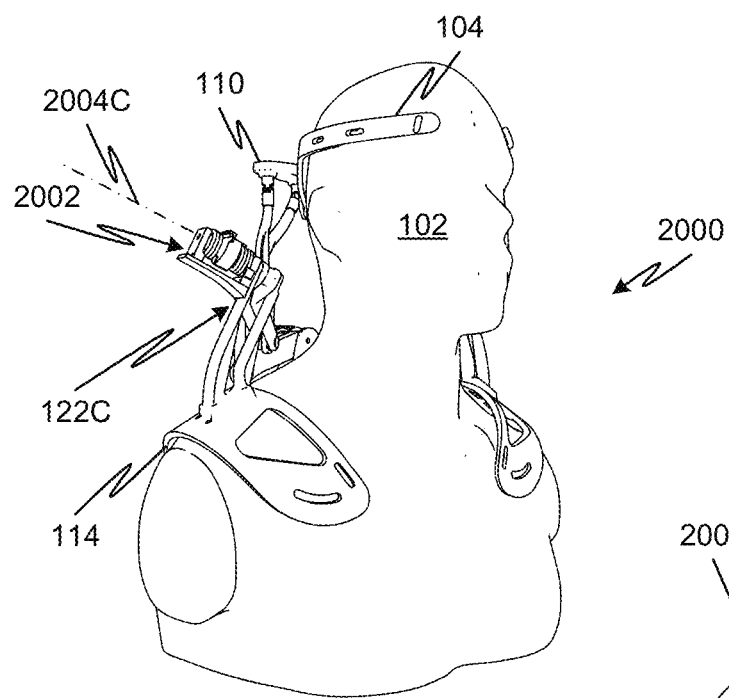
FIGS. 20A, 20B, and 20C show a brace according to the disclosed embodiments with spring compensation effecters connected to the first revolute (R) joints.
Figure 20C:
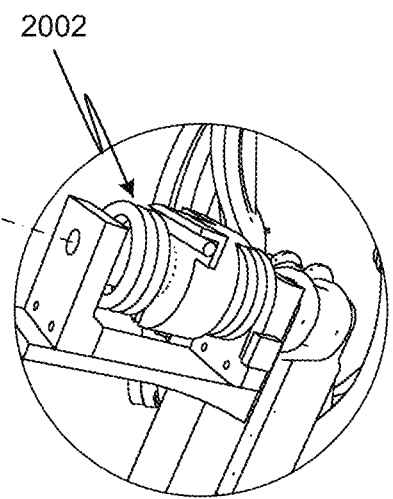
Figure 20B:
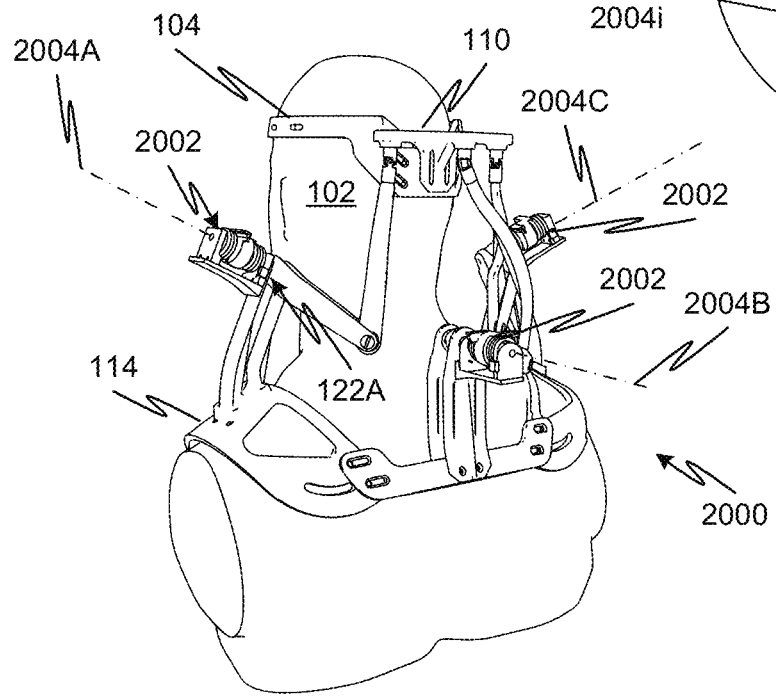

Referring now to FIGS. 20A, 20B, and 20C, a wearer 102 is strapped to a shoulder support 114 and a head support 104 which are interconnected by a brace 2000. The brace 2000 provides a 3 DOF kinematic mechanism with a spring 2002 at each of three lower R joints 122A, 122B, and 122C (the latter three being hidden in FIG. 20A but visible in FIG. 20B) that generates a restoring wrench as the joint is moved from a predefined "home" position. FIG. 20C shows a close-up of the spring 2002, which is configured so that it is balanced or relaxed when the R joint (122A-112C) is in a center position or range thereabout. Coil springs that are wound in opposite directions (one creates the restoring force in a negative direction and one creates a restoring force in the positive direction). Alternatively, a spring that generates restoring torques in both negative and position direction may be used. As above, encoders may be provided. A torque sensor at the joint may be provided to indicate the joint torques, for example by providing a force transducer between the spring and a stop. In embodiments, the springs may have adjustable deadbands, pretension, and variable spring constants as well as adjustable home positions. The springs maybe replaceable to provide different spring constants or this may be achieved by adjusting a force multiplier using mechanical advantage to tune the restoring torque. Instead of metal springs as shown, elastomer springs or rubber bands may be used. The action of a spring may also be provided by servo motors as in the embodiment of FIG. 21A-21C.

The spring enabled brace 2000 has the potential to keep the head in equilibrium in a desired configuration under the action of the weight of the head, applied muscle forces, and torques applied by the springs at the joints of the brace. Such a spring-loaded passive neck brace may have significant merits for patients with Head Drop Syndrome due to the following reasons. There is no need for motors, sophisticated electronics, and heavy power sources in the operation of the brace. This allows it to be lightweight and less expensive compared to powered brace solutions or more complex alternatives. Initial angles of the springs can be tuned to provide the necessary torques to keep the head in equilibrium at a configuration as the muscle efforts change or external forces vary. As indicated above, with adjustable dead-bands, adjustable home zones, adjustable spring constant, and other adjustable parameters, the system is highly customizable for patients. Due to the natural compliance of the passive neck brace, the user's neck is never locked in a configuration. There is always at least some maneuverability around the equilibrium. With inverse kinematics, it is possible to calculate the initial angles of the springs to hold the head at a target equilibrium position and the other parameters that may be adjusted for each patient or user.

Figure 23:
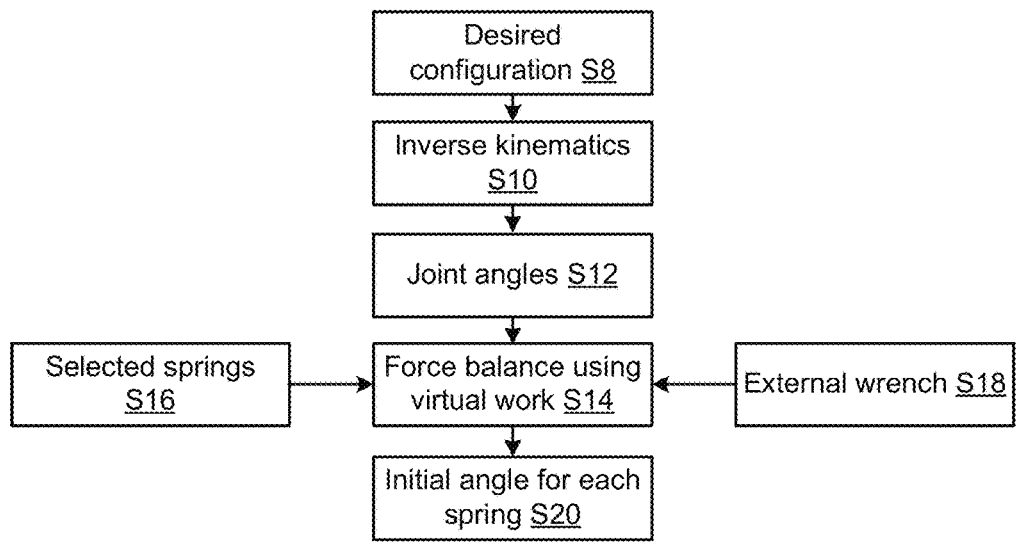
FIG. 23 shows a procedure for calculating the initial angles of springs to provide a counteracting wrench to maintain the position of the head of a wearer in a 3 DOF brace according to embodiments of the disclosed subject matter.

In the embodiment of FIGS. 20A-20C, a pair of torsional springs are used at the lower revolute joint in each of the legs to provide dual-directional joint torques. A locking mechanism may also be provided to permit the springs to be engaged to the lower joint for counterbalancing the weight of the user's head and other external forces on the system. Additionally, it can also be disengaged from the joints to change the equilibrium configurations. FIG. 23 outlines a computational procedure to achieve an equilibrium configuration by adjusting the initial angle of each spring at each lower revolute joint. Given a desired head configuration S8, the joint angles can be computed using the inverse kinematics S10. Provided that the spring parameters (i.e. spring constants, deflection angles S12) are specified S16 and the external load on the head is known S18, the initial angle of each spring S20 can be found by using the principle of virtual work S14. In order to obtain a desired workspace where the load can be balanced by selected springs, an optimization would be performed to determine the spring parameters. A computational procedure is required to set the initial angles for the springs. This may be provided by monitoring the angle from each joint which is being tuned. Inexpensive position sensors, such as described above may be used to indicate the joint angles. The spring-catch mechanism may provide for convenient disengagement and engagement on the lower revolute joints.

The feature of being able to reconfigure the equilibrium provides options to explore new solution approaches to different patient groups. A passive neck brace may be more comfortable to its user compared to a static neck brace because of its compliance. The spring loaded design, with the damping, may attenuate the jerky movements in cervical dystonia patients, where the springs/dampers could serve as a mechanical filter. The brace may encourage the users to recruit their own muscles to maintain equilibrium configurations to prevent potential muscle atrophy.

Figures 21A, 21B, 21C:
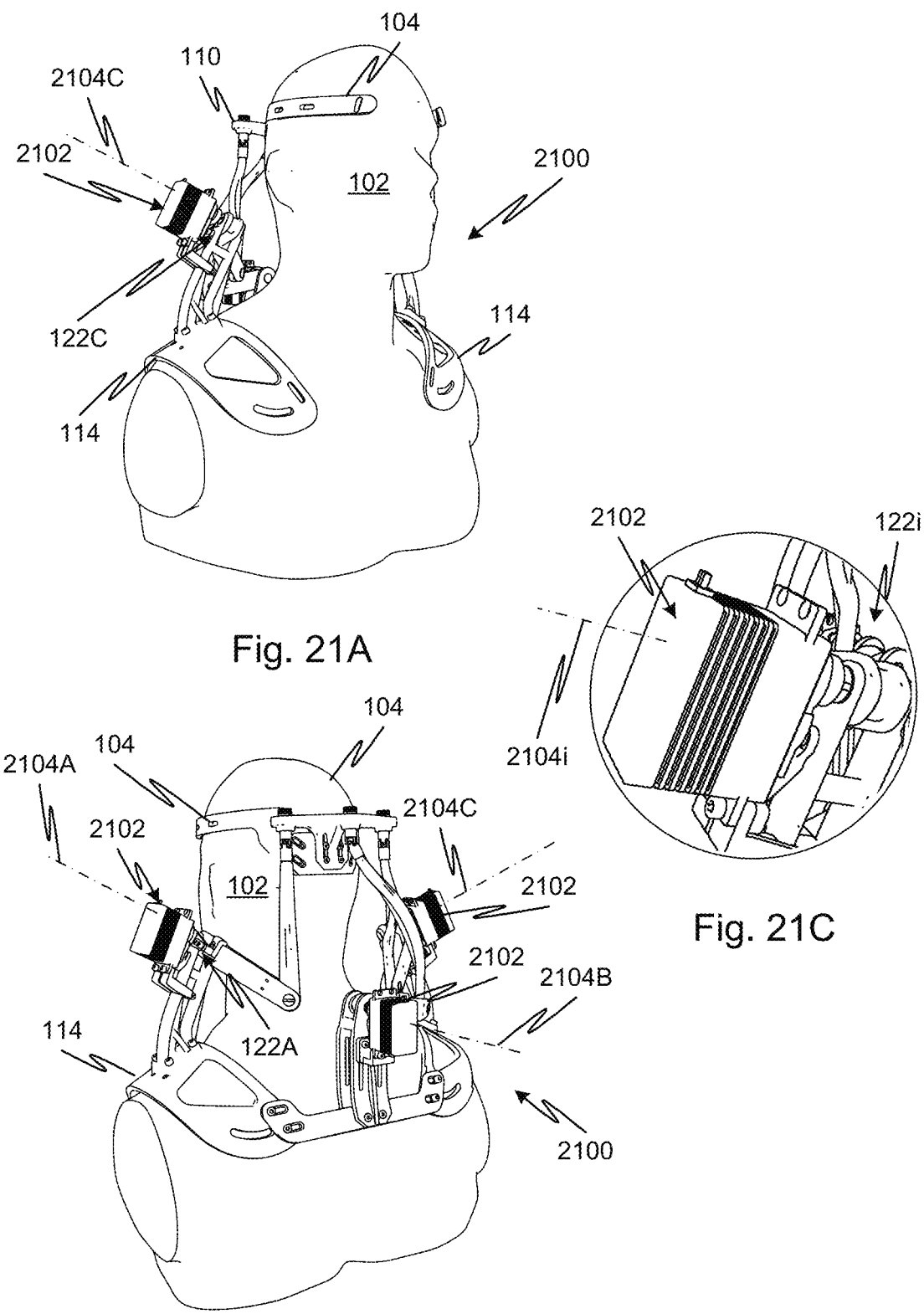
FIGS. 21A, 21B, and 21C show a brace according to the disclosed embodiments with servo motors connected to the first revolute (R) joints.

Referring now to FIGS. 21A, 21B, and 21C, a wearer 102 is strapped to a shoulder support 114 and a head support 104 which are interconnected by a brace 2100. The brace 2100 provides a 3 DOF kinematic mechanism with a servo motor drive 2102 at each of three lower R joints 122A, 122B, and 122C (the latter three being hidden in FIG. 21A but visible in FIG. 21B) that generates a commanded wrench according to controlled or feedback-based conditions. In a simple embodiment, a programmed restoring characteristic is provided as the R joint 122$i$ is rotated in response to displacements of the head of the user 102. FIG. 20C shows a close-up of the servo-motor drive 2102.

A powered brace may be most relevant for rehabilitative training/exercise for enabling movements of the neck in very weak patients using external user interfaces, such as a joystick. It may also provide advantages in terms of flexibility, for example, quick parameter setting that would take tool work in a passive spring configuration but only software in an active servo motor brace. Physical therapy aims to increase the passive range of motion of the neck and to strengthen the muscles on the contralateral side of the bent neck so that the head can be supported midline. During exercises that increase the passive range of motion, physical therapists ensure that the muscles are relaxed. Commonly, however, physical therapists lack quantitative information during the stretches and exercises they perform with patients. This affects the patient outcomes. There is also variability in how the same exercise is performed by different therapists or how a therapist performs the same exercise across different exercise sessions. The active neck brace could be programmed to perform exercises, while responding to data sensed from the subjects, so that the procedure is repeatable across training sessions.

An active neck brace powered by motors can provide controllable dynamic motion and forces during the head/neck motion of a user. With the 3-DOF brace, it is possible to actuate the brace by replacing the potentiometer at the lower R joint in each leg by a motor, as shown in FIGS. 21A-21C. In addition to the motors, sensors may be added or may be integrated in the motors to the system depending on the targeted application. In alternative configurations, servo motors, stepper motors may be used.

An inertial measurement unit (IMU), integrated with accelerometers, gyros, and magnetometers may be placed at the end-effecter of the brace to provide position and orientation of the head in real time. A torque sensor at the joint may be provided to read the joint torques. Pressure sensors placed within the headband of the user may provide information on the interaction forces between the brace and the user. FIG. 26 shows a basic framework for control and data acquisition, the details of which may be provided according to designer preference.

For safety, in embodiments, the range of motion that the brace permits may be limited to a range that is smaller than the typical motion of human head/neck. From a control perspective, the range of motion and torque being applied by the motors may be detected and regulated in real time to enforce safe predetermined thresholds to prevent motions from surpassing safe limits for physical motion in the head/neck. Software may provide for these functions. Springs or frangible connections may be integrated between motors and effecters to provide compliance in case limits are exceeded.

Figure 24:
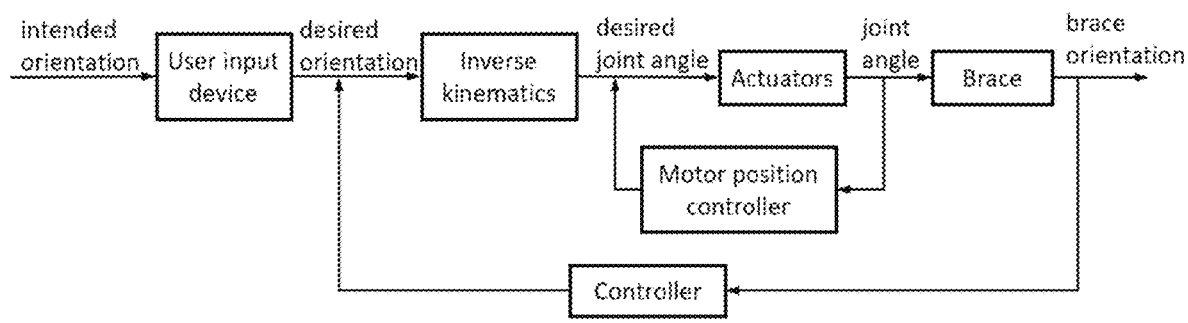
FIG. 24 shows a method for controlling an active brace as described with reference to FIGS. 21A-21C using an input device, according to embodiments of the disclosed subject matter.

A powered active neck brace can be used as an assistive device for very weak patients with head drop, such as in ALS, to regain head mobility. With input devices, such as joysticks, eye trackers, and EMG interfaces. See FIG. 24. A user can intentionally command the motors to move the brace and therefore position/orientation of their head. An active brace may be used as an exercise tool for patients with head movement disorders to actively recruit and strengthen their neck muscles, thereby, diminish muscle atrophy. Such a brace may be programmed in force control mode to provide desired resistance to motion of the head/neck. Active brace may be employed as a training device with motor learning principles to facilitate treatment in movement disorders, such as cervical dystonia. Different training strategies can be applied, such as assist-as-needed and error enhancement. A force field tunnel may be generated around a target path which a patient needs to follow and will provide resistance/assistance as needed. A user interface incorporating various sensory cues, such as visual/audio feedback, may be provided to allow the user can be engaged in the training. In embodiments, the active neck brace can become a fully portable unit with its power source, controller, electronics, and sensors. FIG. 26. There can be potential uses of this technology in video gaming and sports. The brace can be incorporated in wheelchairs with additional sensors and joysticks.

Figure 22A:
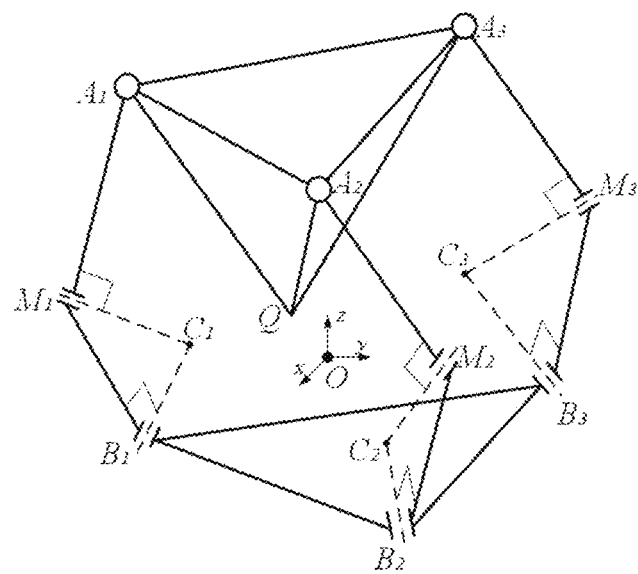
FIGS. 22A and 22B show the kinematic schematic diagram of the 3 DOF brace described herein and a 6 DOF design shown in FIGS. 22C, 22D, and 22E.
Figure 22B:
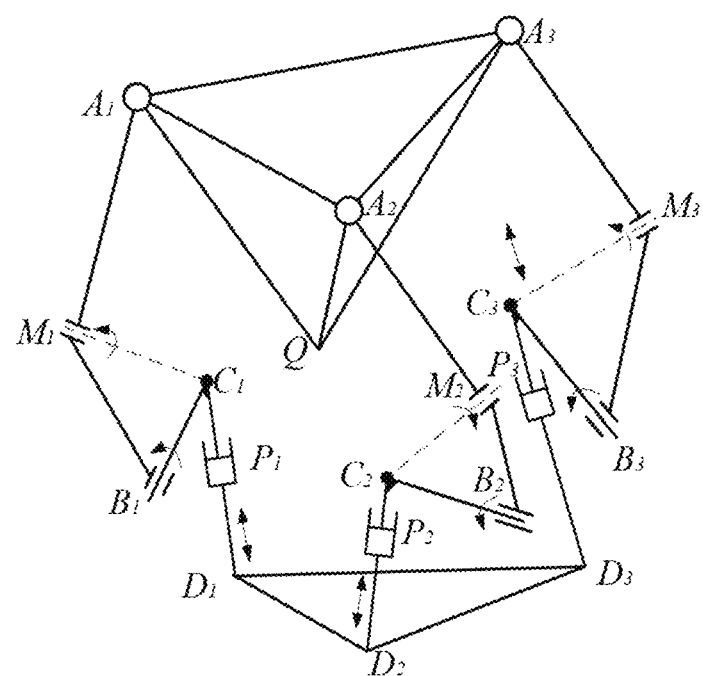
Figure 22C:
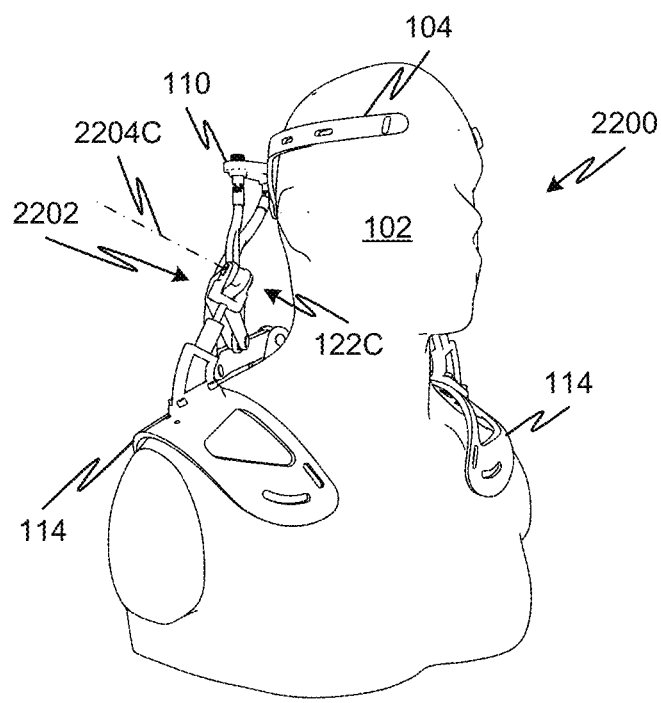
FIGS. 22C, 22D, and 22E show a brace according to the disclosed embodiments with six degrees of freedom based on the 3 DOF embodiments disclosed herein.
Figure 22E:
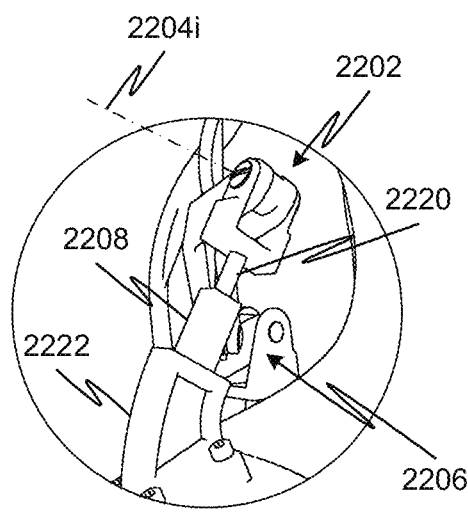
Figure 22D:
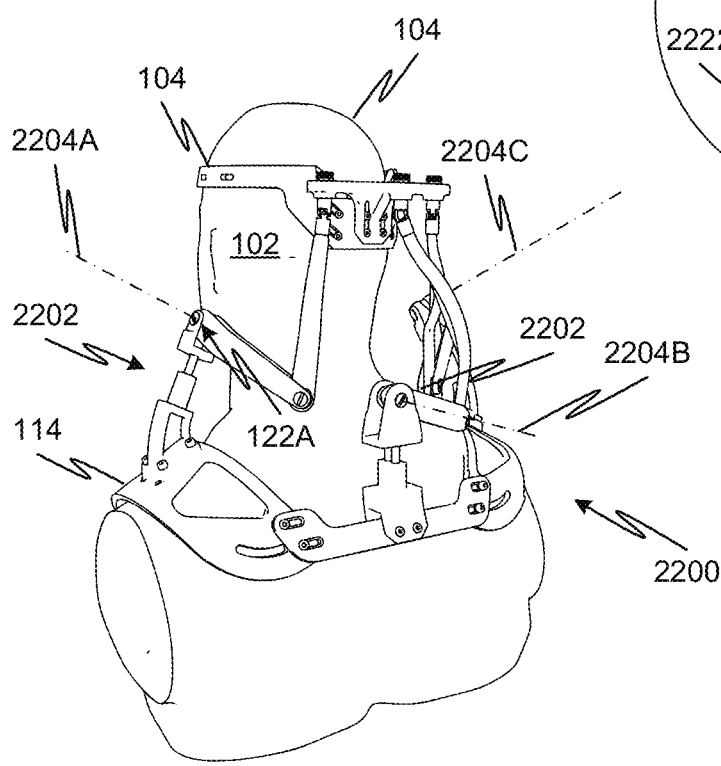

FIGS. 22A and 22B show the kinematic schematic diagram of the 3 DOF brace described herein and a 6 DOF design shown in FIGS. 22C, 22D, and 22E. FIGS. 22C, 22D, and 22E. show a brace according to the disclosed embodiments with six degrees of freedom based on the 3 DOF embodiments disclosed herein. FIG. 22A shows the 3 DOF configuration disclosed elsewhere herein. The addition of linear actuators between a shoulder support defined by $D_1$-$D_2$-$D_3$ and the 3 DOF structure of FIG. 22A is shown in FIG. 22B.

As indicated above, the human head/neck motion naturally has six degrees-of-freedom (DOF) with respect to the upper trunk. Ideally, a brace should have six actuated DOF to have precise control of the motion of the head with respect to the shoulders. However, such a six DOF design may be bulky and may compromise its wearability by the human users. As a result, the 3 DOF configuration was devised. There may be circumstances where the value of the additional degrees of freedom are worth the tradeoffs.

The modeling and design of the 3 DOF brace may provide a basis for a 6 DOF brace as disclosed above in FIGS. 22A-22E. The architecture of the 3 DOF brace is extended by adding a sliding joint in each chain. This preserves the compactness and other benefits of the 3DOF configuration. The computational procedure for the six DOF mechanism can be extended from on the existing kinematics of the three DOF mechanism.

The features presented in the present application can be further extended to exoskeleton designs for other quasi-spherical joints in the body, such as the shoulder and hip joints.

Although embodiments of the brace show a saddle-shaped shoulder support, other attachments to the trunk of the wearer are possible. For example, the brace could be connected to the trunk via a body harness such as worn by Steadicam operators or as provided for rack-type backpacks. Alternative input devices may be used with the disclosed embodiments. For example, voice commands may be used instead of a joystick for manipulating an active brace or changing parameters such as force-tunnel parameters.

According to embodiments, the disclosed subject matter includes a neck brace. A stabilizing platform is affixable to a torso of a wearer. An effecter platform is affixable to a head of a wearer. The stabilizing and effecter platforms are connected by a mechanism providing at least two degrees of freedom of motion between the stabilizing and effecter platforms.

In embodiments, the mechanism may provide three degrees of freedom, the degrees of freedom being selected to permit natural motion of the head of the wearer.

In any embodiments, the mechanism may include at least one RR joint. In further embodiments, the mechanism includes at least two RR joints. In further embodiments, the mechanism includes at least three RR joints. In further embodiments, the RR joint or joints each include an S joint. In further embodiments, the rotations of the RR joints are sufficient to provide at least 70% of said degrees of freedom. In further embodiments, the mechanism joints attach to the effecter platform at a position that coincides with the back of the head of the wearer when worn by the wearer. In further embodiments, the mechanism is connected to the stabilizing platform at a side and/or behind the torso of the wearer, whereby an unobstructed forward view of the wearer is provided. In further embodiments, the mechanism includes 3 RRS joints. In further embodiments, the mechanism employs 3 RRS joints to permit three degrees of freedom of motion of the head of the wearer. In further embodiments, each RRS joint includes a first R joint proximate the stabilizing platform. In further embodiments, each RRS joint includes an S joint proximate the effecter platform. In further embodiments, each of the first R joints is supported by the stabilizing platform at a fixed position above the shoulders of the wearer. In further embodiments, the fixed positions are below the base of a skull of the wearer. In further embodiments, the stabilizing platform is affixable to the torso by straps. In further embodiments, the stabilizing platform is affixable to the torso by straps and by saddle-shaped supports that rest on the shoulders of the wearer. In further embodiments, two of the S joints are proximate the head of the wearer and one is remote from the head of the wearer. In further embodiments, one or more kinematic chains of said mechanism that includes an R joint further includes an urging mechanism connected to said mechanism in a position that cause said one or more chains R joint to rotate. In further embodiments, the urging mechanism includes a spring. In further embodiments, the urging mechanism includes an actuator. In further embodiments, the actuator is a rotary actuator. In further embodiments, one or more kinematic chains of said mechanism that includes an R joint further includes an encoder that indicates a rotary displacement of said one or more chains R joints. In further embodiments, the rotary actuator is a servomotor. In further embodiments, the three degrees of freedom are selected to provide a substantially spherical motion of the head of the wearer. In further embodiments, the three degrees of freedom include coupled translation of a spherical center of rotation with translation of the center of rotation. Further embodiments include a controller that creates a force field defined by a restoring force that varies with the possible positions of the wearers head and or a controller that creates a force field defined by a challenging force that varies with the possible positions of the wearers head. The controller may create a force field defined by a challenging force that resists movement of the head, with the magnitude of resistance varying with the possible positions of the wearers head. The controller may control the servomotors responsively to an eye-tracking input device. The servomotors may be controlled by an eye-tracking input device aimed at the wearer. An imaging transducer may be used by the eye-tracking input device, where the imaging device is connected to the head effecter platform.

According to further embodiments, a neck brace has a stabilizing platform that is affixable to a torso of a wearer and an effecter platform that is affixable to a head of a wearer. The stabilizing and effecter platforms being connected by at least two kinematic chains, each including two links, a first link being connected by a first R joint to the base platform and a second link connected to the first by a second R joint, the second link being connected by an S joint to the effecter platform. In the present disclosure, although the term "kinematic chain" may refer to a mathematical abstraction of a physical thing, it also limits structure and therefore can be used to characterize a physical device or system.

According to variations, the further embodiments may include ones in which the links are embodied in plastic or metal members. According to variations, the further embodiments may include ones in which the first R joint is connected to the base platform on a distal end of a riser that extends vertically above the shoulder of a wearer of the base platform. According to variations, the further embodiments may include ones in which the base platform is saddle shaped to conform to the top of the shoulders of a person. According to variations, the further embodiments may include ones that include padding attached to a concave surface of the base platform. According to variations, the further embodiments may include ones in which the at least two are at least three. According to variations, the further embodiments may include ones in which the first R joint has a position sensor indicating an angular position of the first link relative to the base platform. According to variations, the further embodiments may include ones in which the position indicator includes an encoder. According to variations, the further embodiments may include ones in which the encoder includes a potentiometer.

According to variations, the further embodiments may include ones in which the first R joint has a motor drive controlled by a controller, permitting the controller to define a force tunnel for each of the at least three kinematic chains. According to variations, the further embodiments may include ones in which the connection between the base platform and effecter platform includes at least three R-R-S kinematic chains. According to variations, the further embodiments may include ones in which the two R joints have respective axes that cross. According to variations, the further embodiments may include ones in which the two R joints have respective axes that cross at different locations in 3D space. According to variations, the further embodiments may include ones in which the two R joints have respective axes that cross at points spaced apart from the linkages defined by the kinematic chains and toward the neck of a wearer of the base platform. According to variations, the further embodiments may include ones in which the effecter platform includes a headband that is positioned to wrap around the top of the head of a wearer. According to variations, the further embodiments may include ones in which the rotations of the linkages defined by the kinematic chains are sufficient to provide at least 70% of said degrees of freedom. According to variations, the further embodiments may include ones in which one or more kinematic chains of said mechanism that includes an R joint further includes an urging mechanism connected to said mechanism in a position that cause said one or more chains R joint to rotate. According to variations, the further embodiments may include ones in which the urging mechanism includes a spring. According to variations, the further embodiments may include ones in which the urging mechanism includes an actuator. According to variations, the further embodiments may include ones in which the actuator is a rotary actuator.

According to variations, the further embodiments may include ones in which one or more kinematic chains of said mechanism that includes an R joint further includes an encoder that indicates a rotary displacement of said one or more chains R joints. According to variations, the further embodiments may include ones in which the rotary actuator is a servomotor. According to variations, the further embodiments may include ones that include a controller that creates a force field defined by a challenging force that resists movement of the head, with the magnitude of resistance varying with the possible positions of the wearer's head. According to variations, the further embodiments may include ones in which the servomotors are controlled by an eye-tracking input device. According to variations, the further embodiments may include ones in which the servomotors are controlled by an eye-tracking input device aimed at the wearer. According to variations, the further embodiments may include ones in which an imaging transducer used by the eye-tracking input device is connected to the head effecter platform.

Note that although embodiments described exhibited 3 degrees of freedom, it is possible for the number to be increased or even limited to a smaller number if less flexibility is desired. With an alternate arrangement of joints in the chains, the system can also provide between 3-6 degrees-of-freedom motion to the head.

EXAMPLES

Note that in the following a new figure sequence number begins with FIG. 1. Also, a new sequence of equations begins starting at 1.

Patients with head drop need external support to keep the head up and move it around. Their neck muscles are not strong enough to bring the head back to the neutral configuration from a flexed position. They often use static neck braces to keep the head in the upright configuration. These braces do not allow movement of the head-neck and cause further atrophy to the muscles. In this paper, inventors present a spring-loaded dynamic neck brace to support the head in a desired equilibrium configuration. The brace is fitted with torsional springs that can provide restoring forces to the head as it is displaced from the equilibrium configuration. The equilibrium configuration is adjustable by preloading the springs. In this paper, inventors present a mathematical model and validate through experiments with a prototype. The dynamic brace was found to provide sufficient support to the neck in a configuration while also allowing the users to move their head.

Static neck braces are commonly used today by patients who have dropped head syndrome (DHS). This condition is seen in a number of neurological diseases such as Amyotrophic Lateral Sclerosis (ALS), Primary Lateral Sclerosis (PLS), Parkinson's Disease (PD) and Cerebral Palsy (CP). Current braces are typically made of foam or plastic and fix the head relative to the shoulders with support under the chin. These braces constrain the head of the user to a single configuration and are typically not favored by patients as these apply pressure under the chin causing difficulty in swallowing, breathing, and speaking. In addition, these braces cause skin breakdown and can potentially weaken neck muscles due to lack of use. Despite the fact that most patients have weakness in lifting their head, some have adequate strength to perform lateral motion.

There is a growing interest in developing neck braces to meet the needs of these patients. A recent study reported a static neck brace for ALS patients, which uses forehead attachment rather than under-chin attachment. A second passive design, with flexible inserts in fabric, allows a small rotational movement of the head in upright posture for patients with weak neck extensors. A powered headrest was developed to allow two rotations of the head by tracking the eye movements for ALS patients. However, the design needs to be installed on a wheelchair and is too heavy to be carried by a person.

The inventor's group has recently developed a neck brace as a measurement tool and as an assistive device with motors. The brace has three degrees-of-freedom (DOF) and allows the head to achieve different orientations with minimal translational errors during movement. The brace is composed of a base that rests on the shoulders, secured by a pair of straps. A headband worn around the forehead acts as the end-effector of a parallel mechanism, which has three revolute-revolute-spherical (RRS) chains between the shoulder support and the headband. These RRS chains are located at the back of the head so that these do not block the line of view of the user. Preliminary evaluations with healthy subjects, as presented in the two papers, indicated that the brace can measure and assist the head motion with motors.

The embodiments includes ones in which passive elements such as springs provide the needed support to the head with the same brace architecture. In such embodiments, provide more comfort than rigid neck braces as well as compliance to a user. A feature of such spring-type mechanisms is the lack of motors and a control system. In embodiments, three torsional springs, one within each chain of the parallel mechanism, are used to counterbalance the gravitational load of the head. The equilibrium configuration of the head can be adjusted by tightening the springs at desired rest angles. This allows the head to rest in different configurations. An important feature of this design is that the spring actuators are simple, lightweight, and inexpensive. The springs can be adjusted based on the need of the user.

Data presenting evaluation of the foregoing embodiments with healthy human subjects demonstrate that the brace provides support to keep the head in a desired configuration, and the brace allows movement to the user around a nominally chosen configuration. The results also validate a mathematical model of the brace kinematics and forces. The brace can provide support at a target configuration and also local compliance around it.

Figures 27A, 27B:
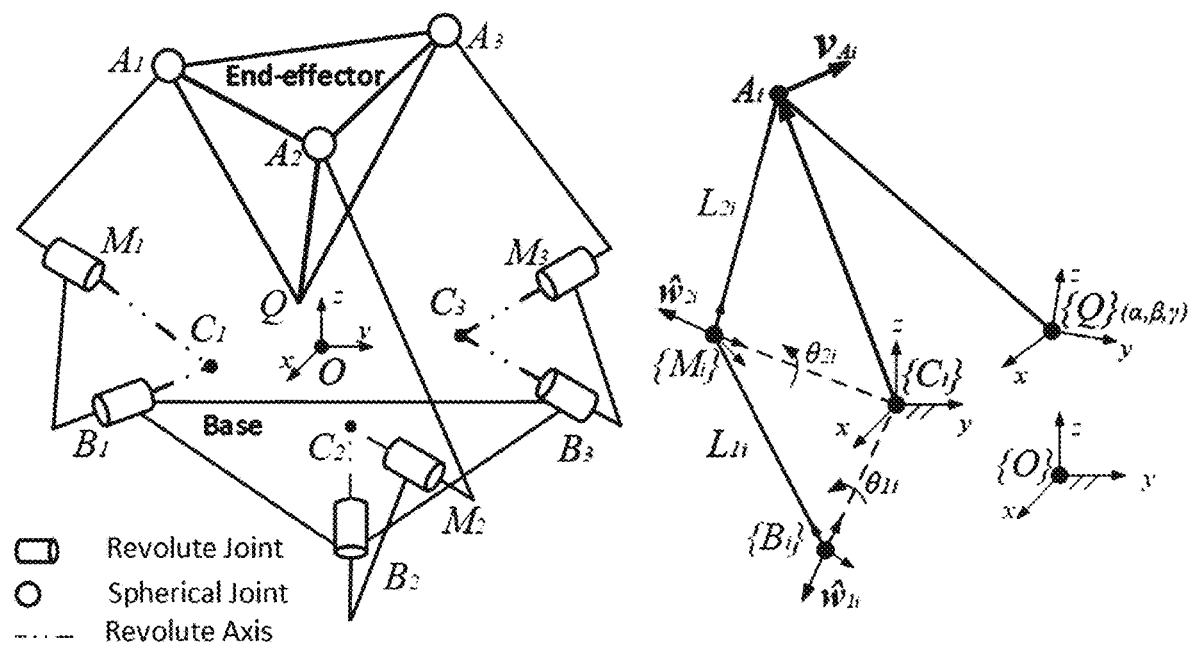
FIG. 27A shows kinematic model of 3-RRS mechanism used in a brace according to embodiments, where B1, B2 and B3 form a base attached to the shoulders; A1, A2, A3 and Q form an end-effector attached to the head; three RRS chains with joints centered at Bi, Mi and Ai (i=1, 2, 3), connect the base with the end-effector and BiCi and MiCi are revolute axes and intersect at a fixed point Ci in the base.
FIG. 27B shows a loop closure of one kinematic chain of the three indicated in FIG. 27A where $\{O\}$ and $\{Ci\}$ are inertial frames with the same orientation; $\{Bi\}$ is the proximal link frame centered at Bi and $\{Mi\}$ is the distal link frame centered at Mi; the lengths of the links are L1i and L2i, respectively; $\hat{w}1i$ and $\hat{w}2i$ are unit vectors indicating the orientations of the two revolute joints and the joint angles are represented by $\theta 1i$ and $\theta 2i$, respectively; $\{Q\}$ is the end-effector frame centered at a reference point Q; the orientation of $\{Q\}$ is represented by $(\alpha,\beta,\gamma)$ in body 3-2-3 sequence; and vA is the velocity of point Ai.

The geometry of the 3 DOF neck brace is shown in FIGS. 27A and 27B. A model for the coupled kinematics and statics of the mechanism when torsional springs are added within the system was developed. The gravitational load due to the weight of the head is equilibrated by the spring torques. A Jacobian matrix was derived to relate the linear and angular velocity of the end-effector to the angular rates of the revolute joints on which the torsional springs are mounted. Given the external forces acting on the end-effector, the equilibrating spring torques at the joints are solved using the principle of virtual work. Therefore, the free angles of each spring are computed using the model, assuming the spring obeys Hooke's Law.

FIG. 27A shows kinematic model of 3-RRS mechanism used in a brace according to embodiments, where B1, B2 and B3 form a base attached to the shoulders; A1, A2, A3 and Q form an end-effector attached to the head; three RRS chains with joints centered at Bi, Mi and Ai (i=1, 2, 3), connect the base with the end-effector and BiCi and MiCi are revolute axes and intersect at a fixed point Ci in the base.

FIG. 27B shows a loop closure of one kinematic chain of the three indicated in FIG. 27A where $\{O\}$ and $\{Ci\}$ are inertial frames with the same orientation; $\{Bi\}$ is the proximal link frame centered at Bi and $\{Mi\}$ is the distal link frame centered at Mi; the lengths of the links are L1i and L2i, respectively; $\hat{w}_{1i}$ and $\hat{w}_{2i}$ are unit vectors indicating the orientations of the two revolute joints and the joint angles are represented by $\theta_{1i}$ and $\theta_{2i}$, respectively; $\{Q\}$ is the end-effector frame centered at a reference point Q; the orientation of $\{Q\}$ is represented by $(\alpha,\beta,\gamma)$ in body 3-2-3 sequence; and $v_A$ is the velocity of point Ai.

Figure 28:
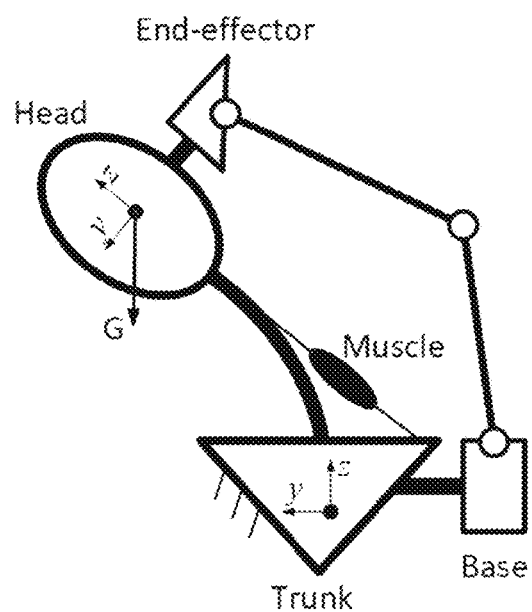
FIG. 28 shows a schematic of force balance of the head under gravity and assistance of the brace.

FIG. 28 shows a schematic of force balance of the head under gravity and assistance of the brace. The base and the end-effector of the brace are rigidly attached to the trunk and head, respectively.

In the analysis, $A_i$'s (i=1,2,3) are fixed points in the end-effector frame $\{Q\}$ centered at point Q, as shown in FIGS. 27A, 27B. The velocity of the point $A_i$ can be written as $$v_{A_i} = v_Q + \omega_e \times r_{QA_i}, i=1,2,3 \qquad (1)$$

where $v_Q$ is the velocity of point Q, $\omega_e$ is the angular velocity of the end-effector in the inertial frame $\{O\}$ and $r_{QA_i}$ represents the vector $$r_{QA_i}.$$

Additionally, point n moves on a spherical surface centered at the origin of inertial frame $\{C_i\}$ in each chain. Hence, $$r_{C_iA_i} \cdot v_{A_i} = 0, i=1,2,3 \qquad (2)$$

where $r_{C_iA_i}$ represents the vector $$r_{C_iA_i}.$$

On substituting Equation (1) into (2), inventors combine all three chains. Inventors make use of the identity a·(b×c)=(a×b)·c to obtain the following system of equations written in a matrix form, where all vectors are written in a common coordinate frame {O}, $$\overline{M}_1{}^{\{O\}}v_Q + \overline{M}_2{}^{\{O\}}\omega_e = \overset{r}{0} \qquad (3)$$

where $$\overline{M}_1 = {}^{\{O\}}[r_{C_1A_1} r_{C_2A_2} r_{C_3A_3}]_{3\times 3}^T,$$

$$\overline{M}_2 = {}^{\{O\}}[r_{QA_1} \times r_{C_1A_1}\, r_{QA_2} \times r_{C_2A_2}\, r_{QA_3} \times r_{C_3A_3}]_{3\times 3}^T,$$

$${}^{\{O\}}v_Q = {}^{\{O\}}[x_Q y_Q z_Q]^T,$$

$${}^{\{O\}}\omega_e = {}^{\{O\}}[\omega_x \omega_y \omega_z]^T,$$

$${}^{\{O\}}\omega_e = {}^{\{O\}}[\omega_x \omega_y \omega_z]^T,$$

Let $\overline{M} = -\overline{M}_2^{-1}\overline{M}_1$ and the angular velocity of the end-effector ${}^{\{O\}}\omega_e$ can be then expressed as, $${}^{\{O\}}\omega_e = \overline{M}{}^{\{O\}}v_Q. \qquad (4)$$

The velocity of point $A_i$ can also be expressed as $$v_{A_i} = v_{M_i} + \omega_{L_{2i}} \times r_{M_iA_i}, i=1,2,3 \qquad (5)$$

where $$v_{M_i} = \dot{\theta}_{1i}\hat{w}_{1i} \times r_{B_iM_i}$$

$$\omega_{L_{2i}} = \dot{\theta}_{1i}\hat{w}_{1i} + \dot{\theta}_{2i}\hat{w}_{2i}$$

$v_{M_i}$ is the velocity of point $M_i$ and $\omega_{L_{2i}}$ is the angular velocity of the distal link $M_iA_i$ in inertial frame $\{C_i\}$. Combining Equation (1) and (5) and noting that $r_{B_iM_i} + r_{M_iA_i} = r_{B_iA_i}$, the following vector equation for each chain can be obtained:

$$\dot{\theta}_{1i}\hat{w}_{1i} \times r_{B_iA_i} + \dot{\theta}_{2i}\hat{w}_{2i} \times r_{M_iA_i} = v_Q + \omega_e \times r_{QA_i}, i=1,2,3 \qquad (6)$$

Inventors eliminate the angular rate $\theta_{2i}$ by taking the dot product with $\hat{w}_{2i}$ on both sides of Equation (6). The equation then becomes a scalar equation $$(\dot{\theta}_{1i}\hat{w}_{1i} \times r_{B_iA_i}) \cdot \hat{w}_{2i} = (v_Q + \omega_e \times r_{QA_i}) \cdot \hat{w}_{2i}, i=1,2,3 \qquad (7)$$

Letting $\theta_1 = [\theta_{11}\, \theta_{12}\, \theta_{13}]^T$, one can rewrite Equation (7) and obtain the following matrix equation expressed in the inertial frame {O} relating the angular rates of the proximal joints to the linear and angular velocity of the end-effector, $$H\dot{\theta}_1 = N_1{}^{\{O\}}v_Q + N_2{}^{\{O\}}\omega_e \qquad (8)$$

where $$H = {}^{\{O\}}\begin{bmatrix}(r_{B_1A_1} \times \hat{w}_{21})\cdot \hat{w}_{11} & 0 & 0 \\ 0 & (r_{B_2A_2} \times \hat{w}_{22})\cdot \hat{w}_{12} & 0 \\ 0 & 0 & (r_{B_3A_3} \times \hat{w}_{23})\cdot \hat{w}_{13}\end{bmatrix}_{3\times 3},$$

$$N_1 = {}^{\{O\}}[\hat{w}_{21}\ \hat{w}_{22}\ \hat{w}_{23}]_{3\times 3}^T,$$

$$N_2 = {}^{\{O\}}[r_{QA_1} \times \hat{w}_{21}\ r_{QA_2} \times \hat{w}_{22}\ r_{QA_3} \times \hat{w}_{23}]_{3\times 3}^T.$$

On substituting Equation (4) into Equation (8), the angular rates $\dot{\theta}_1$ can be related to the linear velocity of the end-effector $v_Q$ and expressed in the inertial frame {O} as follows, $$\dot{\theta}_1 = H^{-1}(N_1 + N_2\overline{M}){}^{\{O\}}v_Q. \qquad (9)$$

Similarly, the angular rates $\dot{\theta}_1$ can be related to the angular velocity of the end-effector $\omega_e$, expressed in the inertial frame {O} through, $$\dot{\theta}_1 = H^{-1}(N_1\overline{M}^{-1} + N_2){}^{\{O\}}\omega_e. \qquad (10)$$

Inventors define $J_v = (N + N_2\overline{M})^{-1}H$ and $J_\omega = (N_1^{-1}\overline{M} + N_2^{-1})H$ so that inventors can write Equations (9) and (10) into the following matrix form $${}^{\{O\}}\begin{bmatrix}v_Q \\ \omega_e\end{bmatrix} = J\dot{\theta}_1 \qquad (11)$$

where $$J = \begin{bmatrix}J_v \\ J_\omega\end{bmatrix}_{6\times 3}.$$

The model balances the weight of the head with torques provided by the brace joints in a configuration. Using the principle of virtual work, the work done by the weight of the head $\delta W_E$ and by the torques applied at the brace joints $\delta W_J$ satisfy, $$\delta W_E + \delta W_J = 0 \qquad (12)$$

where $$\delta W_E = f \cdot v_Q + m \cdot \omega_e$$

$$\delta W_J = \sum_{i=1}^{3} \tau_i \dot{\theta}_{1i},\ i=1,2,3$$

f and m are the external force and moment applied to the end-effector, and $\tau_i$ is the joint torque applied at each of the three proximal revolute joints. Let $\tau$ be $[\tau_1\ \tau_2\ \tau_3]^T$, and then using Equations (8) and (12), one obtains:

$$\tau = -J^T \begin{bmatrix}{}^{\{O\}}f \\ {}^{\{O\}}m\end{bmatrix} \qquad (13)$$

where $${}^{\{O\}}f = {}^{\{O\}}[f_x f_y f_z]^T,$$

$${}^{\{O\}}m = {}^{\{O\}}[m_x m_y m_z]^T,$$

In case of using linear torsional springs, the torque in each joint is $$\tau_i = k_i(\theta_{1i} - \theta_{1i}^0), i=1,2,3. \qquad (14)$$

Given the spring constant, the free angle $\theta_{1i}^0$ of each spring can be solved as $$\theta_{1i}^0 = \theta_{1i} - \frac{\tau_i}{k_i}, i = 1, 2, 3. \quad (15)$$

In order to apply Equations (13)-(15) to solve for the free angle for each spring, the force and moment applied to the end-effector f and m are needed. The force/moment applied to the end-effector of the brace are measured by a force/torque sensor. An example is shown in FIG. 28 where the head is at a flexed configuration and the weight of the head is the only external force.

Figure 29:
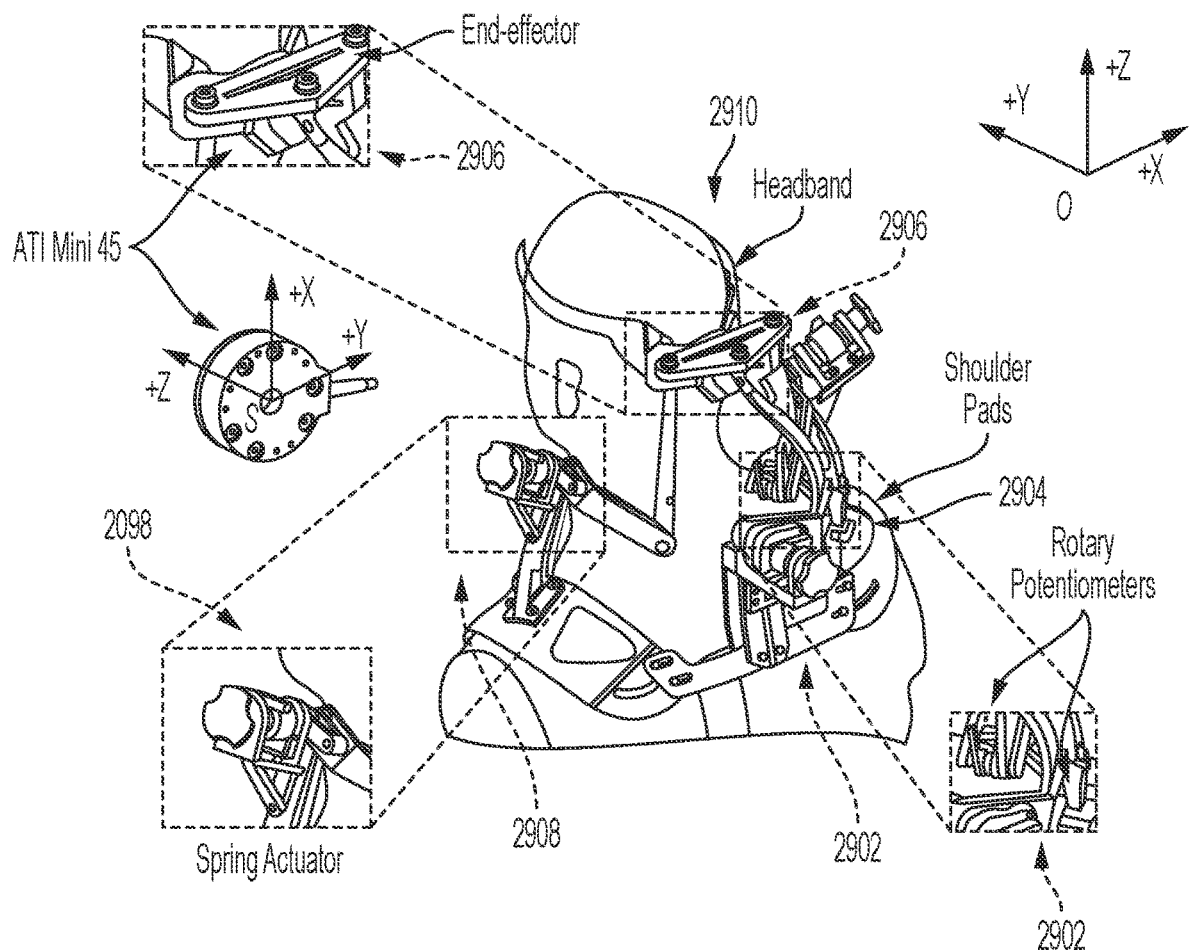
FIG. 29 shows an oblique view of a CAD rendering of the brace generally configured as described with reference to FIGS. 20A-20C with particular details and showing the spring mechanism used for the experiments described herein.

Referring to FIG. 29, the brace is generally configured as discussed with reference FIGS. 20A-20C with a shoulder support and a head interface 2910 that includes a headband attached to a platform (end effecter). The spring actuators are on the most proximal joints 2902 (only one is indicated but as can be confirmed by inspection and as indicated above, the three linkages may possess the same basic joint configuration; of the revolute joints, one is proximal for each chain and one is distal). Three rotary potentiometers are mounted on the distal revolute joints 2904. A six-axis force/torque sensor may be installed in between the end-effecter (platform connected rigidly to the head interface) and the headband. The inertial frame is defined as O (green) and the sensor frame is shown as S. The mounting adapter plate of the force/torque sensor is attached to the end-effector while the tool adapter plate is attached to the headband, with +Z pointing from the mounting adapter plate to tool adapter plate.

The shoulder support and head brace are connected through three RRS chains. Two of these chains are symmetrically placed (though they may be asymmetrically placed or non-identical in alternative embodiments) at the back around the center of the neck while the third chain is located on the mid-line at the back. A six-axis force/torque transducer (Mini45-E, ATI Industrial Automation, North Carolina, USA) is embedded in the headband to measure the interaction force/moment between the brace and the head.

As shown in FIG. 29, three spring actuators are added at the three proximal revolute joints to provide passive support to the structure. Three rotary potentiometers are mounted on the distal revolute joints to measure the joint angles.

Figure 30:
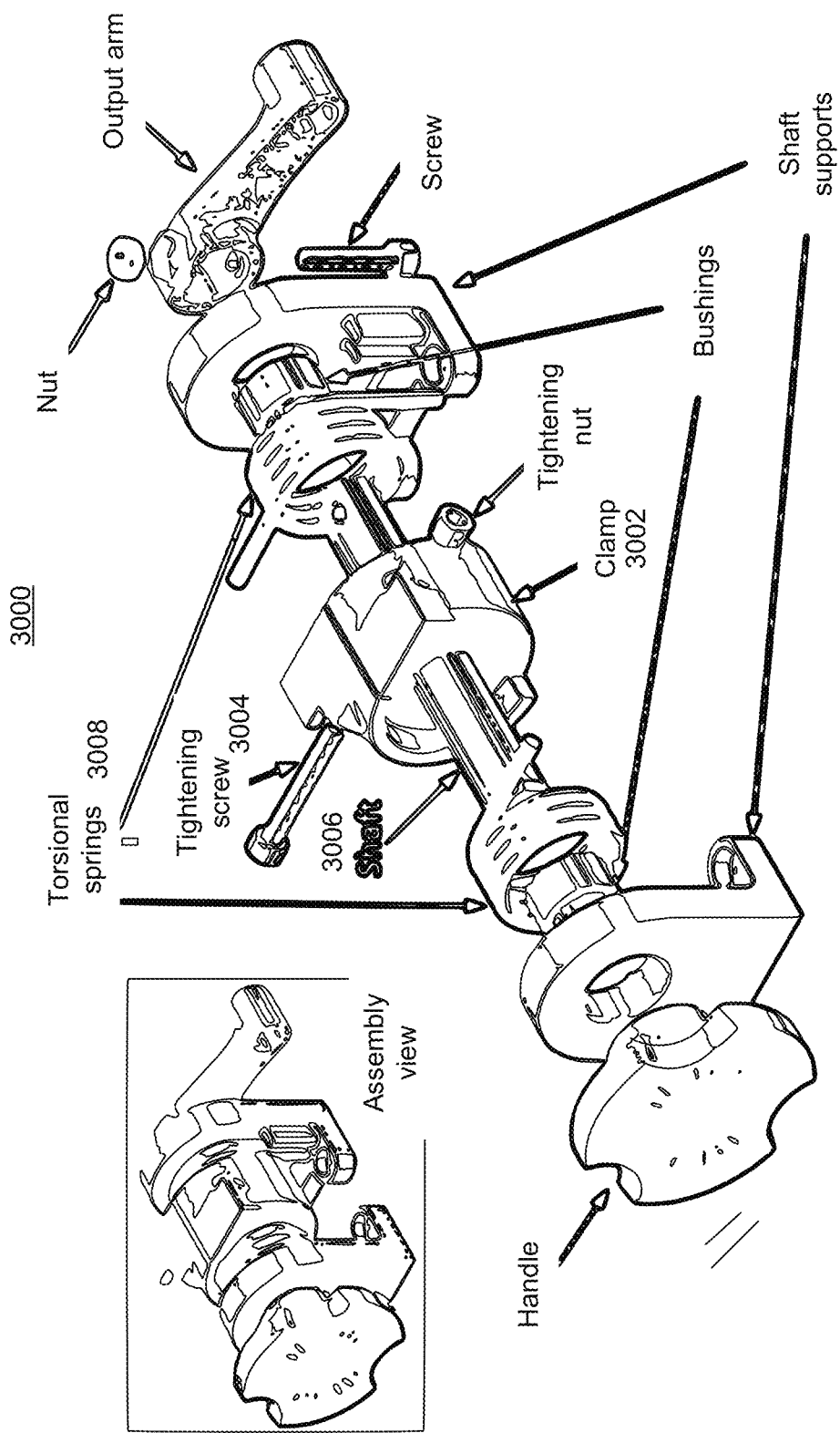
FIG. 30 shows the spring actuator employed in the embodiment of FIG. 29.

In embodiments, the spring actuator 3000 may be as described now to provide torque to balance the weight of the head at a desired configuration, as shown in FIG. 30. A clamp 3002 is used in the spring actuator 3000. This clamp 3002 may be made of plastic to save weight but may be made of metal, composite material, fiberglas, ceramic, or other materials. The clamp 3002 has a circular structure with a small opening gap. It can be tightened by a screw 3004 to engage the output shaft 3006 which is attached to a proximal joint of the brace. This enables the output shaft 3006 to provide a torque with the spring 3008 deflection. When the screw 3004 is loose, the clamp 3002 disengages and the shaft can move freely. This allows the change of the equilibrium configuration. A pair of right-handed torsional springs 3008 are used and placed symmetrically about the clamp 3002 along the shaft 3006 axis in order to provide a dual-directional torque. The springs 3008 may be (and were for the testing examples and data) selected based on their size, maximum torque, and maximum angular displacement.

The forward kinematics problem was defined as finding the orientation of the end-effecter with measurements of the angles of three proximal revolute joints. For the design, the forward kinematics was solved numerically using data recorded by potentiometers installed in the second revolute joints of each chain. This choice was made due to the limited space on the proximal joints to place another potentiometer.

The mechanical components of the brace were 3D printed. Additional padding may be used to fit the brace on the user. The entire brace weighs approximately 1.0 kg.

The spring-loaded brace was evaluated through a human experiment with ten healthy subjects (Table A1). The experiments validated the mathematical model of the system and confirmed that the brace is capable of supporting the head at a desired equilibrium while allowing movements to the user around this nominal configuration.

The experiment was designed as a comparison study and it was composed of two sessions. The springs were not tightened to the brace in Session I while in Session II the springs were loaded. Each subject wore the brace and sat on a stationary stool in both sessions. As shown in FIG. 31, muscle activations were monitored using surface electromyography (sEMG) from six muscles around the neck area: left/right sternocleidomastoid (SCM), left/right splenius capitis (SPC), and left/right trapezius (TRAP) muscles. Infrared markers were placed on the brace while a motion capture system consisting of eight cameras (Bonita, Vicon Motion Systems, Oxford, UK) recorded the motions of the markers. The interaction forces between a subject and the end-effector of the brace were recorded through the six-axis force/torque sensor. The placement of this force/torque sensor was shown in FIG. 29. All sensors were synchronized by an electrical trigger sent by a microcontroller (myRIO-1900, National Instruments, Austin, Tex., USA).

Except for the EMG system (TeleMyo DTS, Noraxon, Ariz., USA) which was sampled at 1.5 kHz, all sensors were sampled at 100 Hz. The EMG data were post-processed in software (Noraxon MR 3.6), with the steps of (1) ECG reduction, (2) filtering using a FIR bandwidth filter (2.5-500 Hz), (3) full wave rectification, (4) smoothing using RMS algorithm, and (5) normalization by the largest value from each channel in both sessions of the experiment.

In each session, the subjects performed two tasks. In the first task, they were asked to stay still in the neutral configuration with the head upright for 30 seconds. The subjects were then asked to flex the head forward, extend backwards, bend to the left and then to the right, and rotate towards left and then right as far as they could or were allowed by the brace. In the second task, the subjects were asked to keep the head static for two minutes with the head flexed forward by 20 degrees. The subjects were verbally encouraged to rely on the support from the brace in Session II.

TABLE A1

Subject characteristics (7 males and 3 females)

| Parameter | Mean | Standard Deviation | Range |
|---|---|---|---|
| Age (y) | 27.1 | 3.2 | 23-32 |
| Height (cm) | 176.1 | 7.6 | 163-190 |
| Weight (kg) | 77.9 | 15.1 | 60-112 |
| Shoulder Width (cm) | 35.4 | 2.1 | 31-38.5 |
| Neck Length (cm) | 13.4 | 1.0 | 12.5-15 |
| Neck Circumference (cm) | 36.3 | 3.0 | 31.5-42.5 |
| Forehead Circumference (cm) | 57.5 | 1.0 | 55.5-59.5 |

In Task 1 of Session II, the springs were tightened when the head was at the neutral configuration (upright). This means that the springs are deflected and transmit forces through the end-effector to the head only if the head deviates from the neutral configuration. Essentially, the springs stabilize the head. This task was intended to evaluate the efficacy of the system to keep the head in the neutral configuration and allow local movement to the head. A smaller range of motion and larger interaction force between the brace and the head were expected in Session II.

In Task 2 of Session II, the free angles of the springs were computed in the software using the method introduced in Section 2 and the springs were tightened. The weight of the head was assumed to be 5 kg and this created an external load on the head mount of the brace. Once the springs were tightened, the head was gently pushed towards the target position (flexion 20). Then the subject was asked to move around locally and find a configuration in which the head is most supported by the brace. This task was designed to validate the mathematical model as well as the efficacy of the brace in keeping the head static in the desired configuration. One target configuration was chosen to keep the experiment time within an hour. However, this 20-degree flexion is representative of the feature of the brace to provide compliant head support against gravity.

The representative data illustrate the performance of a subject during the experiment. The group data validate the model and confirmed that that the brace is capable of supporting 108 the head at a desired equilibrium while allowing movements to the user around this nominal configuration. Inventors hypothesized that the brace provides adequate support to a user in the desired head configuration and allows to perform local movements.

Figures 32A, 32B:
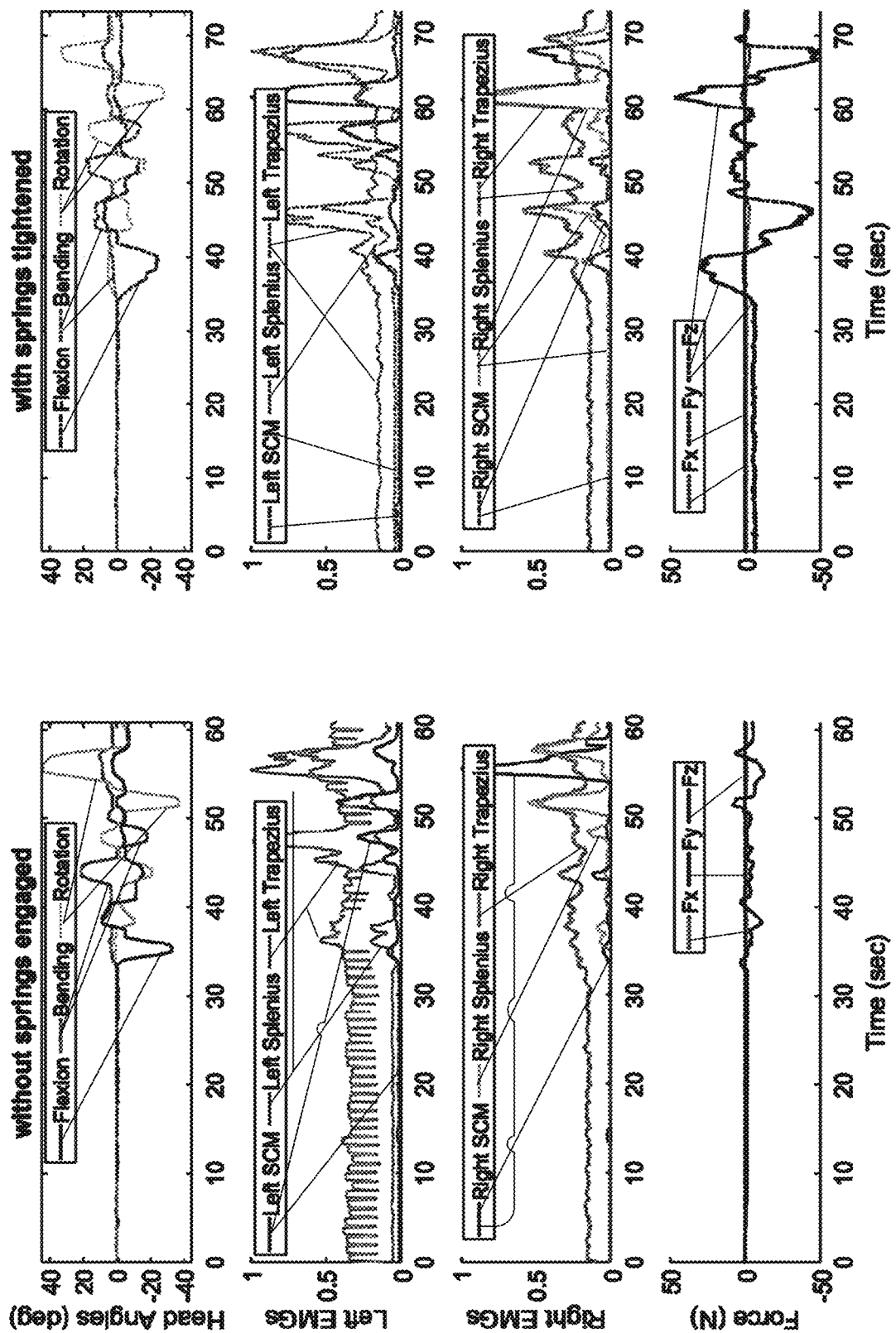
FIGS. 32A and 32B show representative data from trials with a subject during a Task 1 in two sessions with FIG. 32A showing results from a Session I (solid lines) without spring tightened, and FIG. 32B showing results from a session II with spring tightened (dashed lines) wherein a smaller range of motion and larger interactive forces are seen when the springs are tightened for this subject, with similar EMG activities in both conditions.

The brace exerted force on the head around the neutral configuration in Task 1. Representative data in Task 1 from a subject are shown in FIGS. 32A and 32B. The baseline plots are nearly the same as the subject maintains the head in the upright neutral configuration during the first 30 seconds. With the springs tightened at the neutral configuration, the subject experienced smaller range of motion in all directions and larger force from the brace during dynamic motions. These data illustrate that the spring torques were transmitted to the head as the subject attempted to move the head. This resulted in a smaller range of motion. The EMG activities between the two sessions are similar suggesting that the subject applied the same muscle activities when performing the task in both conditions. These data together demonstrate that the brace delivered support while providing compliance to the head of the subject.

The subject was asked to keep the head at a flexed configuration for 1 minute with the two different spring conditions. The head maintained close to the desired configuration (20° flexion) in both conditions, as shown in the head angle plots in FIGS. 33A and 33B. The difference is that the subject relied more on the support from the brace in Session II as the force/torque sensor registered higher forces. The force data was plotted in the sensor frame defined in FIG. 29. It indicates that the brace delivered a pulling force (12.57±0.68 N) on the head during the course of the task. The muscle EMG were recorded to be quite low in both sessions. This suggests that the subject did not fight against the force from the brace. As a result, this pulling force helped the subject to keep the head at that configuration.

The results in Task 2 of Session II can be used to validate the mathematical model in Section 2. The overall performance of the brace on all subjects during this trial is summarized in Table A2. The angle error was defined as the deviation of the mean of the actual head angle from the target (flexion). Similarly, the force error was defined as the deviation of the recorded force from the computed force at the actual head orientation.

The model may presume that the gravitational force is the only external force applied to the head and the weight of the head is 5 kg. With this assumption, the head can ideally be balanced at the target configuration with zero muscle input from the user. The results in Table A2 show the modeling errors. It shows that the mean error in the head angle and the force are small. On average, the brace balanced the heads close to the desired configuration. The large standard deviations may be due to the weight differences of the head, muscle activation, and other anthropometric parameters among the subjects.

TABLE A2

| Brace evaluation in Task 2 of Session II | |
|---|---|
| Outcome Measure | Value |
| Average angle error (°) | −3.29 ± 9.88 |
| Average force error (N) | 6.77 ± 9.55 |
| Average normalized EMG (%) | 13 ± 6 |

TABLE A3

Average measurement accuracy from all subjects.

| Trial | Average Mean Error) | Average RMS Error | Average Std. |
|---|---|---|---|
| SI (T1) | 0.97 ± 0.45 | 8.53 ± 2.50 | 8.45 ± 2.42 |
| SI (T2) | 3.20 ± 2.64 | 6.01 ± 5.96 | 1.16 ± 1.56 |
| SII (T1) | 1.02 ± 0.83 | 7.18 ± 1.92 | 7.07 ± 1.76 |
| SII (T2) | 4.01 ± 1.96 | 6.21 ± 4.00 | 0.52 ± 0.51 |

"S" and "T" stand for "Session" and "Task", respectively.
"Std." stands for standard deviation.

The measurement accuracy of the brace in different tasks was evaluated using potentiometer data against the camera system, as summarized in Table 3. These show comparable results to the inventor's previous works. The brace is less accurate when the subject reaches extreme brace configurations, causing deflection in the mechanical components.

Figure 34A:
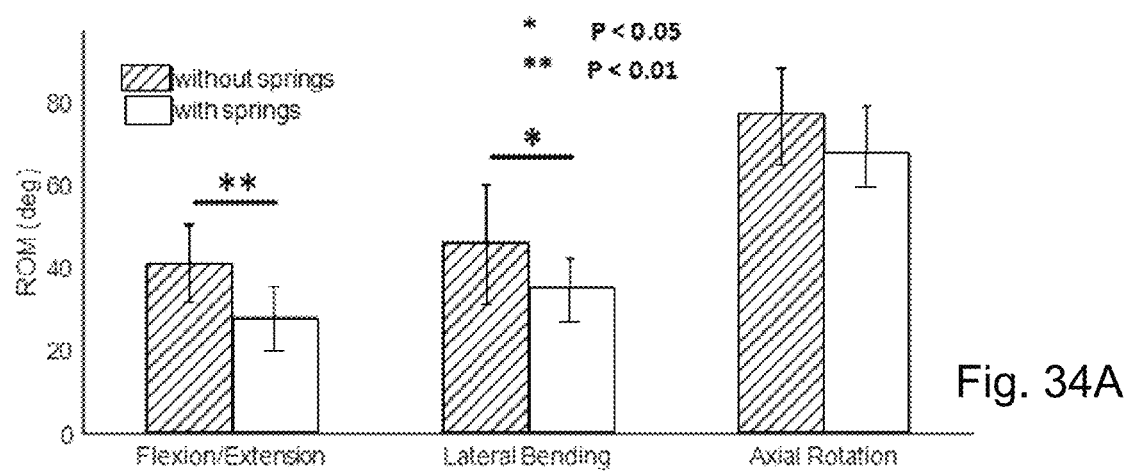
FIGS. 34A-34C show a comparison of average range of motions, average muscle activations, and average forces received by the head of the subjects as a group during dynamic movement in a Task 1 (static portion excluded) from two sessions where each bar represents
Figure 34B:
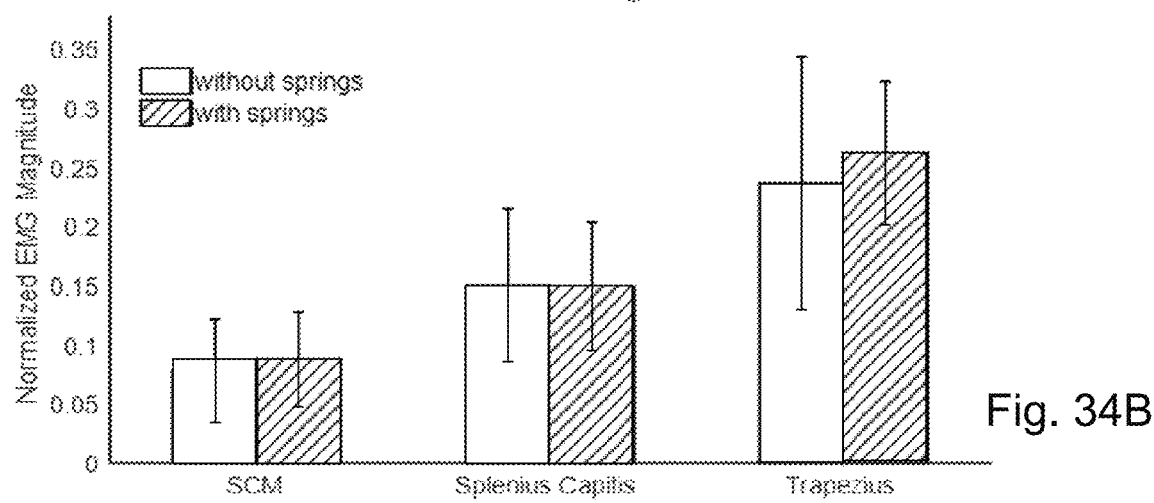
Figure 34C:
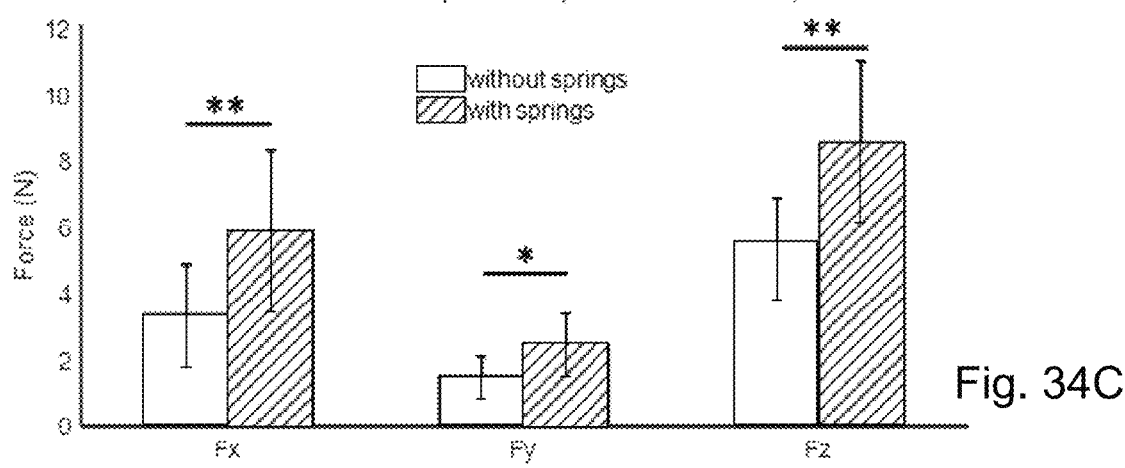

Inventors analyzed and compared data from all subjects during dynamic motion using a paired t-test. As shown in FIGS. 34A-34C, the average range of motion in Session II are smaller than the ones in Session I, especially in flexion/extension and lateral bending. The interaction forces are also significantly higher in Session II, indicating that the subjects needed to move against the spring torques. The muscle activations, however, do not show much difference in both sessions. This in fact makes the comparison of the range of motion and forces on the head meaningful because the subjects attempted the same motions in both sessions.

These results prove that the springs stabilize the head at the neutral configuration. It also shows that the subjects were able to perform local movements with the compliance of the system. Additionally, these results validated the capability of the spring actuators to engage or disengage the springs from the brace.

Figure 33B:
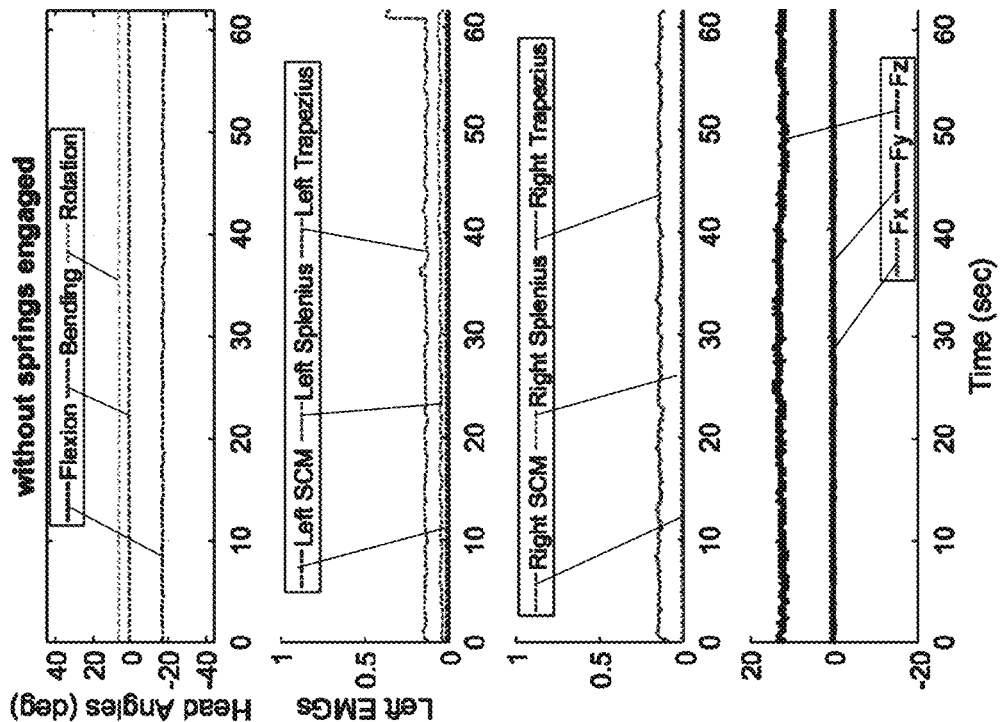
FIGS. 33A and 33B show representative data of a subject during Task 2 in both sessions. (Left) Results from Session I (solid lines), and (Right) results from Session II (dashed lines) where the head angles are almost the same in both conditions, but higher forces from the brace are shown when the springs were tightened and EMG magnitudes are at similar levels in this subject.
Figure 33A:
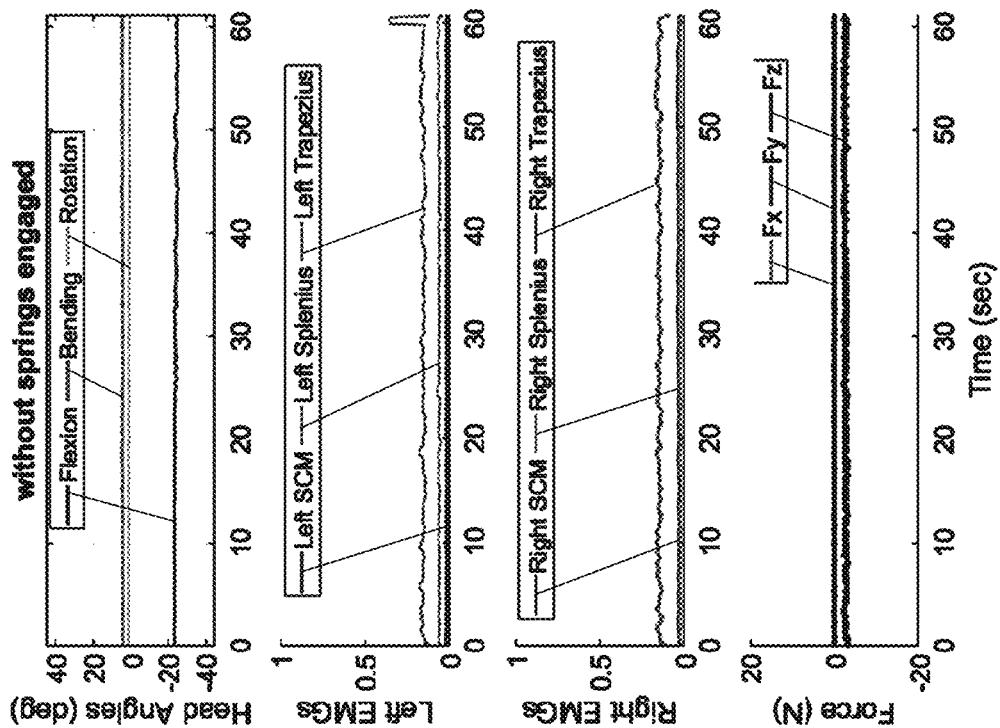

The results from Task 2 were compared to show the efficacy of the brace in supporting the head in an arbitrary configuration. As shown in FIGS. 33A and 33B, the head orientations were similar while less force was received by the person in Session I. It suggests that the head posture was held by the person when the springs were not tightened.

A paired t-test was used to analyze the group results, as shown in FIGS. 35A-35C. The flexion angles do not show much difference between both sessions, meaning that the subjects kept the head at the same configuration. The average EMG is lower in Session II, although no significance was found. It could be because the muscles do not activate much during the static portion of the task as opposed to the dynamic motions. The subjects experienced significantly larger forces from the brace during Session II, suggesting that the subjects were able to rely on the support from the brace to keep their head at the target configuration.

A passive neck brace was presented in this paper for patients with dropped head syndrome. The brace was designed to balance the head with the torques provided by three spring actuators. These actuators can be adjusted to balance the head at various configurations by tuning the free angles of the springs. Position measurements were embedded in the design for adjusting the springs precisely.

According to the disclosure, as described above, with respect to experiments, a mathematical model was proposed for the system using force balance. A Jacobian matrix was derived to relate the external forces applied at the end-effector to the torques received by the springs on the proximal joints. The efficacy of the neck brace was validated through a human experiment in which ten healthy young adults participated. The results showed that the brace provided accuracy in measuring the head orientation compared to a motion capture system.

This human experiment also evaluated the efficacy of the spring-loaded brace. It demonstrated that the subjects could rest their head at a target configuration. It also showed that the brace allowed the subjects to perform local head movement around the target equilibrium position.

Figure 36:
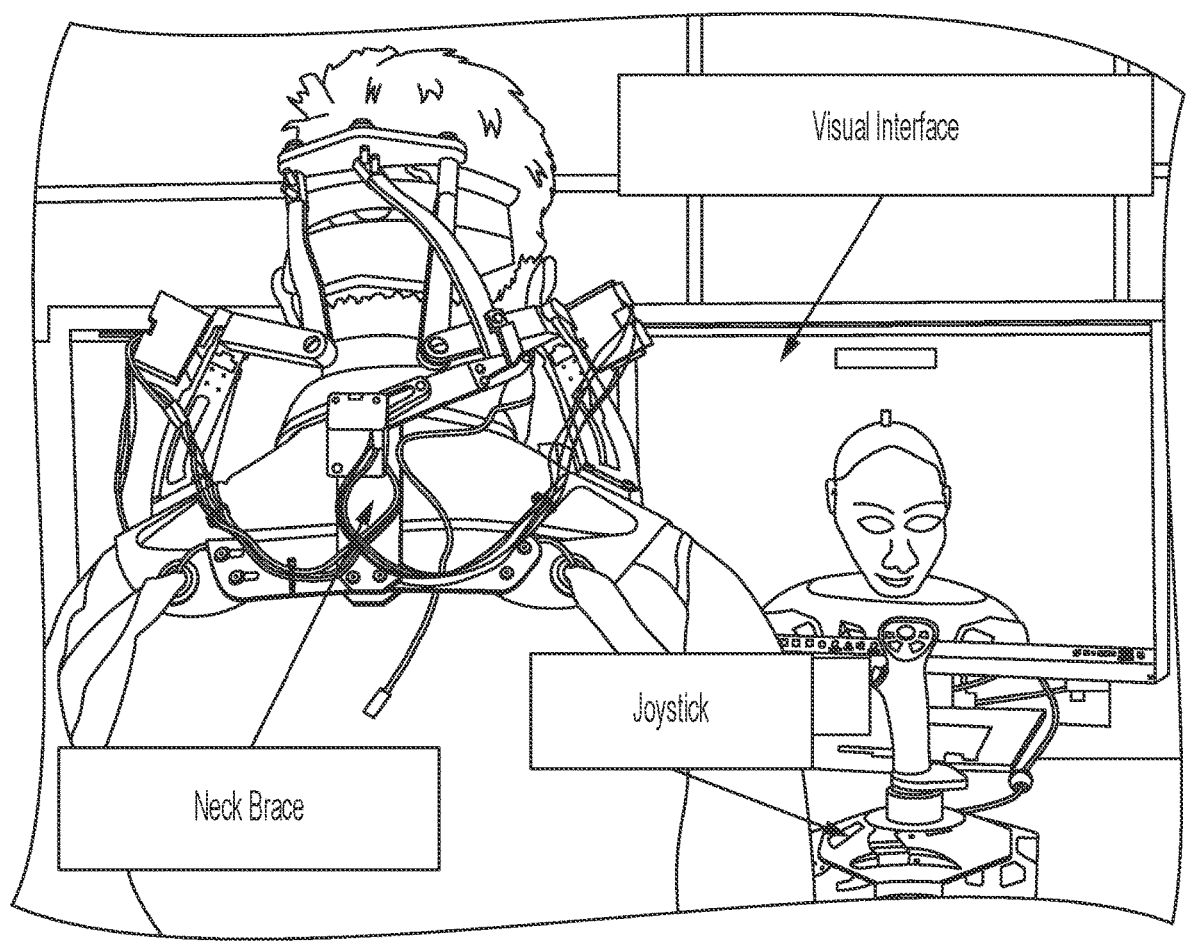
FIG. 36 shows a neck brace input device kinematically as in the above embodiments except that encoders are provided on the proximal R joint to allow its use as a computer input device similar to a joystick.

FIG. 36 shows a neck brace input device kinematically as in the above embodiments except that encoders are provided on the proximal R joint to allow its use as a computer input device similar to a joystick.

Figure 37:
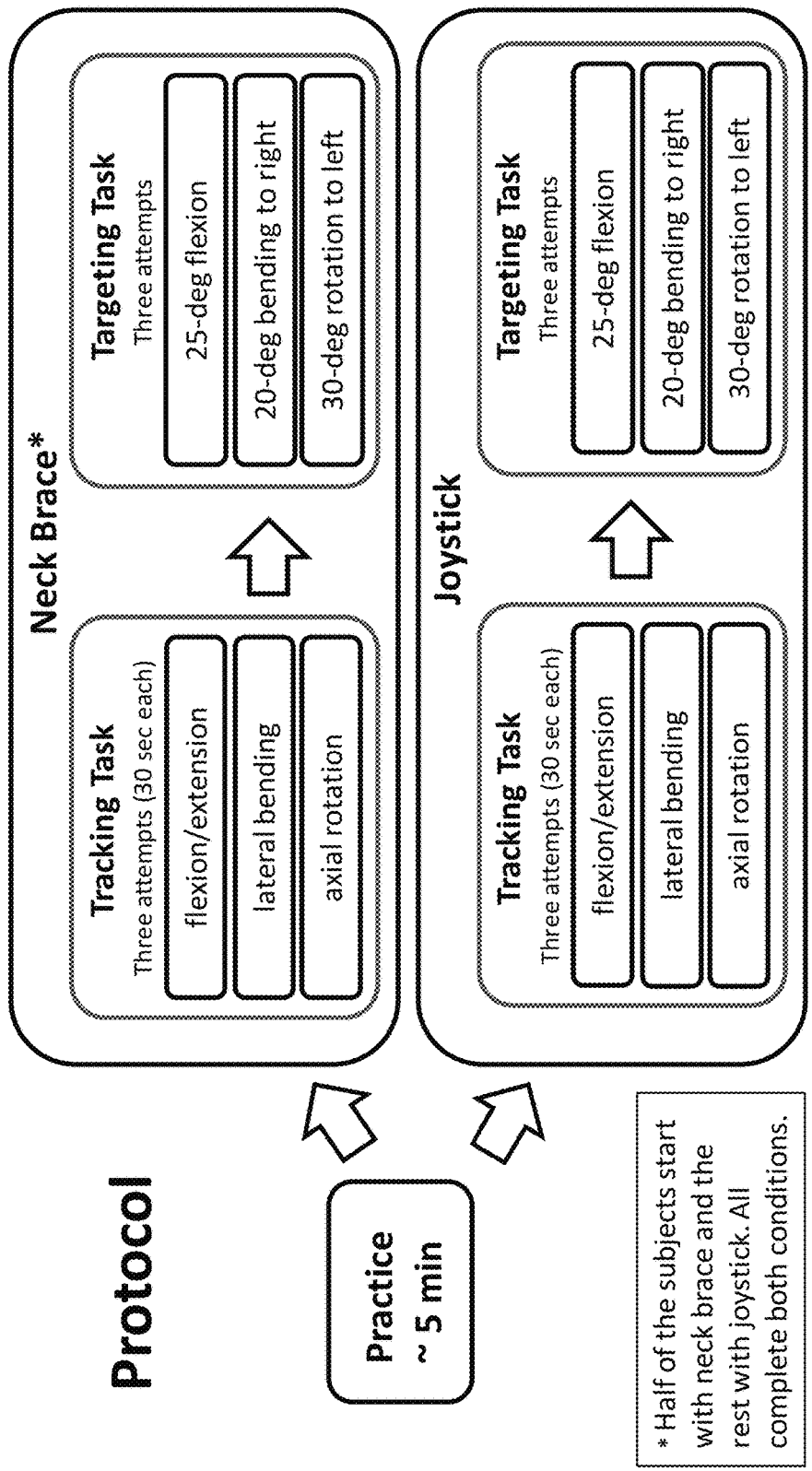
FIG. 37 shows a testing protocol summary for the neck brace input device of FIG. 36.
Figure 38:
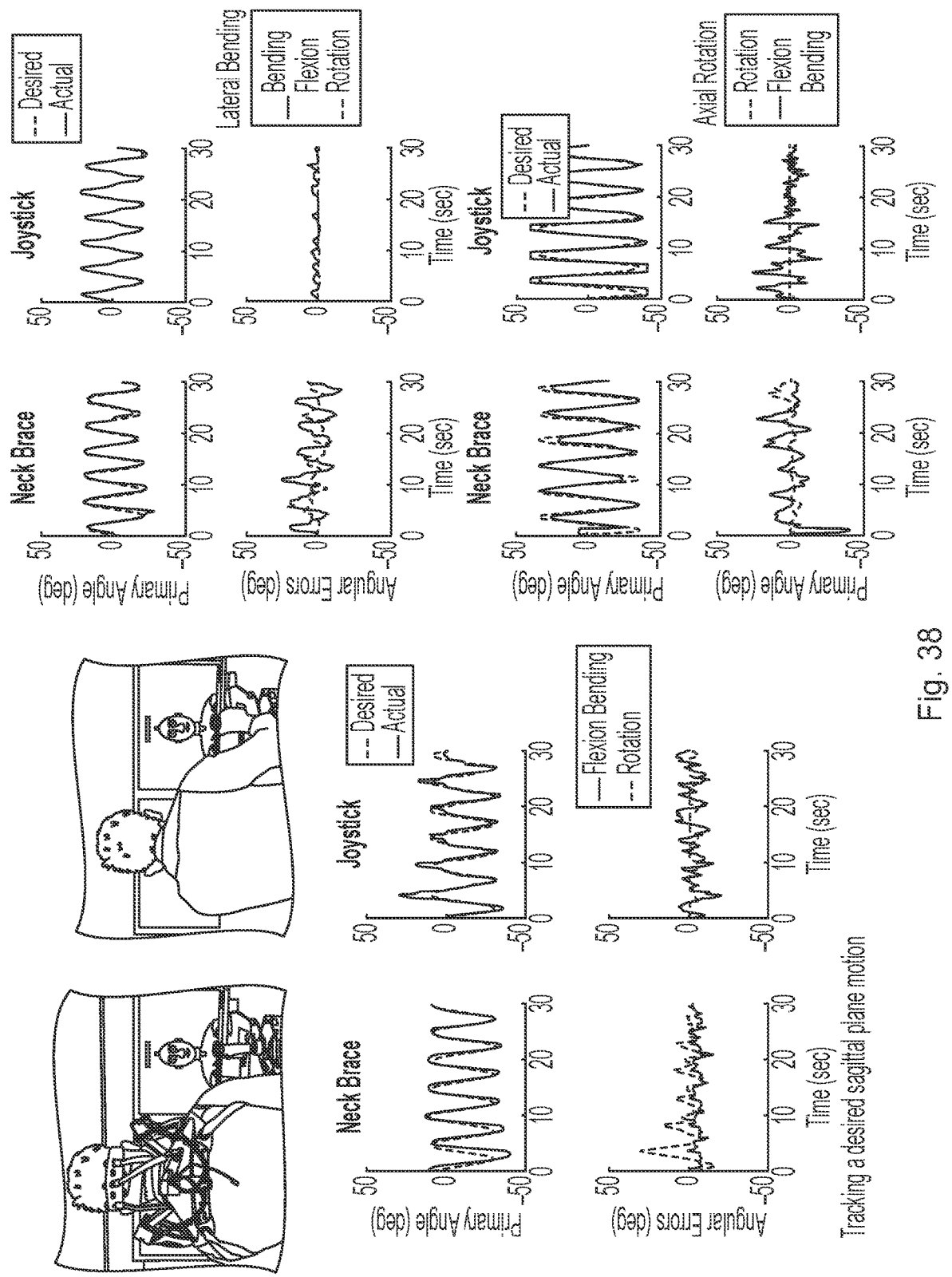
Figure 39:
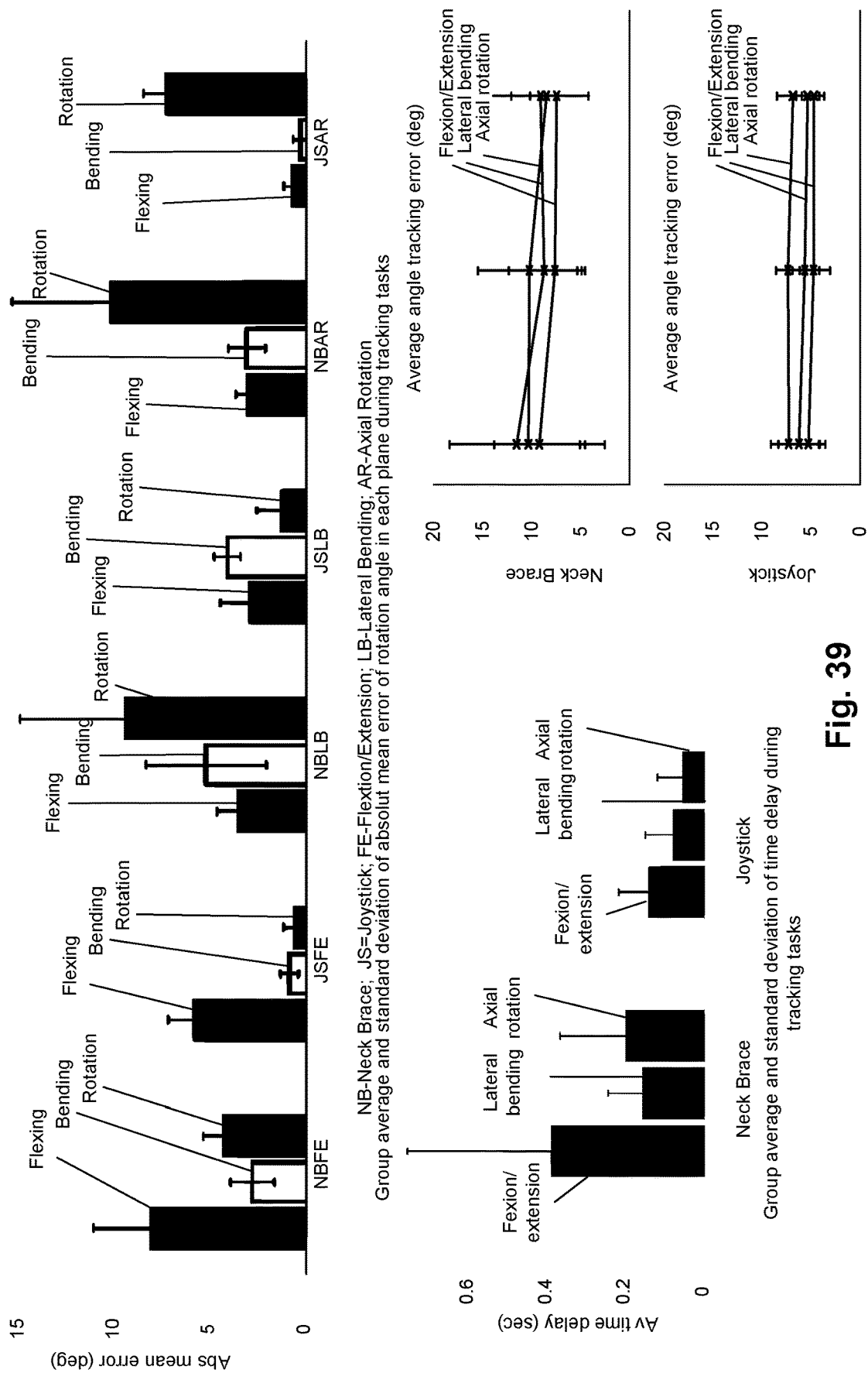
Figure 40:
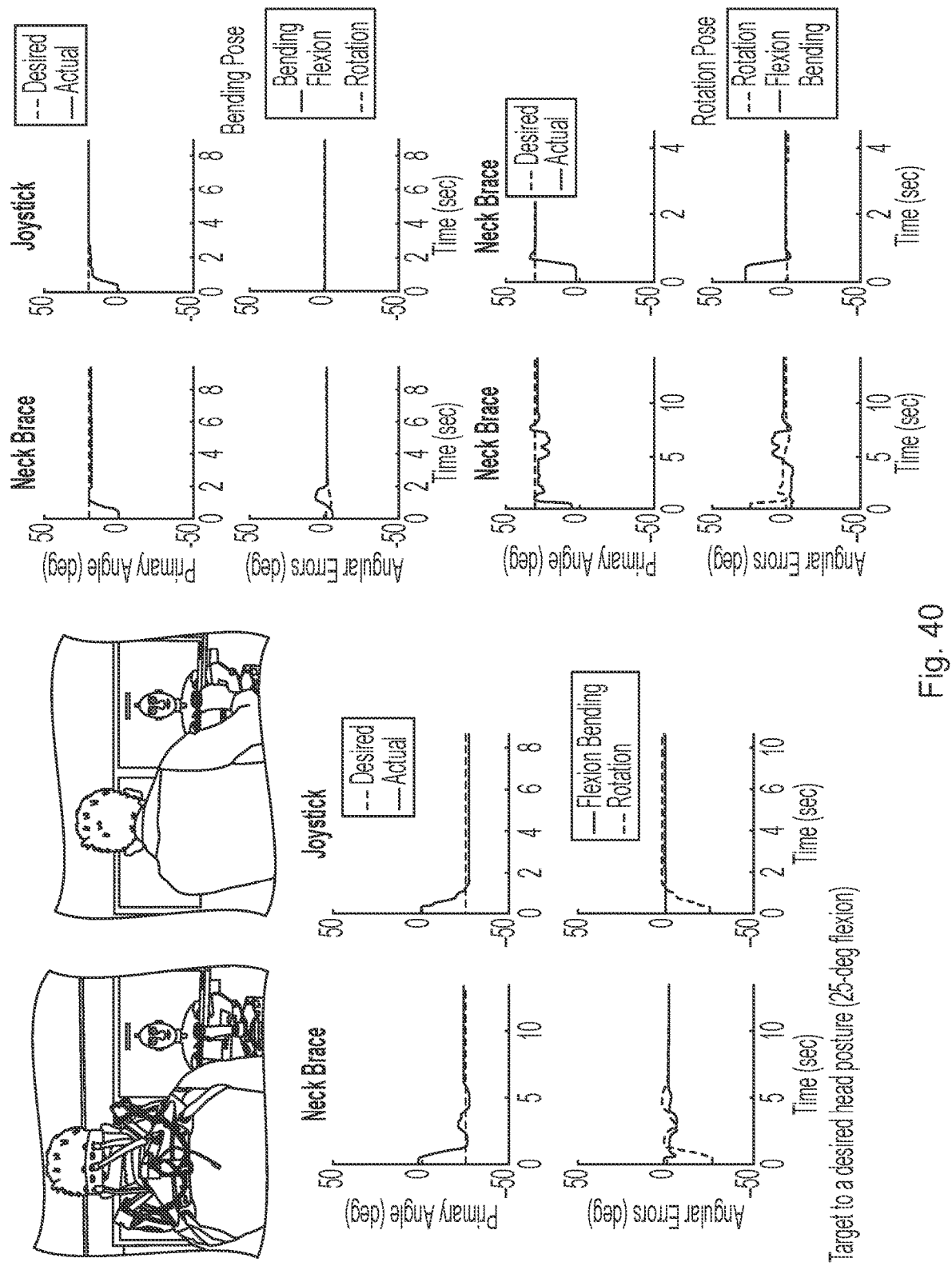

FIG. 37 shows a testing protocol summary for the neck brace input device of FIG. 36.

FIGS. 38-41 show results of the testing summarized in FIG. 37. The tests indicate that the neck brace input device can allow a user to operate a device whose function is similar to a joystick but includes the further rotational degree of freedom of a user's ability to rotate the head. Thus, the input device is capable of encoding flexion, bending, and rotation. It was found that when performing orientation tasks with visual feedback on a 2-dimensional screen, there is no difference in healthy subjects to command rotations using inputs from a hand-held joystick and a neck brace. Healthy subjects were able to understand the visual interface and perform designed tasks with both their wrist and neck. The group results show that the healthy subjects perform better ($p<0.05$) in tracking/target tasks using the hand-held joystick when compared to the neck brace input device. In three attempts, there is no significant adaptation found in subjects.

It will be appreciated that the modules, processes, systems, and sections described above can be implemented in hardware, hardware programmed by software, software instruction stored on a non-transitory computer readable medium or a combination of the above. For example, a method for of training, delivering therapy, diagnosing, performing biomechanical research and other functions can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Embodiments of the method, system, and computer program product can be implemented in hardware and/or software using any known or later developed systems or structures, devices and/or software by those of ordinary skill in the applicable art from the function description provided herein and with a general basic knowledge of sensor and control systems, kinematic design, optimization methods, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, Wearable Neck Apparatuses, Methods, and Systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A neck brace, comprising:
a stabilizing platform configured to affix to a torso of a wearer;
an effecter platform configured to affix to a head of a wearer;
the stabilizing and effecter platforms being connected by a mechanism characterized by at least two kinematic chains, each kinematic chain including, a first link connected by a first rotational joint to the stabilizing platform and a second link connected to the first link by a second rotational joint, wherein the second link of each kinematic chain is connected by a spherical joint to the effecter platform.

2. The neck brace of claim 1, wherein the first link and the second link are embodied in plastic or metal members.

3. The neck brace of claim 2, wherein the first rotational joint is connected to the stabilizing platform on a distal end of a riser that extends vertically above the the stabilizing platform.

4. The neck brace of claim 3, wherein the stabilizing platform is saddle-shaped adapted to conform to the top of the shoulders of the wearer.

5. The neck brace of claim 4, further comprising padding attached to a concave surface of the stabilizing platform.

6. The neck brace of any of claim 5, wherein the at least two kinematic chains are at least three kinematic chains.

7. The neck brace of claim 6, wherein the first rotational joint has a position sensor indicating an angular position of the first link relative to the stabilizing platform.

8. The neck brace of claim 7, wherein the position sensor includes an encoder.

9. The neck brace of claim 8, wherein the encoder includes a potentiometer.

10. The neck brace of claim 7, wherein the first rotational joint has a motor drive controlled by a controller, permitting the controller to define a force tunnel for each of the at least three kinematic chains.

11. The brace of any foregoing claim after claim 1, wherein the connection between the stabilizing platform and effecter platform includes at least three rotational-rotational-spherical kinematic chains.

12. The brace of claim 11, wherein the two rotational joints have respective axes that cross.

13. The brace of claim 11, wherein the two rotational joints have respective axes that cross at different locations in 3D space.

14. The brace of claim 11, wherein the two rotational joints have respective axes that cross at points spaced apart from the first link and the second link defined by the at least two kinematic chains and toward the neck of a wearer of the stabilizing platform.

15. The brace of any foregoing claim after claim 1, wherein the effecter platform includes a headband configured to be positioned to wrap around the top of the head of the wearer.

16. The brace of any foregoing claim after claim 1, wherein the rotations of the first link and the second link defined by the at least two kinematic chains are sufficient to provide at least 80% of respective degrees of freedom.

17. The brace of any foregoing claim after claim 1, wherein one or more kinematic chains of said mechanism that includes an rotational joint further includes an urging mechanism connected to said mechanism in a position that cause said one or more chains rotational joint to rotate.

18. The brace of claim 17, wherein the urging mechanism includes a spring.

19. The brace of claim 17, wherein the urging mechanism includes an actuator.

20. The brace of claim 19, wherein the actuator is a rotary actuator.

21. The brace of claim 20, wherein the rotary actuator is a servomotor and further comprising a controller that creates a force field defined by a challenging force that adapted to resists movement of the head, with the magnitude of resistance varying with the possible positions of the wearer's head.

22. The brace of claim 21, wherein the servomotor is controlled by an eye-tracking input device.

* * * * *